United States Patent
Chandler et al.

(10) Patent No.: US 10,016,580 B2
(45) Date of Patent: Jul. 10, 2018

(54) METHODS FOR TREATING SINUS DISEASES

(71) Applicant: Biovision Technologies, Inc., Golden, CO (US)

(72) Inventors: Stephen W. Chandler, Montgomery, AL (US); David W. Sanso, Morrison, CO (US)

(73) Assignee: Biovision Technologies, LLC, Golden, CO (US)

( * ) Notice: Subject to any disclaimer, the term of this patent is extended or adjusted under 35 U.S.C. 154(b) by 226 days.

(21) Appl. No.: 15/166,102

(22) Filed: May 26, 2016

(65) Prior Publication Data

US 2016/0271375 A1    Sep. 22, 2016

Related U.S. Application Data

(63) Continuation-in-part of application No. 14/699,999, filed on Apr. 29, 2015, now Pat. No. 9,510,743, (Continued)

(51) Int. Cl.
  *A61B 1/06*    (2006.01)
  *A61M 25/10*    (2013.01)
  (Continued)

(52) U.S. Cl.
  CPC ... *A61M 25/10182* (2013.11); *A61B 1/00135* (2013.01); *A61B 1/015* (2013.01);
  (Continued)

(58) Field of Classification Search
  CPC .................. A61M 29/02; A61M 29/00; A61M 2210/0681; A61M 2210/0618;
  (Continued)

(56) References Cited

U.S. PATENT DOCUMENTS 2,434,875 A * 1/1948 Turnbull ................ A61M 11/00
              604/207
2,493,326 A * 1/1950 Trinder ............ A61B 17/12104
              604/907

(Continued)

FOREIGN PATENT DOCUMENTS

CA    2266958 A1    10/1999
EP    2522386 A2    11/2012
(Continued)

OTHER PUBLICATIONS

Agro, et al., "Lightwand intubation using the Trachlight(TM): a brief review of current knowledge," Canadian Journal of Anesthesia, (2000), pp. 592-599.
(Continued)

*Primary Examiner* — Eduardo C Robert
*Assistant Examiner* — Michelle C Eckman
(74) *Attorney, Agent, or Firm* — Faegre Baker Daniels LLP

(57) ABSTRACT

Methods and devices to quickly and accurately apply medication to a paranasal sinus are disclosed. Additionally, the methods and devices prevent the medication applied to a paranasal sinus from flowing down a patient's throat by expanding, using an inflation lumen of a device, an expandable member of the device adjacent to the patient's choana.

15 Claims, 36 Drawing Sheets

Related U.S. Application Data which is a continuation-in-part of application No. 14/572,353, filed on Dec. 16, 2014, now Pat. No. 9,516,995, which is a continuation-in-part of application No. 14/298,521, filed on Jun. 6, 2014, now Pat. No. 9,694,163.

(60) Provisional application No. 62/168,505, filed on May 29, 2015, provisional application No. 61/917,097, filed on Dec. 17, 2013.

(51) Int. Cl.
| | |
|---|---|
| *A61M 31/00* | (2006.01) |
| *A61B 1/00* | (2006.01) |
| *A61B 1/015* | (2006.01) |
| *A61B 17/24* | (2006.01) |
| *A61M 15/08* | (2006.01) |

(52) U.S. Cl.
CPC ............ *A61B 1/0623* (2013.01); *A61B 17/24* (2013.01); *A61M 31/00* (2013.01); *A61M 15/08* (2013.01); *A61M 25/1002* (2013.01); *A61M 25/1011* (2013.01); *A61M 2025/1052* (2013.01); *A61M 2202/048* (2013.01); *A61M 2210/06* (2013.01); *A61M 2210/0681* (2013.01)

(58) Field of Classification Search
CPC .. A61M 25/1002; A61M 25/10; A61M 25/04; A61M 25/1018; A61M 2025/105; A61M 31/002; A61M 31/00; A61M 3/0279; A61M 3/0262; A61M 3/0295; A61B 17/3421; A61B 1/06; A61B 1/00082; A61B 19/5202

See application file for complete search history.

(56) References Cited

U.S. PATENT DOCUMENTS

| | | | | |
|---|---|---|---|---|
| 2,847,997 | A * | 8/1958 | Tibone | A61B 17/12104 604/104 |
| 2,936,760 | A * | 5/1960 | Gants | A61M 25/1011 604/101.03 |
| 3,049,125 | A * | 8/1962 | Kriwkowitsch | A61B 17/12104 604/100.02 |
| 3,664,330 | A | 5/1972 | Deutsch | |
| 3,747,595 | A * | 7/1973 | Grossan | A61M 3/0279 601/160 |
| 3,766,924 | A * | 10/1973 | Pidgeon | A61B 17/12045 604/101.04 |
| 3,800,788 | A | 4/1974 | White | |
| 3,850,176 | A * | 11/1974 | Gottschalk | A61B 1/00082 604/907 |
| 3,903,893 | A * | 9/1975 | Scheer | A61B 17/12045 604/101.05 |
| 4,592,357 | A | 6/1986 | Ersek | |
| 4,606,346 | A * | 8/1986 | Berg | A61F 5/34 606/196 |
| 4,819,619 | A * | 4/1989 | Augustine | A61M 16/0488 128/200.26 |
| 4,883,465 | A * | 11/1989 | Brennan | A61M 27/00 604/43 |
| 4,886,493 | A * | 12/1989 | Yee | A61M 11/00 604/516 |
| 4,887,593 | A | 12/1989 | Wiley et al. | |
| 5,024,658 | A * | 6/1991 | Kozlov | A61B 17/12104 604/101.04 |
| 5,116,311 | A * | 5/1992 | Lofstedt | A61M 3/0262 128/200.22 |
| 5,189,727 | A | 2/1993 | Guerreri | |
| 5,193,525 | A | 3/1993 | Silverstein et al. | |
| 5,213,115 | A * | 5/1993 | Zytkovicz | A61M 5/488 128/898 |
| 5,215,536 | A * | 6/1993 | Lampropoulos | A61M 5/315 604/187 |
| 5,242,400 | A | 9/1993 | Blake et al. | |
| 5,370,640 | A | 12/1994 | Kolff | |
| 5,446,070 | A | 8/1995 | Mantelle | |
| 5,462,553 | A | 10/1995 | Dolgin | |
| 5,483,951 | A | 1/1996 | Frassica et al. | |
| 5,514,128 | A | 5/1996 | Hillsman et al. | |
| 5,531,676 | A | 7/1996 | Edwards et al. | |
| 5,534,242 | A | 7/1996 | Henry | |
| 5,546,964 | A * | 8/1996 | Stangerup | A61B 17/12104 128/898 |
| 5,599,304 | A | 2/1997 | Shaari | |
| 5,626,553 | A | 5/1997 | Frassica et al. | |
| 5,647,847 | A | 7/1997 | Lafontaine et al. | |
| 5,667,476 | A | 9/1997 | Frassica et al. | |
| 5,676,635 | A | 10/1997 | Levin | |
| 5,685,822 | A | 11/1997 | Harhen | |
| 5,718,666 | A | 2/1998 | Alarcon | |
| 5,735,817 | A | 4/1998 | Shantha | |
| 5,752,971 | A | 5/1998 | Rosenbluth et al. | |
| 5,792,100 | A | 8/1998 | Shantha | |
| 5,819,727 | A | 10/1998 | Linder | |
| 5,827,177 | A | 10/1998 | Oneda et al. | |
| 5,827,224 | A * | 10/1998 | Shippert | A61B 17/12022 604/104 |
| 5,858,331 | A | 1/1999 | Henry | |
| 5,876,329 | A | 3/1999 | Harhen | |
| 6,027,478 | A * | 2/2000 | Katz | A61B 17/12104 604/102.01 |
| 6,106,496 | A * | 8/2000 | Arnissolle | A61M 25/1018 604/207 |
| 6,174,280 | B1 | 1/2001 | Oneda et al. | |
| 6,190,330 | B1 | 2/2001 | Harhen | |
| 6,258,101 | B1 | 7/2001 | Blake et al. | |
| 6,322,542 | B1 * | 11/2001 | Nilson | A61M 31/00 604/257 |
| 6,350,231 | B1 | 2/2002 | Ailinger et al. | |
| 6,350,465 | B1 * | 2/2002 | Jonnalagadda | A61M 5/148 424/434 |
| 6,394,093 | B1 * | 5/2002 | Lethi | A61M 16/0461 128/207.13 |
| 6,413,499 | B1 * | 7/2002 | Clay | A61K 9/0043 424/450 |
| 6,432,986 | B2 | 8/2002 | Levin | |
| 6,461,294 | B1 | 10/2002 | Oneda et al. | |
| 6,491,940 | B1 * | 12/2002 | Levin | A61K 31/445 424/434 |
| 6,529,756 | B1 | 3/2003 | Phan et al. | |
| 6,530,881 | B1 | 3/2003 | Ailinger et al. | |
| 6,579,582 | B1 | 6/2003 | Harhen et al. | |
| D478,987 | S | 8/2003 | Groenke et al. | |
| 6,607,546 | B1 | 8/2003 | Murken | |
| 6,669,711 | B1 * | 12/2003 | Noda | A61B 17/12104 604/907 |
| 6,677,321 | B1 | 1/2004 | Levin | |
| 6,693,670 | B1 | 2/2004 | Stark | |
| 6,733,440 | B2 | 5/2004 | Ailinger et al. | |
| 6,740,030 | B2 | 5/2004 | Martone et al. | |
| 6,758,840 | B2 | 7/2004 | Knox | |
| 6,770,080 | B2 | 8/2004 | Kaplan et al. | |
| 6,793,661 | B2 | 9/2004 | Hamilton et al. | |
| 6,822,213 | B2 | 11/2004 | Stark | |
| 6,853,858 | B2 | 2/2005 | Shalev | |
| 6,902,535 | B2 * | 6/2005 | Eberhart | A61M 25/1018 600/585 |
| 7,025,923 | B2 | 4/2006 | Harhen et al. | |
| 7,056,284 | B2 | 6/2006 | Martone et al. | |
| 7,056,287 | B2 | 6/2006 | Taylor et al. | |
| 7,081,097 | B2 | 7/2006 | Martone et al. | |
| 7,112,578 | B2 | 9/2006 | Levin | |
| 7,117,033 | B2 | 10/2006 | Shalev et al. | |
| 7,120,489 | B2 | 10/2006 | Shalev et al. | |
| 7,131,969 | B1 | 11/2006 | Hovda et al. | |
| D534,216 | S | 12/2006 | Makower et al. | |
| 7,146,209 | B2 | 12/2006 | Gross et al. | |

(56) References Cited

U.S. PATENT DOCUMENTS

| | | | |
|---|---|---|---|
| 7,169,161 B2* | 1/2007 | Bonnette | A61M 25/09 604/96.01 |
| 7,190,998 B2 | 3/2007 | Shalev et al. | |
| D544,602 S | 6/2007 | Hughett et al. | |
| 7,336,309 B2 | 2/2008 | Stark | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| 7,507,200 B2 | 3/2009 | Okada | |
| 7,520,876 B2 | 4/2009 | Ressemann et al. | |
| 7,559,925 B2 | 7/2009 | Goldfarb et al. | |
| 7,561,919 B2 | 7/2009 | Shalev et al. | |
| 7,636,597 B2 | 12/2009 | Gross et al. | |
| 7,640,062 B2 | 12/2009 | Shalev | |
| 7,641,644 B2 | 1/2010 | Chang et al. | |
| 7,642,563 B2 | 1/2010 | Kang et al. | |
| 7,645,272 B2 | 1/2010 | Chang et al. | |
| 7,648,367 B1 | 1/2010 | Makower et al. | |
| 7,654,997 B2 | 2/2010 | Makower et al. | |
| 7,678,099 B2 | 3/2010 | Ressemann et al. | |
| 7,684,859 B2 | 3/2010 | Shalev et al. | |
| 7,704,259 B2 | 4/2010 | Kaplan et al. | |
| 7,717,933 B2 | 5/2010 | Becker | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,729,759 B2 | 6/2010 | Shalev et al. | |
| 7,740,642 B2 | 6/2010 | Becker | |
| 7,749,515 B2 | 7/2010 | Blumenfeld | |
| 7,753,929 B2 | 7/2010 | Becker | |
| 7,753,930 B2 | 7/2010 | Becker | |
| 7,771,409 B2 | 8/2010 | Chang et al. | |
| 7,785,315 B1 | 8/2010 | Muni et al. | |
| 7,799,337 B2 | 9/2010 | Levin | |
| 7,803,150 B2 | 9/2010 | Chang et al. | |
| 7,837,672 B2* | 11/2010 | Intoccia | A61B 17/22 604/101.01 |
| 7,842,062 B2 | 11/2010 | Keith et al. | |
| 7,854,744 B2 | 12/2010 | Becker | |
| 7,877,147 B2 | 1/2011 | Shalev et al. | |
| 7,879,011 B2 | 2/2011 | Chang | |
| 7,879,061 B2 | 2/2011 | Keith et al. | |
| 7,908,000 B2 | 3/2011 | Shalev | |
| 7,918,871 B2 | 4/2011 | Truitt et al. | |
| D640,374 S | 6/2011 | Liu et al. | |
| D643,115 S | 8/2011 | Gonzales et al. | |
| 8,010,189 B2 | 8/2011 | Shalev | |
| 8,012,084 B2* | 9/2011 | Machida | A61B 1/00082 600/114 |
| 8,025,635 B2 | 9/2011 | Eaton et al. | |
| 8,052,693 B2 | 11/2011 | Shahoian | |
| 8,080,000 B2 | 12/2011 | Makower et al. | |
| 8,088,101 B2 | 1/2012 | Chang et al. | |
| 8,090,433 B2 | 1/2012 | Makower et al. | |
| 8,100,933 B2 | 1/2012 | Becker | |
| 8,114,062 B2 | 2/2012 | Muni et al. | |
| 8,114,113 B2 | 2/2012 | Becker | |
| 8,118,757 B2 | 2/2012 | Morriss | |
| 8,123,722 B2 | 2/2012 | Chang et al. | |
| 8,142,422 B2 | 3/2012 | Makower et al. | |
| D658,291 S | 4/2012 | Jenkins et al. | |
| 8,146,400 B2 | 4/2012 | Goldfarb et al. | |
| 8,172,828 B2 | 5/2012 | Chang et al. | |
| 8,182,432 B2 | 5/2012 | Kim et al. | |
| 8,190,389 B2 | 5/2012 | Kim et al. | |
| 8,192,420 B2 | 6/2012 | Morriss et al. | |
| 8,224,438 B2 | 7/2012 | Levin | |
| 8,229,571 B2 | 7/2012 | Lorian et al. | |
| 8,231,588 B2 | 7/2012 | Xia | |
| 8,241,266 B2 | 8/2012 | Keith et al. | |
| 8,241,641 B2 | 8/2012 | Blumenfeld | |
| 8,249,700 B2 | 8/2012 | Clifford et al. | |
| 8,277,478 B2* | 10/2012 | Drontle | A61B 17/24 606/196 |
| 8,282,667 B2 | 10/2012 | Drontle et al. | |
| 8,308,709 B2 | 11/2012 | Chang | |
| 8,313,520 B2 | 11/2012 | Barbut et al. | |
| 8,317,816 B2 | 11/2012 | Becker | |
| 8,337,454 B2 | 12/2012 | Eaton et al. | |
| 8,348,969 B2 | 1/2013 | Keith et al. | |
| 8,360,968 B2 | 1/2013 | Hadani | |
| 8,388,600 B1* | 3/2013 | Eldredge | A61M 31/00 604/514 |
| 8,388,642 B2 | 3/2013 | Muni et al. | |
| 8,412,336 B2* | 4/2013 | Pless | A61B 1/00135 607/115 |
| 8,414,473 B2 | 4/2013 | Jenkins et al. | |
| 8,425,457 B2 | 4/2013 | John et al. | |
| 8,425,488 B2 | 4/2013 | Clifford et al. | |
| 8,435,290 B2 | 5/2013 | Clifford et al. | |
| 8,439,687 B1 | 5/2013 | Morriss et al. | |
| 8,452,392 B2 | 5/2013 | Morriss et al. | |
| D683,852 S | 6/2013 | Gonzales et al. | |
| 8,480,658 B1 | 7/2013 | Nakao | |
| 8,485,199 B2 | 7/2013 | Morriss | |
| 8,486,155 B2* | 7/2013 | McAlister | A61B 17/00491 604/93.01 |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,623,043 B1 | 1/2014 | Keith et al. | |
| 8,636,684 B2 | 1/2014 | Deem et al. | |
| 8,657,846 B2 | 2/2014 | Keith et al. | |
| 8,690,839 B2* | 4/2014 | Xia | A61M 39/1011 604/187 |
| 8,702,626 B1 | 4/2014 | Kim et al. | |
| 8,715,169 B2 | 5/2014 | Chang et al. | |
| 8,721,591 B2 | 5/2014 | Chang et al. | |
| 8,740,839 B2 | 6/2014 | Eaton et al. | |
| 8,740,929 B2 | 6/2014 | Gopferich et al. | |
| 8,747,389 B2 | 6/2014 | Goldfarb et al. | |
| 8,764,709 B2 | 7/2014 | Chang et al. | |
| 8,764,726 B2 | 7/2014 | Chang et al. | |
| 8,764,729 B2 | 7/2014 | Muni et al. | |
| 8,764,786 B2 | 7/2014 | Becker | |
| 8,777,926 B2 | 7/2014 | Chang et al. | |
| 8,801,670 B2 | 8/2014 | Drontle et al. | |
| 8,828,041 B2 | 9/2014 | Chang et al. | |
| 8,834,513 B2 | 9/2014 | Hanson et al. | |
| 8,852,143 B2 | 10/2014 | Chang et al. | |
| 8,858,551 B2 | 10/2014 | Naito | |
| 8,858,586 B2 | 10/2014 | Chang et al. | |
| 8,858,974 B2 | 10/2014 | Eaton et al. | |
| 8,864,787 B2 | 10/2014 | Muni et al. | |
| 8,876,794 B2 | 11/2014 | Xia | |
| 8,882,795 B2 | 11/2014 | Drontle et al. | |
| 8,888,686 B2 | 11/2014 | Drontle et al. | |
| 8,894,614 B2 | 11/2014 | Muni et al. | |
| 8,905,922 B2 | 12/2014 | Makower et al. | |
| 8,905,980 B2 | 12/2014 | Xia | |
| 8,915,938 B2* | 12/2014 | Keith | A61B 1/00154 606/196 |
| 8,932,276 B1 | 1/2015 | Morriss et al. | |
| 8,954,149 B2 | 2/2015 | Shalev | |
| 8,956,280 B2* | 2/2015 | Eversull | A61B 1/00073 600/104 |
| 8,961,398 B2 | 2/2015 | Makower et al. | |
| 8,986,340 B2 | 3/2015 | Drontle et al. | |
| D730,515 S | 5/2015 | Shahidi Bonjar | |
| D735,848 S | 8/2015 | Dubuc et al. | |
| D736,922 S | 8/2015 | Allen et al. | |
| 9,248,266 B2 | 2/2016 | Chandler et al. | |
| D772,406 S | 11/2016 | Sanso et al. | |
| 9,510,743 B2 | 12/2016 | Chandler et al. | |
| 9,516,995 B2 | 12/2016 | Chandler et al. | |
| 9,694,163 B2* | 7/2017 | Chandler | A61M 25/10182 |
| 9,757,455 B2* | 9/2017 | Roberts | A61K 45/06 |
| 9,839,347 B2* | 12/2017 | Chandler | A61B 1/0684 |
| 2001/0002999 A1 | 6/2001 | Neuser et al. | |
| 2001/0004644 A1 | 6/2001 | Levin | |
| 2002/0010194 A1 | 1/2002 | Levin | |

(56) References Cited

U.S. PATENT DOCUMENTS

| | | |
|---|---|---|
| 2002/0062119 A1* | 5/2002 | Zadno-Azizi .... A61B 17/12109 604/509 |
| 2002/0161379 A1 | 10/2002 | Kaplan et al. |
| 2003/0120256 A1* | 6/2003 | Lary ................ A61M 25/00 604/509 |
| 2003/0133877 A1* | 7/2003 | Levin ................ A61K 9/0043 424/45 |
| 2003/0208249 A1 | 11/2003 | Chen |
| 2004/0064150 A1 | 4/2004 | Becker |
| 2004/0116958 A1 | 6/2004 | Gopferich et al. |
| 2004/0243172 A1* | 12/2004 | Hogle ................ A61B 17/24 606/199 |
| 2005/0072430 A1* | 4/2005 | Djupesland ....... A61M 15/0091 128/206.11 |
| 2005/0080357 A1* | 4/2005 | Eberhart .......... A61M 25/1018 600/585 |
| 2005/0113798 A1* | 5/2005 | Slater ................ A61M 25/01 604/508 |
| 2005/0124856 A1* | 6/2005 | Fujikura .......... A61B 17/3415 600/115 |
| 2005/0228452 A1* | 10/2005 | Mourlas ............ A61B 1/00071 607/3 |
| 2005/0240147 A1* | 10/2005 | Makower ............ A61B 17/24 604/96.01 |
| 2005/0245894 A1* | 11/2005 | Zadno-Azizi .... A61B 17/12045 604/509 |
| 2005/0245906 A1* | 11/2005 | Makower .................. A61B 5/06 604/891.1 |
| 2005/0281751 A1 | 12/2005 | Levin |
| 2006/0004286 A1 | 1/2006 | Chang et al. |
| 2006/0004323 A1 | 1/2006 | Chang et al. |
| 2006/0063973 A1* | 3/2006 | Makower ............ A61B 1/00135 600/114 |
| 2006/0095066 A1 | 5/2006 | Chang et al. |
| 2006/0106361 A1 | 5/2006 | Muni et al. |
| 2006/0155304 A1 | 7/2006 | Kaplan et al. |
| 2006/0161044 A1 | 7/2006 | Oneda et al. |
| 2006/0167439 A1* | 7/2006 | Kalser ............... A61M 25/0017 604/544 |
| 2006/0189844 A1 | 8/2006 | Tien |
| 2006/0189847 A1 | 8/2006 | Yee et al. |
| 2006/0210605 A1 | 9/2006 | Chang et al. |
| 2007/0015964 A1* | 1/2007 | Eversull ............ A61B 1/00082 600/114 |
| 2007/0020254 A1 | 1/2007 | Levin |
| 2007/0043327 A1 | 2/2007 | Knox |
| 2007/0073269 A1* | 3/2007 | Becker ................ A61M 3/0295 604/509 |
| 2007/0112257 A1 | 5/2007 | Hensler |
| 2007/0119451 A1* | 5/2007 | Wang ................ A61M 15/0028 128/203.15 |
| 2007/0129705 A1 | 6/2007 | Trombley et al. |
| 2007/0129751 A1 | 6/2007 | Muni et al. |
| 2007/0135789 A1 | 6/2007 | Chang et al. |
| 2007/0142709 A1 | 6/2007 | Martone et al. |
| 2007/0167682 A1* | 7/2007 | Goldfarb ............ A61B 1/00135 600/114 |
| 2007/0179518 A1 | 8/2007 | Becker |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0250105 A1 | 10/2007 | Ressemann et al. |
| 2007/0260264 A1 | 11/2007 | Nobis et al. |
| 2007/0265618 A1 | 11/2007 | Long |
| 2007/0267011 A1 | 11/2007 | Deem et al. |
| 2007/0282305 A1 | 12/2007 | Goldfarb et al. |
| 2007/0293726 A1* | 12/2007 | Goldfarb ............ A61B 1/0014 600/178 |
| 2007/0293727 A1 | 12/2007 | Goldfarb et al. |
| 2007/0293946 A1 | 12/2007 | Gonzales et al. |
| 2008/0004613 A1* | 1/2008 | Barbut .................. A61F 7/12 606/21 |
| 2008/0015472 A1 | 1/2008 | Ressemann et al. |
| 2008/0015540 A1 | 1/2008 | Muni et al. |
| 2008/0082045 A1* | 4/2008 | Goldfarb ............ A61B 1/00126 604/96.01 |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125626 A1* | 5/2008 | Chang .................. A61B 17/24 600/104 |
| 2008/0125720 A1 | 5/2008 | Kim et al. |
| 2008/0132938 A1 | 6/2008 | Chang et al. |
| 2008/0154237 A1 | 6/2008 | Chang et al. |
| 2008/0154250 A1 | 6/2008 | Makower et al. |
| 2008/0172033 A1 | 7/2008 | Keith et al. |
| 2008/0183128 A1 | 7/2008 | Morriss et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0269643 A1 | 10/2008 | Morriss |
| 2008/0275483 A1 | 11/2008 | Makower et al. |
| 2008/0279895 A1* | 11/2008 | Blumenfeld ......... A61K 9/0014 424/239.1 |
| 2008/0281156 A1 | 11/2008 | Makower et al. |
| 2008/0281300 A1 | 11/2008 | Morriss |
| 2008/0281349 A2 | 11/2008 | Becker |
| 2008/0287908 A1 | 11/2008 | Muni et al. |
| 2008/0293999 A1 | 11/2008 | Halahmi |
| 2008/0319424 A1 | 12/2008 | Muni et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0054803 A1* | 2/2009 | Saadat ................. A61B 1/0008 600/546 |
| 2009/0076331 A1 | 3/2009 | Konwitz et al. |
| 2009/0093823 A1 | 4/2009 | Chang et al. |
| 2009/0125046 A1 | 5/2009 | Becker |
| 2009/0156980 A1 | 6/2009 | Eaton et al. |
| 2009/0163848 A1 | 6/2009 | Morriss et al. |
| 2009/0163890 A1 | 6/2009 | Clifford et al. |
| 2009/0171301 A1 | 7/2009 | Becker |
| 2009/0181074 A1 | 7/2009 | Makower et al. |
| 2009/0187098 A1 | 7/2009 | Makower et al. |
| 2009/0198216 A1 | 8/2009 | Muni et al. |
| 2009/0214466 A1 | 8/2009 | Levin |
| 2009/0227900 A1 | 9/2009 | Kim et al. |
| 2009/0240112 A1 | 9/2009 | Goldfarb et al. |
| 2009/0240237 A1 | 9/2009 | Goldfarb et al. |
| 2009/0306588 A1* | 12/2009 | Nguyen ................ A61B 18/04 604/96.01 |
| 2009/0312696 A1* | 12/2009 | Copa .................... A61M 25/007 604/43 |
| 2009/0312745 A1 | 12/2009 | Goldfarb et al. |
| 2009/0318797 A1 | 12/2009 | Hadani |
| 2010/0010302 A1 | 1/2010 | Hadani |
| 2010/0016844 A1* | 1/2010 | Patel, Jr. ................ A61B 90/30 606/15 |
| 2010/0030031 A1 | 2/2010 | Goldfarb et al. |
| 2010/0030113 A1* | 2/2010 | Morriss ................ A61B 1/233 600/585 |
| 2010/0030131 A1 | 2/2010 | Morriss et al. |
| 2010/0030187 A1* | 2/2010 | Xia ....................... A61M 11/00 604/514 |

(56) References Cited

U.S. PATENT DOCUMENTS

| | | | |
|---|---|---|---|
| 2010/0030188 A1* | 2/2010 | Xia | A61M 11/06 604/514 |
| 2010/0042046 A1 | 2/2010 | Chang et al. | |
| 2010/0056867 A1 | 3/2010 | LaBombard et al. | |
| 2010/0057048 A1* | 3/2010 | Eldredge | A61M 15/08 604/514 |
| 2010/0076269 A1 | 3/2010 | Makower et al. | |
| 2010/0081873 A1* | 4/2010 | Tanimura | A61B 1/00096 600/109 |
| 2010/0099946 A1* | 4/2010 | Jenkins | A61B 1/0014 600/104 |
| 2010/0100181 A1 | 4/2010 | Makower et al. | |
| 2010/0105983 A1 | 4/2010 | Oneda et al. | |
| 2010/0114066 A1 | 5/2010 | Makower et al. | |
| 2010/0114184 A1* | 5/2010 | Degtyar | A61B 17/1659 606/86 R |
| 2010/0121308 A1* | 5/2010 | Muni | A61B 5/411 604/514 |
| 2010/0152730 A1 | 6/2010 | Makower et al. | |
| 2010/0168511 A1 | 7/2010 | Muni et al. | |
| 2010/0174138 A1 | 7/2010 | Chang et al. | |
| 2010/0174196 A1* | 7/2010 | Ryan | A61B 5/0066 600/473 |
| 2010/0174308 A1 | 7/2010 | Chang et al. | |
| 2010/0179488 A1* | 7/2010 | Spiegel | A61M 16/044 604/240 |
| 2010/0179511 A1* | 7/2010 | Rajan | A61M 11/00 604/514 |
| 2010/0198135 A1 | 8/2010 | Morriss et al. | |
| 2010/0198191 A1 | 8/2010 | Clifford et al. | |
| 2010/0198247 A1 | 8/2010 | Chang et al. | |
| 2010/0210901 A1 | 8/2010 | Makower et al. | |
| 2010/0211005 A1 | 8/2010 | Edwards et al. | |
| 2010/0211007 A1* | 8/2010 | Lesch, Jr. | A61M 29/02 604/97.02 |
| 2010/0211140 A1* | 8/2010 | Barbut | A61F 7/12 607/105 |
| 2010/0217296 A1 | 8/2010 | Morriss et al. | |
| 2010/0241068 A1* | 9/2010 | Chen | A61M 1/3653 604/96.01 |
| 2010/0241155 A1* | 9/2010 | Chang | A61B 17/24 606/196 |
| 2010/0256653 A1 | 10/2010 | Kaplan et al. | |
| 2010/0268245 A1 | 10/2010 | Chang et al. | |
| 2010/0274188 A1 | 10/2010 | Chang et al. | |
| 2010/0274222 A1 | 10/2010 | Setliff et al. | |
| 2010/0280626 A1* | 11/2010 | Shalon | A61F 2/04 623/23.64 |
| 2010/0282246 A1 | 11/2010 | Djupesland et al. | |
| 2010/0286659 A1* | 11/2010 | Terrill | A61D 7/00 604/514 |
| 2010/0292765 A1 | 11/2010 | Etwil | |
| 2010/0298640 A1 | 11/2010 | Oneda et al. | |
| 2010/0298862 A1 | 11/2010 | Chang et al. | |
| 2010/0305697 A1 | 12/2010 | Clifford et al. | |
| 2010/0324483 A1* | 12/2010 | Rozenberg | A61M 16/0461 604/98.01 |
| 2011/0004057 A1* | 1/2011 | Goldfarb | A61B 1/233 600/106 |
| 2011/0004058 A1 | 1/2011 | Oneda et al. | |
| 2011/0004192 A1 | 1/2011 | Eaton et al. | |
| 2011/0004194 A1 | 1/2011 | Eaton et al. | |
| 2011/0015645 A1 | 1/2011 | Liu et al. | |
| 2011/0015734 A1* | 1/2011 | Gonzales | A61B 17/24 623/10 |
| 2011/0020279 A1* | 1/2011 | Shantha | A61K 33/30 424/85.4 |
| 2011/0054395 A1* | 3/2011 | O'Dea | A61B 5/1076 604/97.02 |
| 2011/0060214 A1 | 3/2011 | Makower | |
| 2011/0087192 A1* | 4/2011 | Uhland | A61K 9/0036 604/514 |
| 2011/0098659 A1 | 4/2011 | Covello | |
| 2011/0112512 A1* | 5/2011 | Muni | A61B 17/24 604/514 |
| 2011/0152838 A1* | 6/2011 | Xia | A61M 11/06 604/514 |
| 2011/0160623 A1 | 6/2011 | Shalev | |
| 2011/0160740 A1 | 6/2011 | Makower et al. | |
| 2011/0208215 A1 | 8/2011 | Modesitt et al. | |
| 2011/0224652 A1 | 9/2011 | Drontle et al. | |
| 2011/0245765 A1* | 10/2011 | Jacobsen | A61B 1/05 604/95.02 |
| 2011/0288559 A1 | 11/2011 | Shahoian | |
| 2011/0318345 A1* | 12/2011 | Djupesland | A61K 9/0043 424/134.1 |
| 2012/0010646 A1 | 1/2012 | Keith et al. | |
| 2012/0017893 A1 | 1/2012 | Xia | |
| 2012/0046607 A1 | 2/2012 | Syk | |
| 2012/0053404 A1* | 3/2012 | Schreck | A61B 17/24 600/104 |
| 2012/0071715 A1* | 3/2012 | Beyar | A61F 2/958 600/104 |
| 2012/0071727 A1* | 3/2012 | Hanson | A61B 17/24 600/249 |
| 2012/0071824 A1 | 3/2012 | Chang et al. | |
| 2012/0071856 A1* | 3/2012 | Goldfarb | A61B 17/24 604/514 |
| 2012/0071857 A1* | 3/2012 | Goldfarb | A61B 17/24 604/514 |
| 2012/0078118 A1* | 3/2012 | Jenkins | A61B 5/065 600/478 |
| 2012/0078377 A1 | 3/2012 | Gonzales et al. | |
| 2012/0089028 A1 | 4/2012 | Hadani et al. | |
| 2012/0090620 A1* | 4/2012 | Deutsch | A61M 1/0009 128/207.15 |
| 2012/0101343 A1* | 4/2012 | Duffy | A61B 5/489 600/249 |
| 2012/0116254 A1 | 5/2012 | Morriss | |
| 2012/0128683 A1* | 5/2012 | Shantha | A61K 38/08 424/141.1 |
| 2012/0136207 A1 | 5/2012 | Goldfarb et al. | |
| 2012/0157968 A1 | 6/2012 | Eldredge et al. | |
| 2012/0172751 A1 | 7/2012 | Levin | |
| 2012/0172835 A1 | 7/2012 | Becker | |
| 2012/0184983 A1 | 7/2012 | Chang et al. | |
| 2012/0220923 A1 | 8/2012 | Morriss et al. | |
| 2012/0221034 A1 | 8/2012 | Dinger et al. | |
| 2012/0227457 A1 | 9/2012 | Kim et al. | |
| 2012/0245419 A1 | 9/2012 | Makower et al. | |
| 2012/0245456 A1 | 9/2012 | Kim et al. | |
| 2012/0259215 A1 | 10/2012 | Gerrans et al. | |
| 2012/0259216 A1* | 10/2012 | Gerrans | A61B 1/00165 600/435 |
| 2012/0265094 A1* | 10/2012 | Goldfarb | A61B 1/0014 600/562 |
| 2012/0277578 A1* | 11/2012 | Gunday | A61B 17/22012 600/424 |
| 2012/0302825 A1 | 11/2012 | Schaeffer et al. | |
| 2012/0310145 A1 | 12/2012 | Clifford et al. | |
| 2012/0323214 A1* | 12/2012 | Shantha | A61N 1/30 604/501 |
| 2013/0006055 A1* | 1/2013 | Goldfarb | A61B 1/00066 600/137 |
| 2013/0018431 A1 | 1/2013 | Levin | |
| 2013/0030458 A1* | 1/2013 | Drontle | A61M 29/02 606/196 |
| 2013/0041463 A1 | 2/2013 | Ressemann | |
| 2013/0053644 A1 | 2/2013 | Smith et al. | |
| 2013/0053822 A1* | 2/2013 | Fischell | A61M 25/0084 604/510 |
| 2013/0053824 A1* | 2/2013 | Seiden | A61B 17/24 604/514 |
| 2013/0066358 A1* | 3/2013 | Nalluri | A61F 11/002 606/199 |
| 2013/0072958 A1* | 3/2013 | Ressemann | A61B 17/24 606/199 |
| 2013/0073015 A1* | 3/2013 | Rozenberg | A61F 7/0085 607/106 |
| 2013/0085472 A1 | 4/2013 | Shaari | |

(56) References Cited

U.S. PATENT DOCUMENTS

| | | |
|---|---|---|
| 2013/0090544 A1 | 4/2013 | Clifford et al. |
| 2013/0096605 A1 | 4/2013 | Becker |
| 2013/0103023 A1 | 4/2013 | Monson et al. |
| 2013/0123833 A1* | 5/2013 | Lesch .................. A61M 29/02 606/196 |
| 2013/0130145 A1 | 5/2013 | Kaeding et al. |
| 2013/0158475 A1* | 6/2013 | Xia .................. A61M 39/1011 604/94.01 |
| 2013/0165873 A1 | 6/2013 | Morriss et al. |
| 2013/0172852 A1 | 7/2013 | Chang |
| 2013/0184532 A1 | 7/2013 | Goldfarb et al. |
| 2013/0184568 A1 | 7/2013 | Muni et al. |
| 2013/0184574 A1* | 7/2013 | Newhauser, Jr. ...... A61B 17/24 600/431 |
| 2013/0184683 A1* | 7/2013 | Chow .................. A61B 17/24 604/514 |
| 2013/0190678 A1 | 7/2013 | Andreas et al. |
| 2013/0197426 A1 | 8/2013 | Morriss et al. |
| 2013/0231529 A1 | 9/2013 | John et al. |
| 2013/0245608 A1* | 9/2013 | Muni .................. A61B 17/24 604/514 |
| 2013/0245609 A1 | 9/2013 | Schaeffer et al. |
| 2013/0261388 A1 | 10/2013 | Jenkins et al. |
| 2013/0274600 A1* | 10/2013 | Jenkins .................. A61B 1/07 600/431 |
| 2013/0274651 A1* | 10/2013 | Barbut .................. A61M 31/00 604/26 |
| 2013/0274715 A1* | 10/2013 | Chan .................. A61M 25/10 604/514 |
| 2013/0276794 A1 | 10/2013 | Morriss |
| 2013/0281982 A1 | 10/2013 | Makower et al. |
| 2013/0302445 A1* | 11/2013 | Barbut .................. A61K 9/0043 424/700 |
| 2013/0303968 A1 | 11/2013 | Clifford et al. |
| 2013/0324970 A1* | 12/2013 | Arcand .................. A61B 17/24 604/514 |
| 2013/0325052 A1 | 12/2013 | Chang et al. |
| 2014/0012182 A1 | 1/2014 | Shantha |
| 2014/0018775 A1* | 1/2014 | Swords .................. A61M 11/00 604/514 |
| 2014/0030520 A1 | 1/2014 | Nakamura et al. |
| 2014/0031726 A1 | 1/2014 | Chernomorsky et al. |
| 2014/0031792 A1 | 1/2014 | Darin et al. |
| 2014/0066901 A1 | 3/2014 | Dinger et al. |
| 2014/0066928 A1 | 3/2014 | Bennett et al. |
| 2014/0073858 A1 | 3/2014 | Sherwinter |
| 2014/0074065 A1 | 3/2014 | Muni et al. |
| 2014/0074140 A1* | 3/2014 | Johnson .......... A61M 25/10182 606/192 |
| 2014/0074141 A1* | 3/2014 | Johnson .................. A61M 29/00 606/192 |
| 2014/0088498 A1 | 3/2014 | Stevens et al. |
| 2014/0094733 A1 | 4/2014 | Clopp et al. |
| 2014/0107404 A1* | 4/2014 | Gruber .................. A61B 1/303 600/37 |
| 2014/0107427 A1* | 4/2014 | Chow .................. A61B 17/24 600/249 |
| 2014/0114233 A1* | 4/2014 | Deem .................. A61K 38/4886 604/20 |
| 2014/0135587 A1* | 5/2014 | Hess .................. A61B 17/4241 600/249 |
| 2014/0163072 A1* | 6/2014 | Romon-de-Jesus ... A61K 45/06 514/330 |
| 2014/0180328 A1* | 6/2014 | Vaccaro .................. A61M 29/02 606/196 |
| 2014/0200443 A1* | 7/2014 | Chang .................. A61B 17/1204 600/424 |
| 2014/0200444 A1 | 7/2014 | Kim et al. |
| 2014/0213968 A1* | 7/2014 | Vaccaro .......... A61M 25/10182 604/97.03 |
| 2014/0218904 A1 | 8/2014 | Cayton |
| 2014/0238398 A1* | 8/2014 | Christopher ...... A61M 16/0816 128/204.22 |
| 2014/0242064 A1* | 8/2014 | Morriss .................. A61K 9/0043 424/94.67 |
| 2014/0243792 A1 | 8/2014 | Berman et al. |
| 2014/0243793 A1* | 8/2014 | Morriss .................. A61M 15/085 604/514 |
| 2014/0243876 A1* | 8/2014 | Suehara .................. A61M 29/02 606/196 |
| 2014/0276624 A1* | 9/2014 | Jeppson .................. A61M 3/0262 604/514 |
| 2014/0276626 A1* | 9/2014 | Jenkins .................. A61M 29/02 604/514 |
| 2014/0276627 A1* | 9/2014 | Jenkins .................. A61M 1/0058 604/514 |
| 2014/0277072 A1* | 9/2014 | Suehara .................. A61M 29/02 606/196 |
| 2014/0288623 A1 | 9/2014 | Levin |
| 2014/0295728 A1* | 10/2014 | Cayton .................. F21S 10/02 446/220 |
| 2014/0296898 A1 | 10/2014 | Chang et al. |
| 2014/0324093 A1 | 10/2014 | Chang et al. |
| 2014/0330074 A1 | 11/2014 | Morriss et al. |
| 2014/0336575 A1 | 11/2014 | Muni et al. |
| 2014/0336693 A1 | 11/2014 | Goldfarb et al. |
| 2014/0336694 A1 | 11/2014 | Becker |
| 2014/0350520 A1 | 11/2014 | Drontle et al. |
| 2015/0038901 A1 | 2/2015 | Lampropoulos et al. |
| 2015/0039014 A1* | 2/2015 | Schaeffer .................. A61B 17/24 606/199 |
| 2015/0045825 A1* | 2/2015 | Caplan .................. A61M 25/04 606/191 |
| 2015/0065872 A1* | 3/2015 | Drake .................. A61M 5/007 600/432 |
| 2015/0065995 A1* | 3/2015 | Sanchez ........... A61B 17/12136 604/514 |
| 2015/0141819 A1* | 5/2015 | Linden .................. A61M 5/46 600/434 |
| 2015/0141915 A1* | 5/2015 | Lampropoulos A61M 25/10182 604/97.03 |
| 2015/0164309 A1* | 6/2015 | Chandler .................. A61B 17/24 600/249 |
| 2015/0164571 A1* | 6/2015 | Saadat .................. A61B 17/24 600/109 |
| 2015/0173592 A1* | 6/2015 | Leeflang .................. A61B 17/3478 600/106 |
| 2015/0174406 A1* | 6/2015 | Lamensdorf ........ A61N 1/36057 607/62 |
| 2015/0196735 A1* | 7/2015 | Olig .................. A61M 25/0074 604/514 |
| 2015/0196753 A1* | 7/2015 | Levin .................. A61K 9/0043 607/46 |
| 2015/0230700 A1* | 8/2015 | Chandler .................. A61B 1/0684 600/116 |
| 2015/0258315 A1* | 9/2015 | Chandler ........ A61M 25/10182 600/249 |
| 2015/0352341 A1* | 12/2015 | Chandler ........ A61M 25/10182 600/249 |
| 2016/0135671 A1 | 5/2016 | Chandler et al. |
| 2016/0271375 A1* | 9/2016 | Chandler ........ A61M 25/10182 |
| 2017/0246434 A1* | 8/2017 | Chandler ........ A61M 25/10182 |

FOREIGN PATENT DOCUMENTS

| | | |
|---|---|---|
| EP | 2522586 A2 | 11/2012 |
| KR | 20050117277 A | 12/2005 |
| KR | 1020050117277 A | 4/2006 |
| KR | 1020120013930 A | 2/2012 |
| WO | 2002005703 A1 | 1/2002 |
| WO | 2002007632 A1 | 1/2002 |
| WO | 2006020180 A2 | 2/2006 |
| WO | 2010078145 A1 | 7/2010 |
| WO | 2015095214 A1 | 6/2015 |

OTHER PUBLICATIONS

Borris, et al., "Intraoperative nasal transillumination for maxillary sinus augmentation procedures: A technical note," International

(56) References Cited

OTHER PUBLICATIONS

Journal of Oral and Maxillofacial Implants, vol. 13, Issue 4 (Jul.-Aug. 1998), pp. 569-570 (abstract only).
Cohen, et al., "Transnasal Illumination to Guide the Craniofacial Resection of Anterior Skull Base Neoplasms," Surgical Neurology, vol. 40 (1993), pp. 420-423.
Dolor, et al., "Management of Rhinosinusitis in Adults: Clinical Applications of Recent Evidence and Treatment Recommendations," Journal of Clinical Outcomes Management, vol. 9, No. 8 (Aug. 2002), pp. 463-476.
Felisati, "Headache & Migraine; Sphenopalatine endoscopic ganglion block alleviates cluster headache symptoms," Life Science Weekly (Oct. 10, 2006), pp. 741.
Friedman, et al., "Intraoperative and Postoperative Assessment of Frontal Sinus Patency by Transillumination," The Laryngoscope, vol. 110 (Apr. 2000), pp. 683-684.
Hung, et al., "Lightwand intubation: II—Clinical trial of a new lightwand for tracheal intubation in patients with difficult airways," Canadian Journal of Anaesthesia, vol. 42, Issue 9 (1995), pp. 826-830.
International Search Report and Written Opinion issued in PCT/US2014/070642, dated Apr. 9, 2015, 16 pages.
International Search Report and Written Opinion issued in PCT/US2014/070905, dated Apr. 24, 2015, 15 pages.
Massengill, "An Objective Technique for Submucous Cleft Palate Detection," Plastic and Reconstructive Surgery, vol. 37, No. 4 (1966), pp. 355-359.
Miyazaki, et al., "Fiberscopic Methods for Assessment of Velopharyngeal Closure during Various Activities," presented at the 15th annual convention of the Japan Society of Oral Surgery in Nagoya, Oct. 1970; presented at the 25th annual convention of the Japan Society of Oral Medicine in Tokyo, Apr. 1971; and presented at the 2nd International Cleft Palate Congress in Copenhagen, Aug. 1973.
Petroianu, et al., "Intubation with Transillumination: Nasal or Oral?," Prehospital and Disaster Medicine, vol. 14, No. 2 (Apr.-Jun. 1999), pp. 72-73.
U.S. Appl. No. 14/298,521 entitled Method of Performing a Sphenopalatine Ganglion Block Procedure, filed Jun. 6, 2014.
U.S. Appl. No. 14/572,353 entitled Surgical Device for Performing a Sphenopalatine Ganglion Block Procedure, filed Dec. 16, 2014.
U.S. Appl. No. 14/669,999 entitled Stabilized Surgical Device for Performing a Sphenopalatine Ganglion Block Procedure, filed Apr. 29, 2015.
U.S. Appl. No. 14/712,722 entitled Method of Performing a Sphenopalatine Ganglion Block Procedure, filed May 14, 2015.
U.S. Appl. No. 15/008,115 entitled Method of Performing a Sphenopalatine Ganglion Block Procedure, filed Jan. 27, 2016.
U.S. Appl. No. 29/512,059 entitled Surgical Device, filed Dec. 16, 2014, 2015.
WelchAllyn® 3.5v Transilluminators product brochure, date unknown.
WelchAllyn® PocketScopes™ Operating Instruction Manual, date unknown.

* cited by examiner

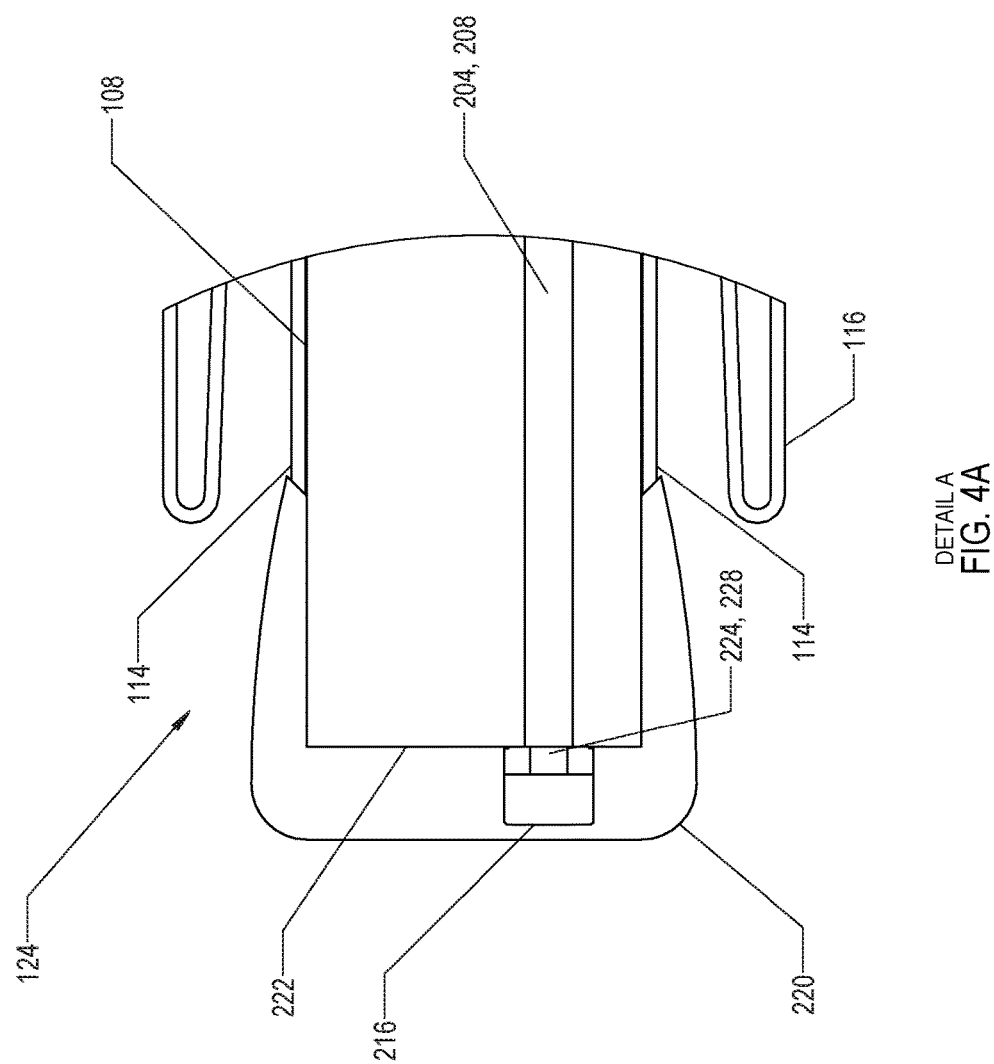

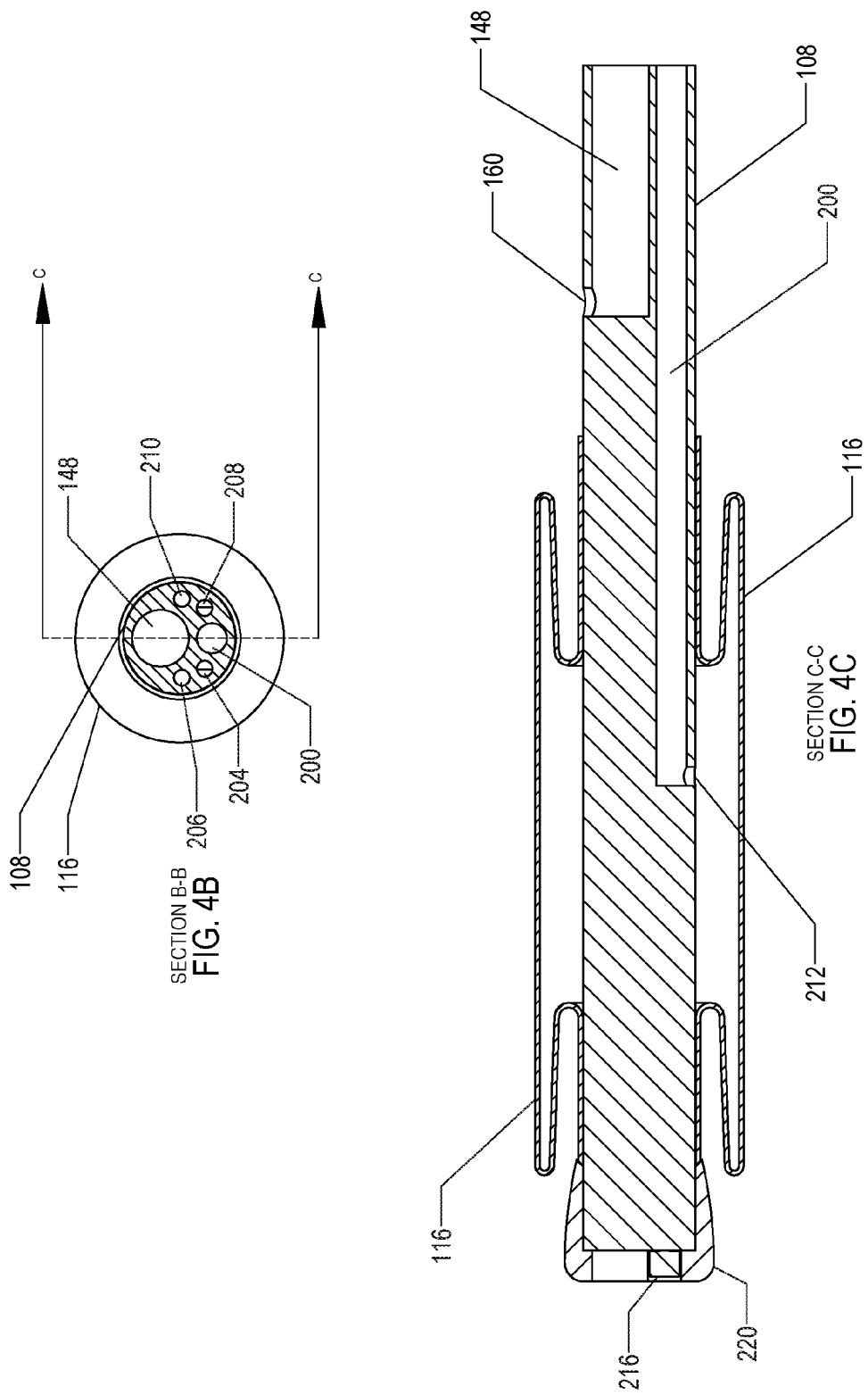

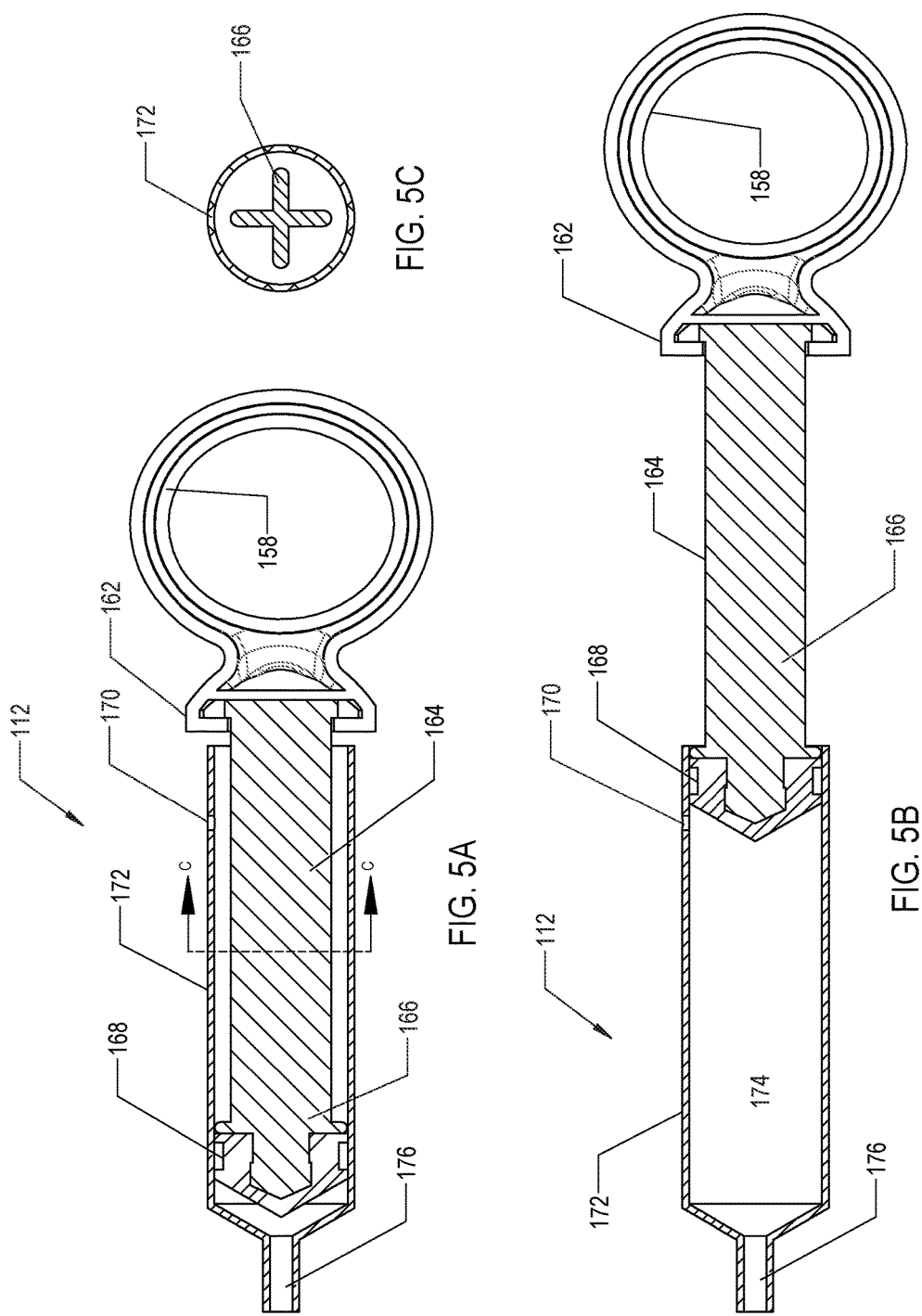

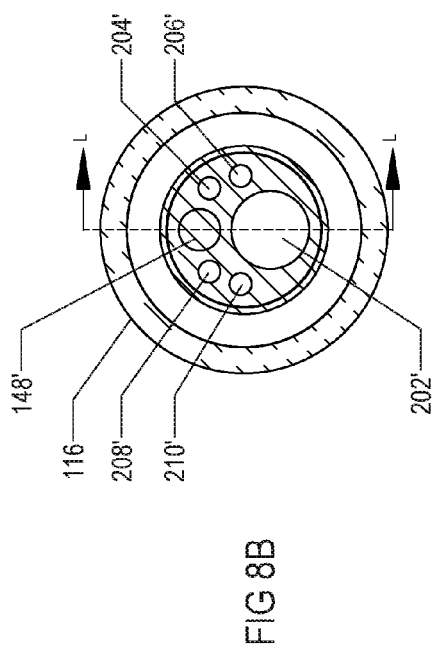
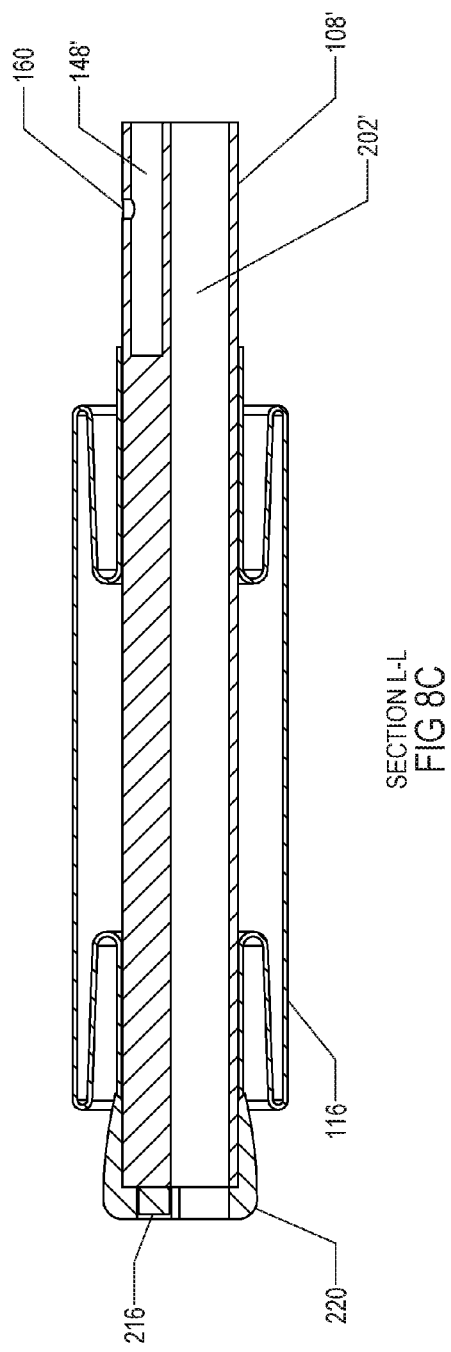

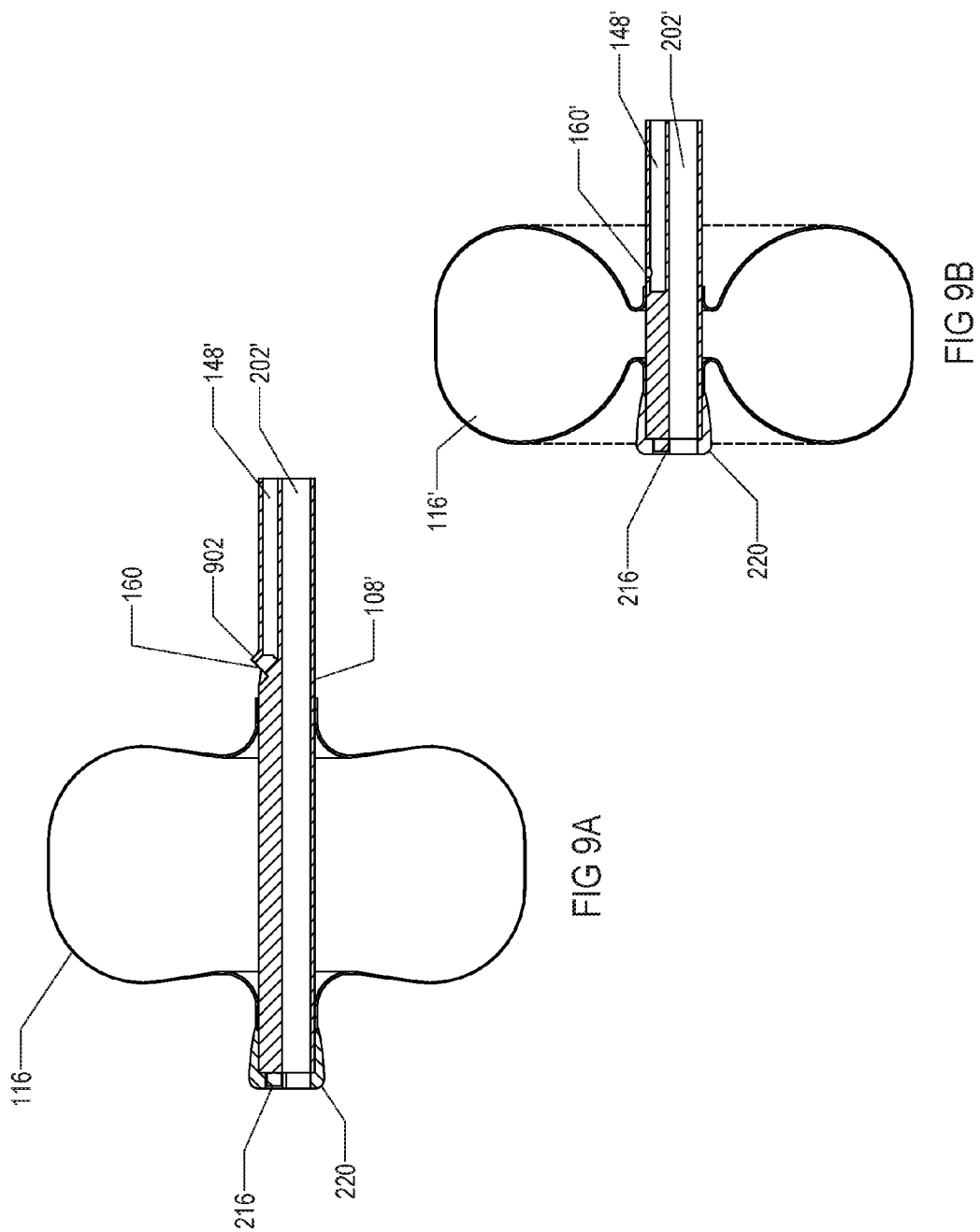

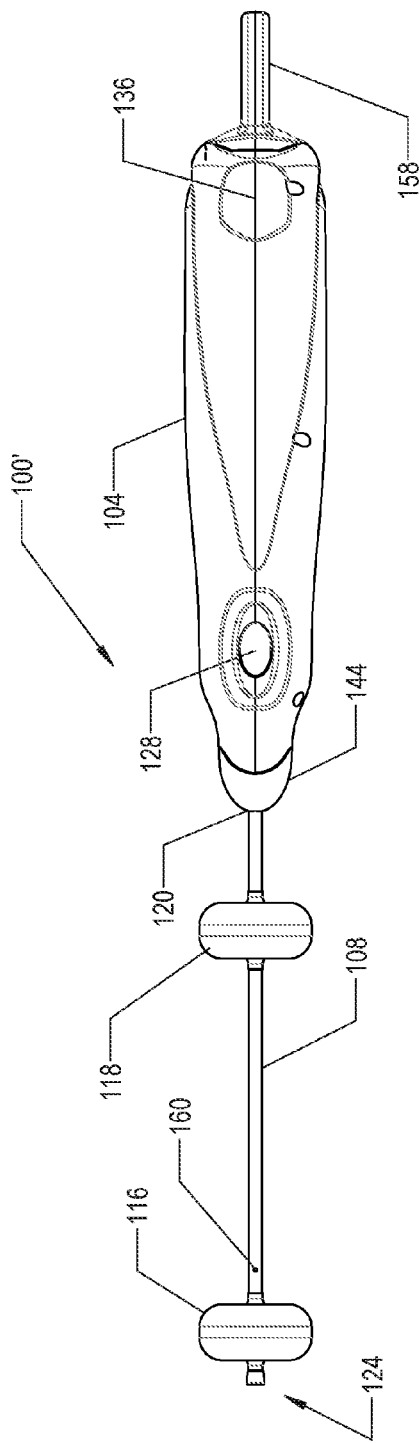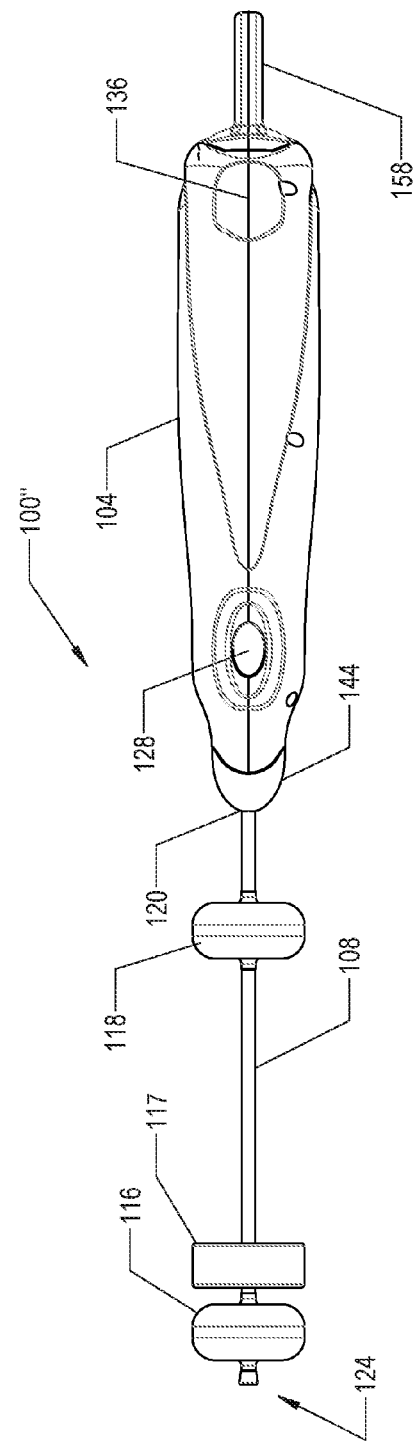
FIG. 10A
FIG. 10B

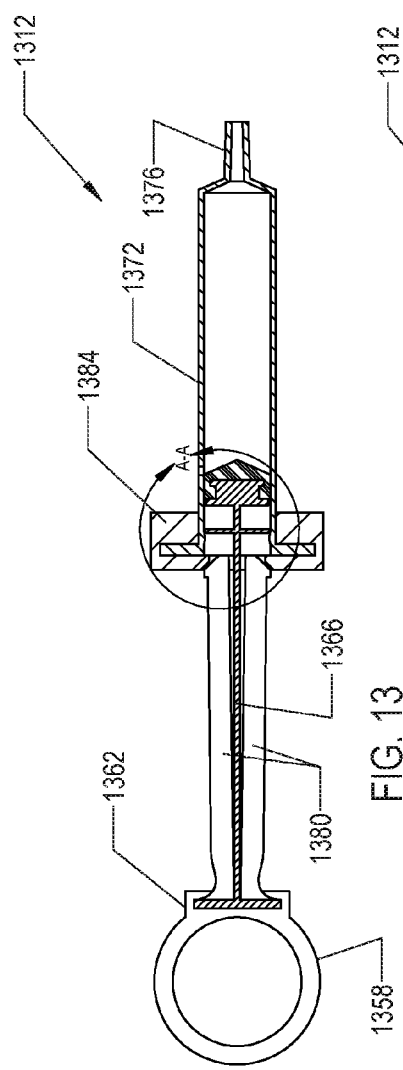
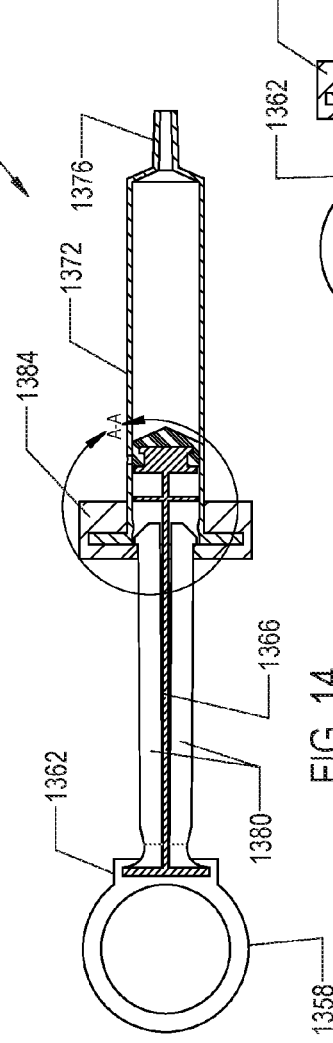
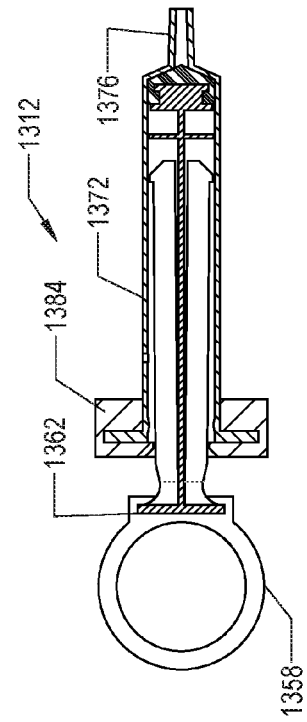
FIG. 13
FIG. 14
FIG. 15

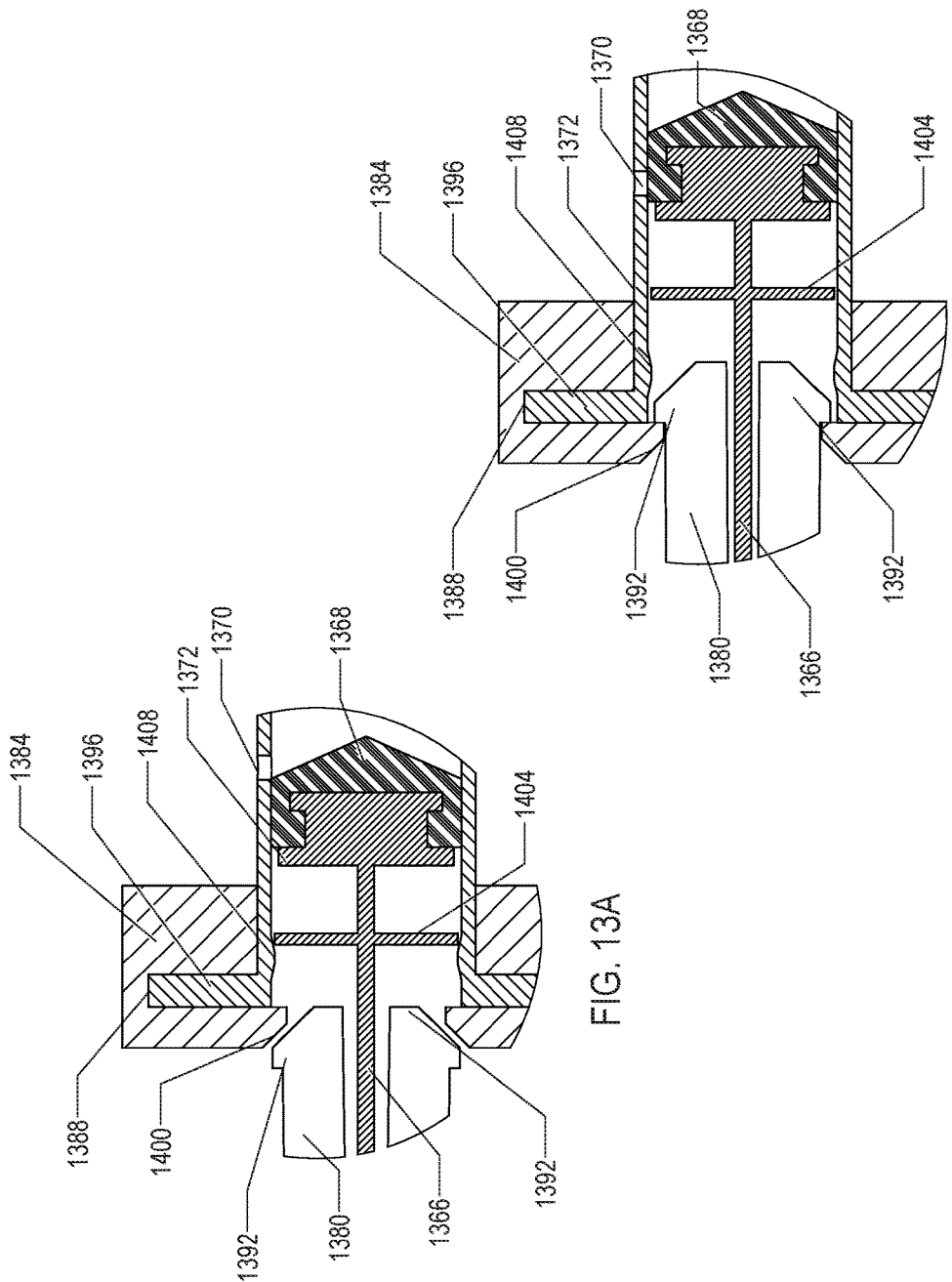

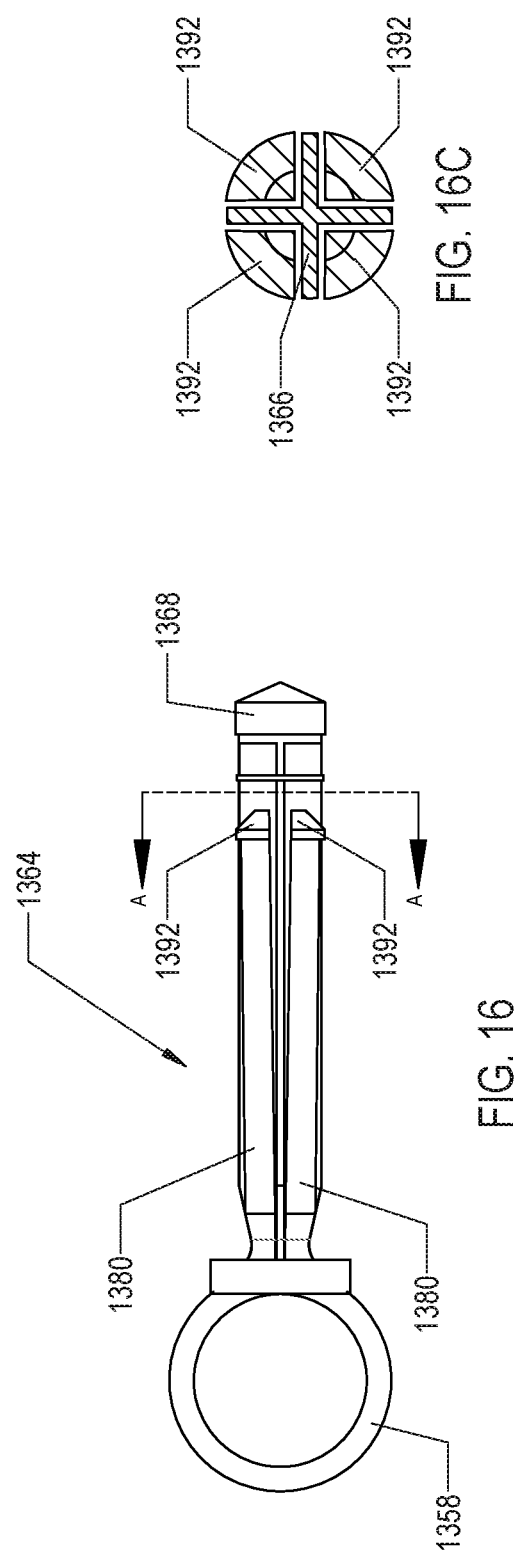

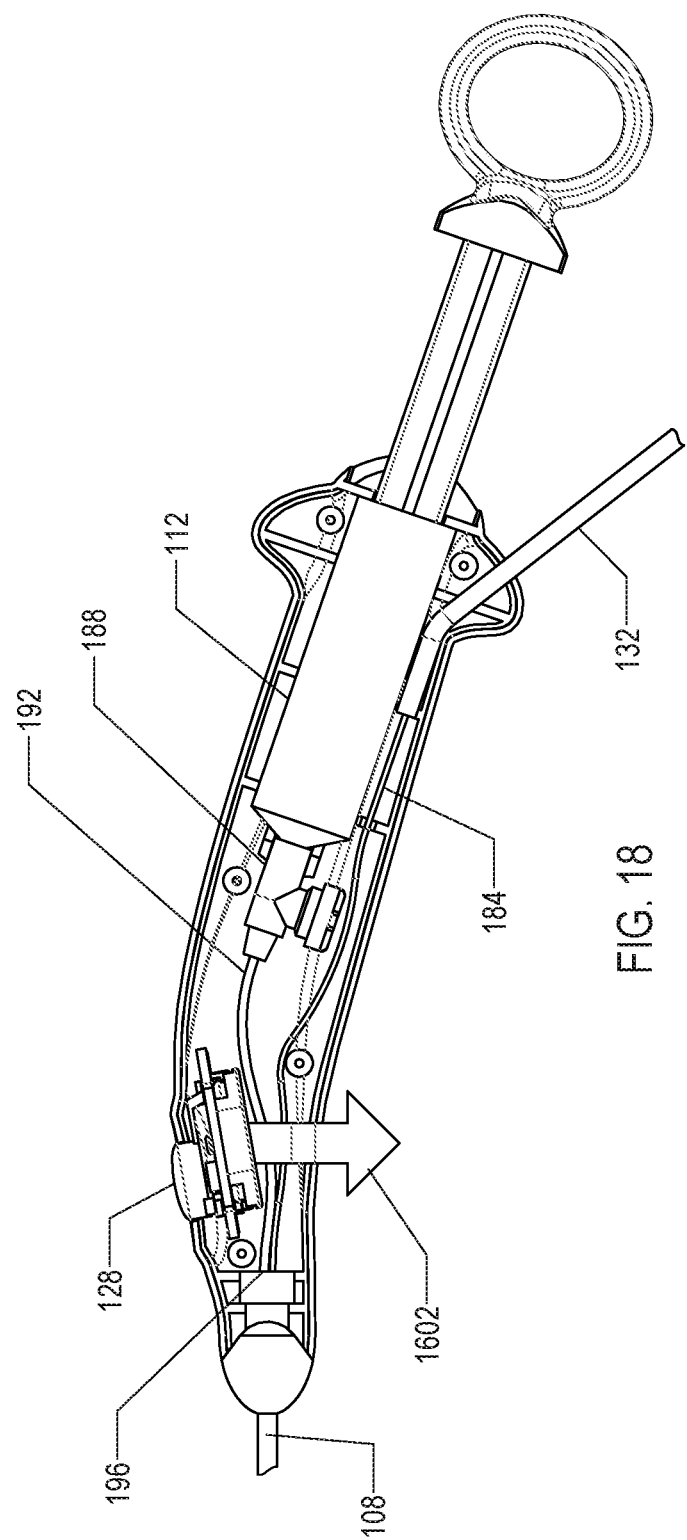

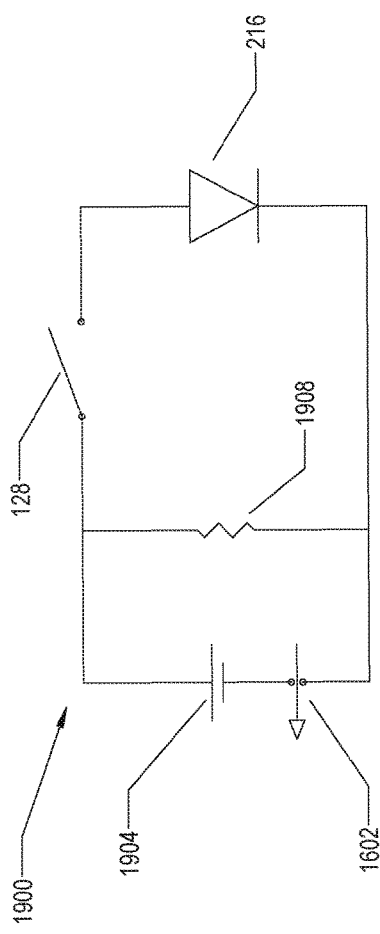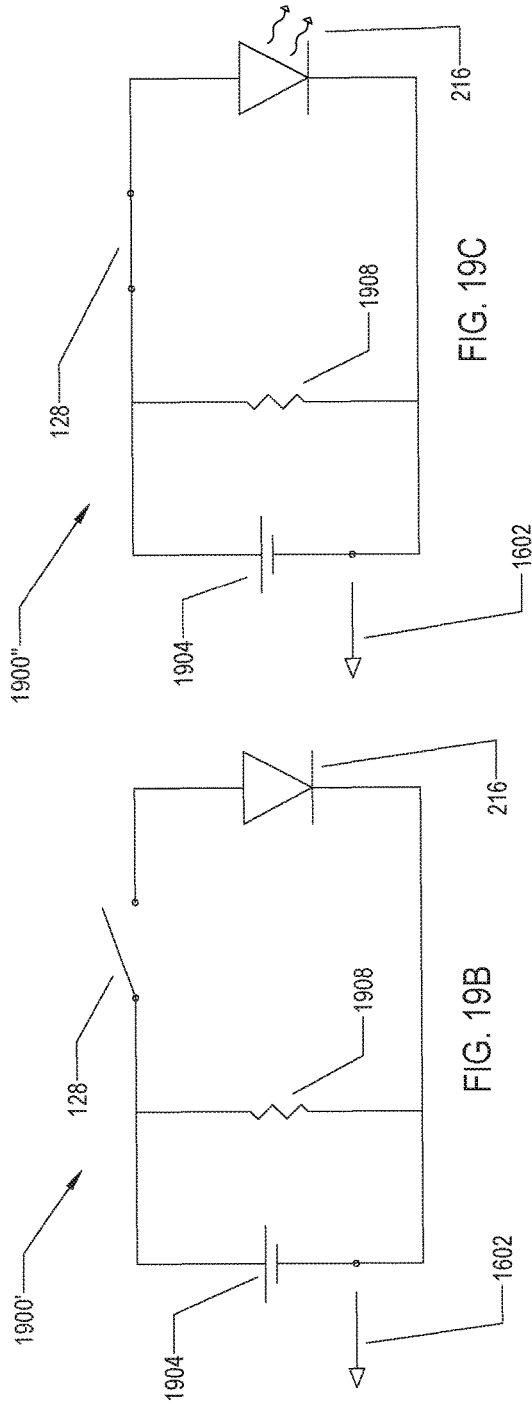

METHODS FOR TREATING SINUS DISEASES

CROSS REFERENCE TO RELATED APPLICATION

This patent application claims the benefit of and priority to, under 35 U.S.C. § 119(e), U.S. Provisional Application Ser. No. 62/168,505, filed May 29, 2016, entitled METHOD FOR TREATING SINUS DISEASES. The present application is also a Continuation-In-Part of U.S. application Ser. No. 14/699,999 filed Apr. 29, 2015 and entitled STABILIZED SURGICAL DEVICE FOR PERFORMING A SPHENOPALATINE GANGLION BLOCK PROCEDURE, which claims the benefit of and priority to Continuation-In-Part of U.S. application Ser. No. 14/572,353 filed Dec. 16, 2014 and entitled SURGICAL DEVICE FOR PERFORMING A SPHENOPALATINE GANGLION BLOCK PROCEDURE, which claims the benefit of and priority to Continuation-In-Part of U.S. application Ser. No. 14/298,521 filed Jun. 6, 2014 and entitled SURGICAL DEVICE FOR PERFORMING A SPHENOPALATINE GANGLION BLOCK PROCEDURE, which claims the benefit of and priority to, under 35 U.S.C. § 119(e), U.S. Provisional Application Ser. No. 61/917,097, filed Dec. 17, 2013, entitled APPARATUS, SYSTEM, AND METHOD FOR TREATING HEADACHES. All of these patent applications are hereby incorporated herein by reference in their entireties for all that they teach and for all purposes. The present application is also related to commonly assigned, U.S. application Ser. No. 14/712,722, filed on May 14, 2015, now issued as U.S. Pat. No. 9,248,266, and commonly assigned co-pending U.S. application Ser. No. 15/008,115, filed on Jan. 27, 2016, which are hereby incorporated herein by reference in their entirety for all that they teach and for all purposes.

FIELD OF THE DISCLOSURE

The present disclosure relates generally to devices, methods and systems for treating sinus diseases, and more specifically, to devices, such as a surgical device, and methods for using such device, for delivering medication to sinus cavities.

BACKGROUND

Paranasal sinuses are cavities formed within the bones of the face that are accessible via an individual's nasal cavity. The paranasal sinuses include the frontal sinuses, the sphenoid sinuses, the ethmoid sinuses, and the maxillary sinuses. The paranasal sinuses are lined with mucous-producing epithelial tissue.

Normally, mucous produced by the linings of the paranasal sinuses slowly drains out of each sinus through an opening known as an ostium. Some conditions, however, can interfere with the drainage of the mucous. If the mucous does not drain properly or other abnormal anatomic variations exist, sinus disorders (e.g., a sinus infection) can result. Some of the conventional systemic methods for treating these sinus disorders can result in cutaneous rash, diarrhea, bacterial resistance from antibiotic use, adrenal suppression, weight gain from steroid medications, hypertension, and sleep disturbance from decongestant use.

SUMMARY

Methods for treating sinus disease via application of a medication to the infected sinus can avoid some of the side-effects listed above that are inherent in systemic treatment. However, the introduction of medication via a transnasal route may result in a large majority of the medication flowing down the individual's throat, resulting in possible aspiration. Additionally, the medication is typically distasteful, which further exacerbates the unpleasantness.

Accordingly, there is a need for a device, method and/or system, such as a surgical device, that has the capability to quickly and accurately apply medication to a paranasal sinus, as well as prevent the medication applied to a paranasal sinus from flowing down a patient's throat. The present disclosure discusses a method and device that satisfies such needs.

The method may include delivering a medication to a portion of a paranasal sinus of a patient comprising the steps of inserting a device into a nasal cavity of a patient through a nostril, wherein the device comprises a handle comprising a proximal end and a distal end, an inflation device at least partially and integrally disposed within the handle, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and as distal end, wherein the inflation lumen opens into the expandable member, wherein the port is disposed proximally of the proximal end of the expandable member, and an illumination device disposed adjacent the distal end of the flexible tubular member and distally of the expandable member, and activating the illumination device, placing the expandable member adjacent the patient's choana, expanding the expandable member adjacent the patient's choana, introducing an amount of medication into the nasal cavity, such that at least a portion of the medication can enter an ostium of a paranasal sinus of the patient, removing at least a portion of the medication from the port in the flexible tubular member, collapsing the expandable member, and removing the device from the nasal cavity.

A device in accordance with this disclosure for may include a handle comprising a proximal end and a distal end, an inflation device at least partially and integrally disposed within the handle, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and as distal end, wherein the inflation lumen opens into the expandable member, wherein the port is disposed proximally of the proximal end of the expandable member, and an illumination device disposed adjacent the distal end of the flexible tubular member and distally of the expandable member.

The device may also or alternatively include a switch on the handle for activating the illumination device.

The device may also or alternatively include a pressure relief valve disposed within the handle and coupled to the plunger and the inflation lumen.

Accordingly, another device for delivering a medication to a patient in accordance with this disclosure may comprise a handle comprising a proximal end and a distal end, an inflation device at least partially and integrally disposed within the handle, a flexible tubular member extending from the distal end of the handle, the flexible tubular member comprising a proximal end, a distal end, an inflation lumen extending from the proximal end, a second lumen extending from the proximal end to a port disposed proximally of the distal end of the flexible tubular member, an expandable member attached to the flexible tubular member, wherein the inflation lumens opens into the expandable member, wherein the port is disposed proximally of the expandable member, and a pressure relief valve disposed within the handle and coupled to the plunger and the inflation lumen.

An alternative device in accordance with this disclosure may include a handle comprising a proximal end and a distal end, an inflation device at least partially and integrally disposed within the handle, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and as distal end, wherein the inflation lumen opens into the expandable member, wherein the port is disposed proximally of the proximal end of the expandable member, an illumination device disposed adjacent the distal end of the flexible tubular member and distally of the expandable member, a temporary power supply disposed within the handle, and a means for depleting the power supply within a predetermined time.

The temporary power supply for the device may include a battery. The means for depleting the power supply in a predetermined time may include a circuit having a second circuit path in parallel with a first circuit path for the illumination device. The device may also or alternatively include a pull tab for interrupting the circuit, thereby creating an open circuit for either or both the first circuit path and the second circuit path.

An alternative device in accordance with this disclosure may include a handle comprising a proximal end and a distal end, an inflation device at least partially and integrally disposed within the handle, the inflation device comprising a plunger and a barrel, the barrel comprising a wall forming a chamber and an opening through the wall, the plunger comprising a seal and one or more locking arms having a length, whereupon the locking arms being disposed proximally and exterior of the barrel, the seal is disposed within the chamber proximally of the opening, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and as distal end, wherein the inflation lumen opens into the expandable member, wherein the port is disposed proximally of the proximal end of the expandable member, and an illumination device disposed adjacent the distal end of the flexible tubular member and distally of the expandable member.

The device may also or alternatively include locking arms disposed in the chamber and adjacent a proximal orifice of the barrel while the seal is disposed within the chamber adjacent or distal the opening. The device may also or alternatively include locking arms being disposed in the chamber and distal of a proximal orifice of the barrel while the seal is disposed within the chamber distal the opening.

An alternative device in accordance with this disclosure may include a handle comprising a proximal end and a distal end, an inflation device at least partially disposed within the handle, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and a distal end, wherein the inflation lumen opens into the expandable member, an illumination device disposed adjacent the distal end of the flexible tubular member and distally of the expandable member, and a stabilizer slidably coupled to the flexible tubular member, wherein the stabilizer is capable of sliding along the flexible tubular member between the handle and the expandable member.

The device may also or alternatively be designed such that the stabilizer comprises a lumen, wherein the flexible tubular member is slidably disposed within the lumen, which has a proximal end and a distal end. The stabilizer may also or alternatively be compressible such that it has an uncompressed state and a compressed state. Additionally, the distal end of lumen within the stabilizer may also an oval cross-sectional profile when the stabilizer is in the uncompressed state a circular cross-sectional profile when the stabilizer is in the uncompressed state or vice versa.

The stabilizer may also or alternatively be configured such that the stabilizer is compressible. When the flexible tubular member is disposed in the lumen and the stabilizer is able to slide relative to the flexible tubular member, the stabilizer is able to slide over the flexible tubular member when the stabilizer is in a compressed state and is prevented from sliding over and relative to the flexible tubular member when the stabilizer is in an uncompressed state. The sliding of the stabilizer relative to the flexible tubular member is potentially made possible by the size of the circumference of the lumen being greater than the size of the circumference of the flexible tubular member during such sliding action, regardless of whether the stabilizer is in its compressed state or its uncompressed state, thereby insuring that the stabilizer can slide relative to the flexible tubular member. Accordingly, the stabilizer may be prevented from sliding over the flexible tubular member when one or more portions of the lumen contacts one or more portions the flexible tubular member, which may occur when the stabilizer is in an uncompressed state because portions of the oval shaped lumen contact the flexible tubular member. That is, when the stabilizer is in an uncompressed state it is unable to slide over the flexible tubular member due to the frictionally contact between the stabilizer and the flexible tubular member.

An alternative method in accordance with this disclosure may include inserting a device into a portion of a nasal cavity of a patient through a nostril, the device comprising a handle comprising a proximal end and a distal end, an inflation device at least partially disposed within the handle, a flexible tubular member extending from the distal end of the handle, the flexible tubular member comprising a proximal end, a distal end, an inflation lumen coupled to the plunger and extending from the proximal end of the flexible tubular member, and a second lumen extending from the proximal end of the flexible tubular member to a port, an expandable member attached to the flexible tubular member, the expandable member comprising a proximal end and a distal end, wherein the inflation lumen opens into the expandable member, wherein the port is disposed proximally of the proximal end of the expandable member, an illumination device disposed adjacent the distal end of the flexible tubular member and distally of the expandable member, and a stabilizer slidably coupled to the flexible tubular member, wherein the stabilizer is capable of sliding along the flexible tubular member between the handle and the expandable member, activating the illumination device, placing the expandable member adjacent the patient's choana, expanding the expandable member adjacent the patient's choana, sliding the stabilizer adjacent the patient's nose, introducing a medication to sphenopalatine ganglion through the port in the flexible tubular member, removing at least a portion of the medication through the port in the flexible tubular member, collapsing the expandable member sliding the stabilizer distal the patient's nose, and removing the device from the nasal cavity.

The device used in this method may also be used again by inserting the device into a second portion of the nasal cavity of the patient through a second nostril and performing same steps performed on the second nostril as those steps were performed on the first nostril.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "compressed state" shall mean a state of an object upon being squeezed, compacted, and/or condensed or the like. And the term "uncompressed state" shall mean a state of an object when it is not squeezed, compacted, and/or condensed or the like.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "medication" shall mean a substance used for medical treatment, such as a medicine or drug or remedy having in a specified formulation. The medicinal substance may also be referred to as a medicament. For the purposes of this disclosure a medication shall include anesthetics, including but not limited to local anesthetics, general anesthetics and/or the combination thereof. Examples of local anesthetics include, but are not limited to the following: amylocaine; ambucaine; articaine; benzocaine; benzonatate; bupivacaine; butacaine; butanilicaine; chloroprocaine; cinchocaine; cocaine; cyclomethycaine; dibucaine; diperodon; dimethisoquin; dimethocaine (larocaine); eucaine; etidocaine; hexylcaine; hydroxyprocaine; Isobucaine; levobupivacaine; lidocaine (lignocaine); mepivacaine; meprylcaine; metabutoxycaine; orthocaine; oxetacaine (oxethazaine); oxybuprocaine (benoxinate); paraethoxycaine; phenacaine; piperocaine (metycaine); piridocaine; pramocaine (pramoxine); prilocaine; primacaine; procaine; procainamide; proparacaine (proxymetacaine); propoxycaine; pyrrocaine; quinisocaine (dimethisoquin); ropivacaine; trimecaine; tetracaine (amethocaine); tolycaine; and tropacocaine. Examples of other drugs may include neurotoxins, such as botulinum toxin, including botulinum toxin type A, which may include onabotulinumtoxinA, abobotulinumtoxinA, and incobotulinumtoxinA, and botulinum toxin type B, which may include rimabotulinumtoxinB. In different embodiments, the medication can be in different forms. Examples include, but are not limited to, the following: foam, micelle, liquid, viscous aqueous, lipophilic agent, an aerosol and an atomized medicament. Additionally, an example medicament can include, but is not limited to, the following: antibiotics (e.g., macrolide, beta-lactam, amino glycoside, fluorinated quinolone, bactericidal or bacteriostatic classification) and anti-inflammatory agents (e.g., steroid anti-inflammatory, non-steroid anti-inflammatory, anti-metabolite, anti-fungal, and anti-viral preparations).

The term "transillumination" shall mean the transmission of light through body tissue, such as the palate (including both the soft palate and hard palate).

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4A is an enlarged cross-sectional view of the distal end of the elongated flexible tubular member distal of the expandable member of the surgical device depicted in FIG. 4;

FIG. 4B is a cross-sectional end view of the elongated flexible tubular member of the surgical device depicted in FIG. 4 taken along line B-B;

FIG. 4C is a cross-sectional side view of the elongated flexible tubular member depicted in FIG. 4B taken along line C-C;

FIG. 5A is a cross-sectional view of the plunger located within the handle of the surgical device depicted in FIG. 4D, wherein the plunger is illustrated in an extended position;

FIG. 5B is a cross-sectional view of the plunger located within the handle of the surgical device depicted in FIG. 4D, wherein the plunger is illustrated in a retracted position;

FIG. 5C is a cross-sectional view of the syringe depicted in FIG. 5A;

FIG. 8B is a cross-sectional end view of an alternative embodiment of the elongated flexible tubular member of the surgical device depicted in FIG. 4 taken along line B-B;

FIG. 8C is a cross-sectional side view of the elongated flexible tubular member depicted in FIG. 8B taken along line C-C;

FIG. 9A is a cross-sectional side view of an alternative embodiment of the elongated flexible tubular member depicted in FIG. 8C with the expandable member depicted in the expandable state;

FIG. 9B is a cross-sectional side view of another alternative embodiment of the elongated flexible tubular member depicted in FIG. 8C with the expandable member depicted in the expandable state;

FIG. 10A is a top view of an alternative embodiment of the surgical device depicted in FIGS. 1-4;

FIG. 10B is a top view of another alternative embodiment of the surgical device depicted in FIGS. 1-4;

FIG. 13 is a cross-sectional view of an alternative embodiment of the syringe illustrated in a retracted position during shipment;

FIG. 13A is an enlarged a cross-sectional view of the embodiment of the syringe of FIG. 13, wherein the plunger is illustrated in a retracted position during shipment; in an extended position;

FIG. 14 is a cross-sectional view of an alternative embodiment of the syringe illustrated in an initially retracted position during shipment and/or prior to use;

FIG. 14A is an enlarged a cross-sectional view of an alternative embodiment of the syringe of FIG. 14, wherein the plunger is illustrated in an initially retracted during shipment and/or prior to use;

FIG. 15 is a cross-sectional view of an alternative embodiment of the plunger illustrated in an extended position;

FIG. 16 is a side view of the plunger of the alternative embodiment of the syringe depicted in FIG. 13;

FIG. 16A is a cross-sectional view of the plunger in FIG. 16, wherein the locking arms, particularly the distal ends of the locking arms, are in a fully radially outward extended position relative to the shaft portion of the plunger;

FIG. 16B is a cross-sectional view of the plunger in FIG. 16, wherein the locking arms, particularly the distal ends of the locking arms, are in a fully radially inward position relative to the shaft portion of the plunger;

FIG. 16C is a cross-sectional view of the plunger in FIG. 16, wherein the locking arms, particularly the distal ends of the locking arms, are in a partially radially outward extended position relative to the shaft portion of the plunger;

FIG. 18 is a cross-sectional view of the alternative embodiment of the handle of the surgical device depicted in FIG. 17;

FIG. 19A is an illustration of a schematic of a circuit wherein a pull tab is interrupting both paths of the circuit;

FIG. 19B is an illustration of a schematic of a circuit wherein the pull tab in FIG. 19A is omitted and therefore not interrupting the circuit, which includes one closes path and one open path;

FIG. 19C is an illustration of a schematic of a circuit wherein the pull tab in FIG. 19A is omitted and therefore not interrupting the circuit, which includes two closed paths;

Figure 1:
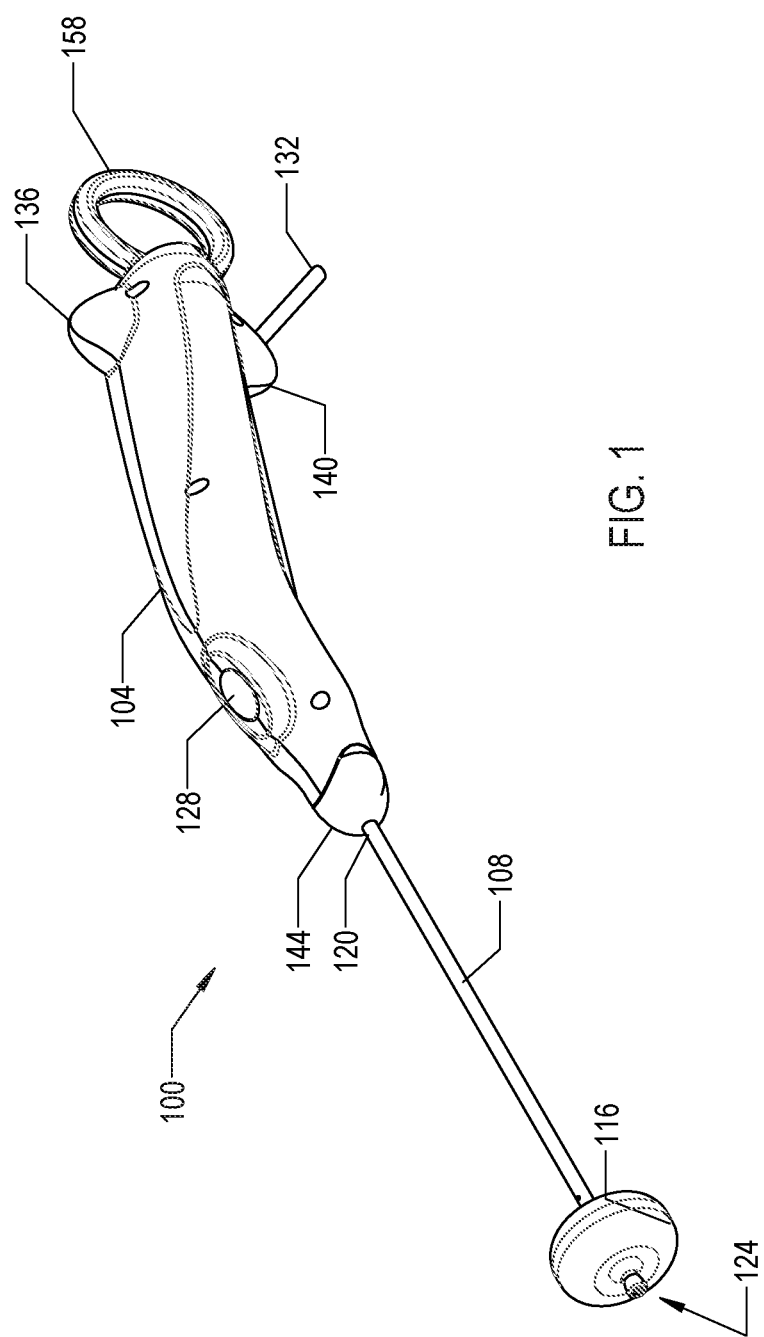
FIG. 1 is a perspective view of an embodiment of a surgical device of the present disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Embodiments according to this disclosure provide a surgical device that can be deployed safely within a nasal cavity of a patient and apply a medication, such as a local anesthetic, to the patient's sphenopalatine ganglion. FIG. 1-FIG. 4 depict a surgical device 100 having a handle 104 and an elongated flexible tubular member 108. The handle 104, which is ergonomically shaped, includes a proximal end and a distal end 144. The proximal end of the handle includes two projecting abutments 136, 140 so that the user's hand remains comfortably on the handle 104 during use and the user's hand does not slide off the handle 104. It may be preferable for the projecting abutments 136, 140 to be disposed on the top and bottom of the handle such that they are about 180 degrees opposed from one another, as illustrated in the FIGS. 1 & 2, or it may be preferable for the projecting abutments 136, 140 to be disposed in a different orientation with respect to the handle, such as on the sides of the handle 104. It may also be preferable to have less or more than two abutments. For example, it may be preferable to have a continuous abutment around the entire circumference of the handle 104 at or near its proximal end. As will be discussed in more detail below, when operating the handgrip or finger grip, such as a ring 158, the projecting abutments 136, 140 allow the clinician to ergonomically and comfortably depress and retract the barrel 172. For example, the clinician may insert his thumb in the ring 158 and locate his fingers on the distal side of the projecting abutments 136, 140 and depress the barrel 172 with one hand.

Figure 4:
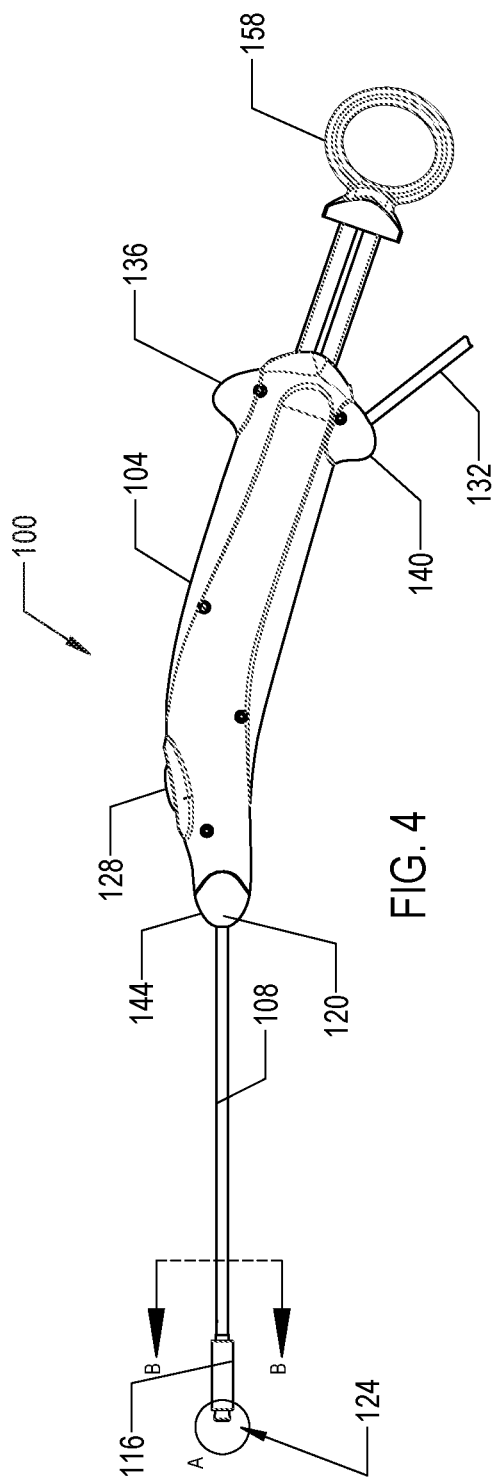
FIG. 4 is a side view of the surgical device depicted in FIG. 2.

As illustrated in FIG. 4, the handle 104 is curved. The proximal portion of the handle 104 has one longitudinal axis and the distal portion of the handle 104 has a different longitudinal axis. The longitudinal axis of the distal portion of the handle 104 may be offset at an angle of about 5 degrees about 60 degrees from the longitudinal axis of the proximal portion of the handle 104. It may be preferable for the offset angle to be about 10 degrees about 45 degrees and even more preferable for the offset angle to be about 20 degrees to about 30 degrees. The longitudinal axes of the proximal and distal portions of the handle 104 smoothly intersect, thereby creating a handle with a curved profile. The distal end 144 of the of the handle portion 104 may also have a rounded configuration, which is more ergonomic to engage the patient's nostril(s) upon insertion of the device 100, namely the elongated flexible tubular member 108, thereto.

Figure 2:
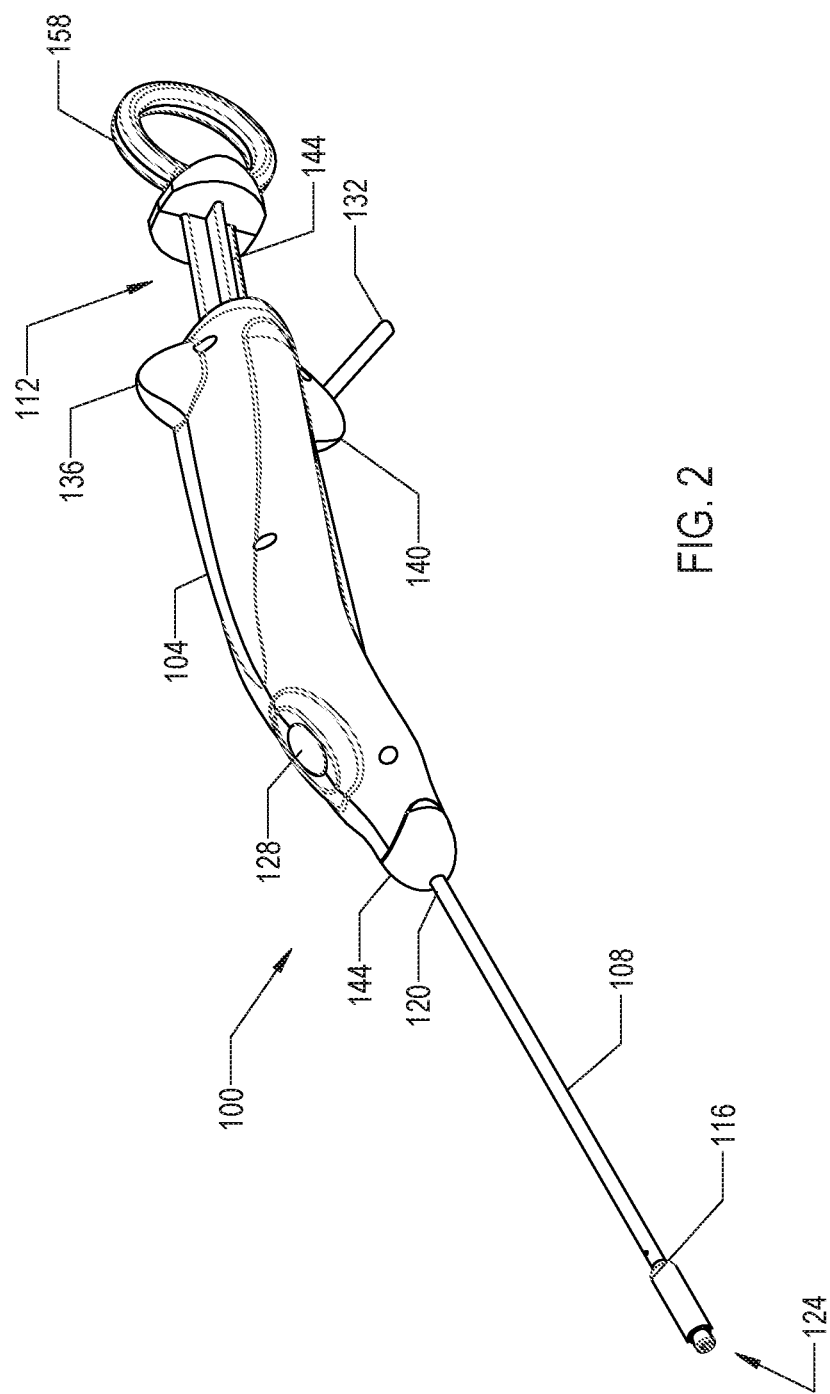
FIG. 2 is an alternate perspective view of the surgical device depicted in FIG. 1.
Figure 3:
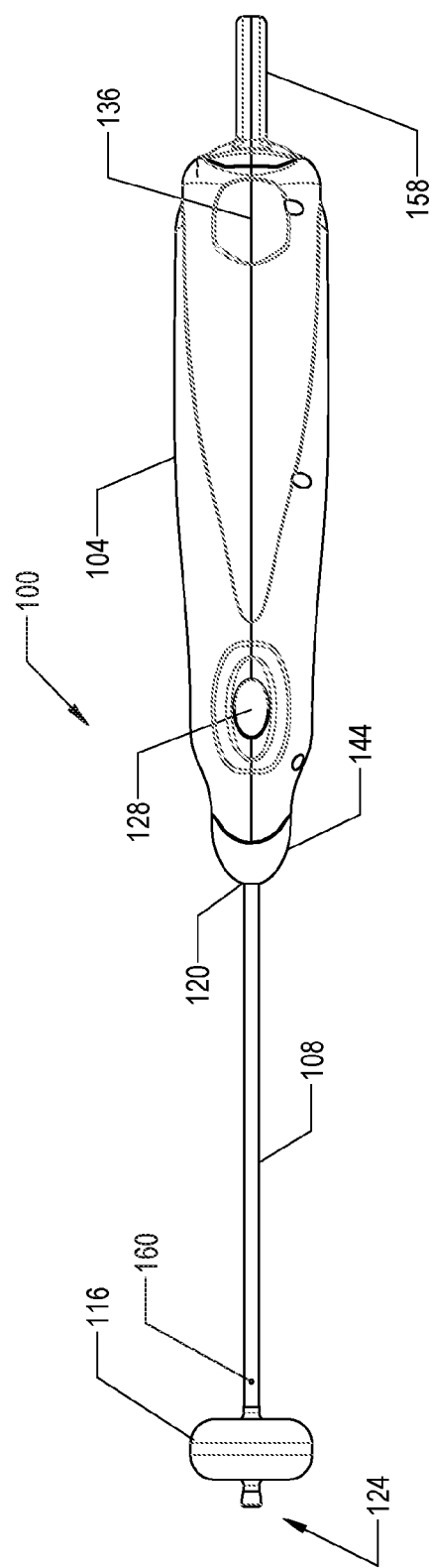
FIG. 3 is a top view of the surgical device depicted in FIG. 1.

The elongated flexible tubular member 108 includes a proximal end 120, which is attached to the distal end of the 144 of the handle 104. An expandable member 116, such as a balloon, is located at, adjacent to or toward the distal end 124 of the flexible tubular member 108. FIGS. 1 & 3 depict the expandable member 116 in an inflated state, and FIGS. 2 & 4 depict the expandable member 116 in a deflated state. The shape and size of the expandable member 116 may differ depending upon the patient's anatomy. For example, the size of the expandable member 116 may be smaller for children and larger for adults. It may be preferable for the expandable member 116 to have an inflated diameter of about 1 cm to 4 cm, with a possible preferential diameter of about 2.5 cm, and an inflated length of about 1 cm to 3, with a possible preferential inflated length of about 2.5 cm.

As discussed in more detail below, the handle 104 includes an inflation device, such as a syringe 112, integrated therein. The syringe 112 comprises a barrel 172, a plunger 164 at least partially disposed within the barrel 172, and a distal tip 176 at the end of the barrel 172. When the plunger 164 is depressed, the expandable member 116 is expanded (inflated) with fluid, such as air, and when the plunger 164 is retracted, the expandable member 116 is collapsed (deflated). It shall be understood that either a pneumatic inflation device, which utilizes air as the fluid, or a hydraulic inflation device, which utilizes liquid (e.g., saline, water, etc.) as the fluid, can be used.

The handle 104 also includes a switch 128 for activating an illumination device 216, such as a light-emitting diode (LED) disposed at or toward the distal end 124 of the elongated flexible tubular member 108. The switch 216 activates a power source, such as a battery, that is coupled to the illumination device 216 by two or more conductors (e.g., wires) 224, 228. The wires 224, 228 are disposed within lumens 224, 228 that travel from the proximal end to the distal end of the elongated flexible tubular member 108. As discussed above, the expandable member 116 is also disposed at or near or toward the distal end 124 of the elongated flexible tubular member 108. It is preferable for the illumination device 216 to be disposed distally of the expandable member 116 along the elongated flexible tubular member 108, thereby allowing the illumination device 216 to project light in a manner that is unobstructed by the expandable member 116. That is, it is preferable for the expandable member 116 to be disposed proximally of the illumination device 216 along the elongated flexible tubular member 108. For example, it may be preferable for the distal end of the expandable member 116 to be disposed about 0 to 1 mm and potentially even more preferable to be disposed at the distal end 124 of the elongated flexible tubular member 108.

An alternative illumination device 216 may include an illumination fiber (not shown) that is attached to and/or integral with the elongated flexible tubular member 108 such that the illumination fiber is exposed at the same location that the LED would have been disposed—at or toward the distal end 124 of the elongated flexible tubular member 108. The proximal end of the illumination is coupled to a light source that can be disposed interiorly and/or exteriorly of the handle 104. The light source can be powered by a direct current power source or an alternating current power source.

Referring to FIG. 4, there is depicted a side view of an embodiment of the surgical device 100 of the present disclosure. FIG. 4A is an enlarged cross-sectional view of the distal end 124 of the elongated flexible tubular member 108 illustrating a portion of the expandable member 116 in a deflated state. The distal end 124 of the elongated flexible tubular member 108 includes a cover 220 coupled to it. The cover 220 is constructed of a transparent material, such as polycarbonate. The cover 220 protects the illumination device 216. The cover 220 may also be shaped such that its edges are curved, thereby providing an atraumatic end to the surgical device. The cover 220 can be coupled directly to the distal face 222 of the elongated flexible tubular member 108 and/or it can be coupled to the perimeter of the distal end 124 of the elongated flexible tubular member 108. The tip 220 may preferably be coupled to the distal end 124 of the elongated flexible tubular member 108 by an adhesive compound. Alternative means of coupling the tip 220 to the distal end 124 of the elongated flexible tubular member 108 includes mechanical means, such as pressed fittings, snap on fittings, or a threaded arrangement between the tip 220 and the elongated flexible tubular member 108.

Continuing to refer to FIG. 4A, there is depicted an illumination device 216, which is also coupled to the distal face 222 of the elongated flexible tubular member 108 such that the illumination device projects light distally of the elongated flexible tubular member 108. Similar to tip 220, the illumination device 216 is coupled to the distal end 124 of the elongated flexible tubular member 108 by an adhesive. It may also be preferable for the tip 220 to surround at least a portion of the illumination device 216, thereby protecting the illumination device 216. The illumination device is powered by a power source, such as a battery, via one or more wires 224, 228 that couple the power source to the illumination device 216. The wires 224, 228 are disposed within lumens 224, 228 that travel from the proximal end to the distal end of the elongated flexible tubular member 108.

Referring to FIG. 4B, there is depicted a cross-sectional view of the elongated flexible tubular member 108 of the surgical device 100 depicted in FIG. 4 taken along line B-B. The elongated flexible tubular member 108 comprises a plurality of lumens. Although a different number of lumens may be used, FIG. 4B illustrates four lumens: lumen 148 is used to transport the medication to/from the medication port 160 located proximally of the expandable member 116; lumen 200 is used to transport fluid (e.g., air, water, saline, etc.) to/from the inflation port, which open into the expandable member 116; and two lumens 204, 208 provide channels for the wires 224, 228 to travel. All four lumens 148, 200, 204 & 208 have openings at the proximal end of the elongated flexible tubular member 108. Not all four lumens, however, may have openings at the distal end of the elongated flexible tubular member 108. For example, the lumen 148 used to transport the medication may have an opening at the proximal end of the elongated flexible tubular member 108 and an opening (or port) at 160 through the wall of the tubular member 108, which is located proximally of the expandable member 116. Additionally, the lumen 200 used to transport fluid to inflate the expandable member 116 may have a have an opening at the proximal end of the elongated flexible tubular member 108 and an opening (or port) at 212, which opens into the expandable member 116. Lumens 204, 208 may have an opening at the proximal end of the elongated flexible tubular member 108 and an opening at or near the distal end of the elongated flexible tubular member 108, thereby allowing the wires 224, 228 to travel all or the majority of the length of the elongated flexible tubular member 108 to the illumination device 216.

Alternatively, the elongated flexible tubular member 108 may not have lumens 204, 208. For example, if the elongated flexible tubular member 108 is constructed (e.g., molded) in a manner such that the wires 224, 228 are integral with the elongated flexible tubular member 108, then lumens 204, 208 may not be needed. Additionally, the elongated flexible tubular member 108 may have additional lumens 206, 210.

Figure 8A:
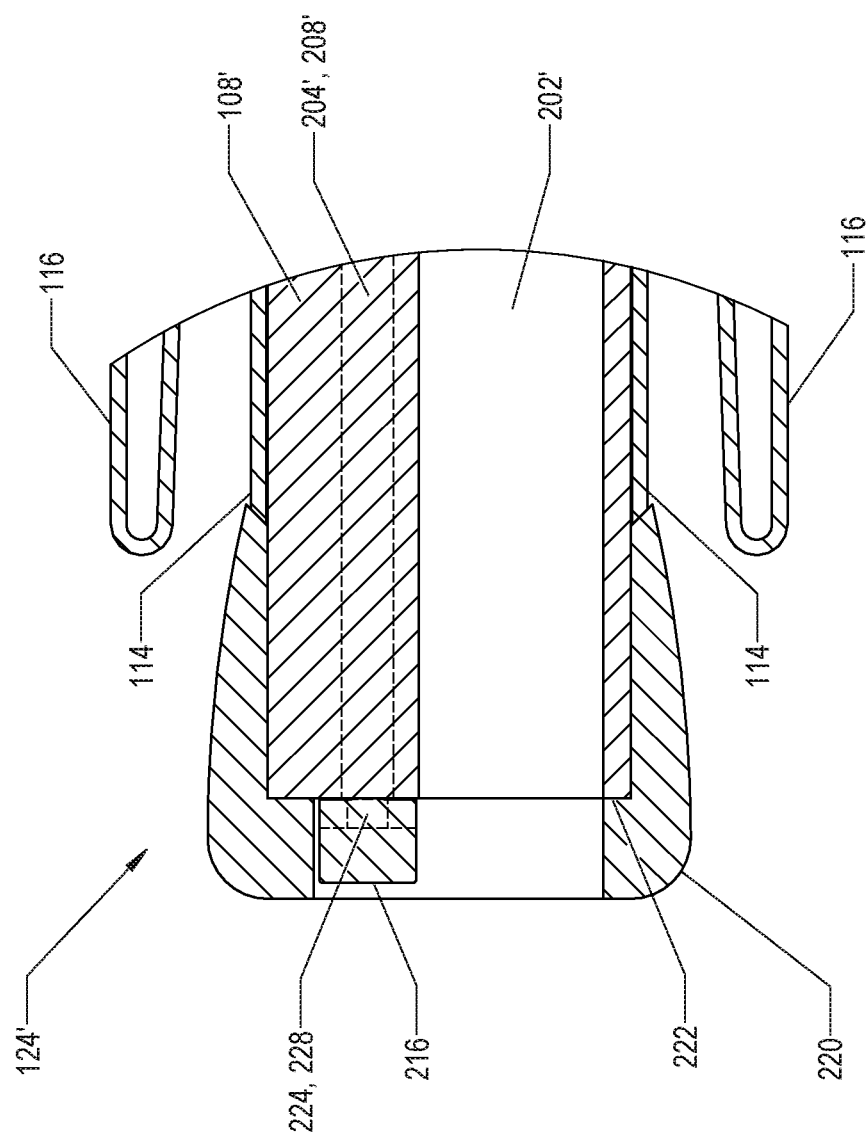
FIG. 8A is an enlarged cross-sectional view of an alternative embodiment of the distal end of the elongated flexible tubular member distal of the expandable member of the surgical device depicted in FIG. 4.

Another alternative embodiment may include an additional lumen in the elongated flexible tubular member 108 through which an imaging device may be inserted or incorporated. For instance, the surgical device 100 may include a reusable endoscope that is inserted through an opening (not shown) in the handle 104 and travels through the additional lumen in the elongated flexible tubular member 108 such that the endoscope is adjacent the illumination device 216 in the cover 220. Referring to FIGS. 8A, 8B & 8C, there is depicted such an alternative embodiment of the flexible tubular member 108' that includes lumen 202', which extends from the proximal end to the distal end of the flexible tubular member 108', and is configured to have an endoscope or other imaging device inserted thereto. Lumen 148' will be used to transport the medication to/from the medication port 160' located proximally of the expandable member 116; two lumens 204, 208 provide channels for the wires 224, 228 to travel to/from the illumination device 220; lumen 206' is used to transport fluid (e.g., air, water, saline, etc.) to/from the inflation port, which open into the expandable member 116; and lumen 208' is an additional lumen. Although it is not shown in the figures, it may also be desirable for the cover and/or the distal end of the flexible tubular member to have an optical divider that separates the light emitted by the illumination device from directly entering the endoscope or imaging device.

Regarding the placement of the opening 160 through the wall of the tubular member 108 for delivering the medication, it may be preferable for the opening 160 to be disposed about 1 mm to 10 mm from the proximal end of the expandable member 116 and possibly more preferably to be disposed about 2 mm to 5 mm from the proximal end of the expandable member 116. Locating the opening 160 through the wall of the tubular member 108 proximally of the proximal end of the expandable member 116 allows the medication to collect within the nasal cavity above the expandable member 116, while the expandable member 116 is inflated. It may be preferable for the medication to collect within the nasal cavity and form a pool of medication such that the level of medication rises to sphenopalatine fossa and/or the mucosa overlaying the SPG. Depending upon the size of the patient's nasal cavity, the volume of medication introduced to the nasal cavity and used to create such a pool may be between 2 milliliters to 15 milliliters, and potentially preferable for about 5 milliliters to 10 milliliters.

Figure 4D:
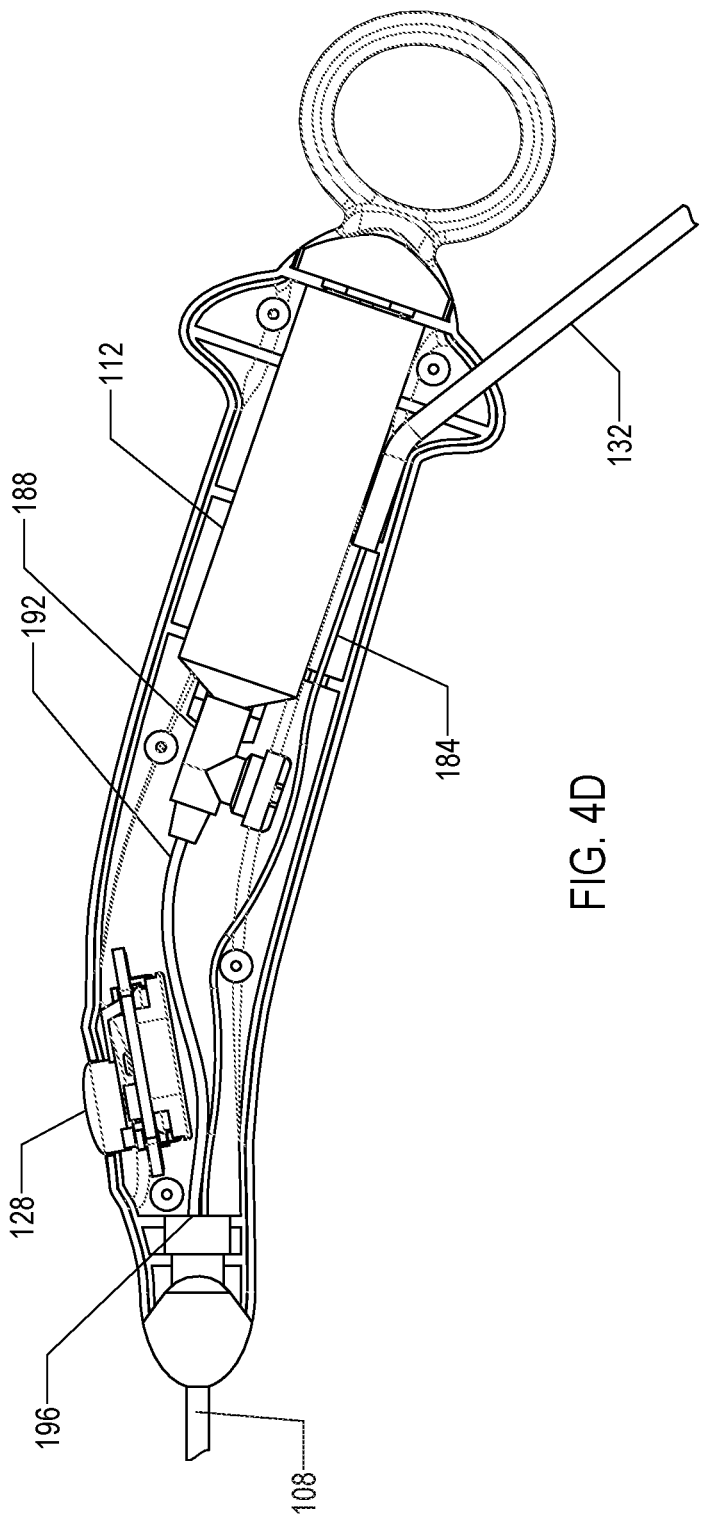
FIG. 4D is a cross-sectional view of the handle of the surgical device depicted in FIG. 4.

Referring to FIG. 4D, FIG. 5A. FIG. 5B and FIG. 5C, an inflation device, such as a syringe 112, is integrated into the handle 104. The syringe 112 is used to inflate and deflate the expandable member 116. Integrating the inflation device in the handle 104 reduces the likelihood of a clinician confusing which port(s) to connect the devices (i.e., syringes) used to introduce the medication and the inflation fluid. That is, by including an inflation device, such as the syringe 112, in the handle 104, a clinician will know and/or be instructed to use the integrated syringe 112 to inflate the expandable member 116 and an external syringe (not shown) to introduce the medication. Stated differently, a clinician will only have to introduce one fluid, namely the medication, through an external syringe, thereby reducing potential confusion as to which fluid to introduce and/or into which port. Alternatively, the syringe used to introduce the medication may be integrated into the handle 104 in lieu of the syringe 112 used to inflate and deflate the expandable member 116. A further alternative embodiment may include a handle 104 with two clearly marked integrated syringes—one syringe for the medication and another syringe for the inflation fluid.

The syringe 112 comprises a barrel 172, a plunger 164 at least partially disposed within the barrel 172, and a distal tip 176 having an opening at the distal end of the barrel 172. The plunger 164 has a shaft portion 166 and a proximal end 162 and distal end 168 at the respective ends of the shaft portion 166. A cross section of the shaft portion 166 is illustrated in FIG. 5C, which depicts the shaft portion 166 as having an "X" or "T" cross sectional profile. This cross sectional profile potentially increases the strength and rigidity of the shaft portion 166. The proximal end 162 and a distal end 168 may be coupled to the shaft portion 166 or be integrally formed thereto. The proximal portion 162 may also have a handgrip or finger grip, such as a ring 158, for a clinician to ergonomically and comfortably depress and retract the barrel 172. When the plunger 164 is depressed, the expandable member 116 is inflated, and when the plunger 164 is retracted, the expandable member 116 is deflated.

It may also be preferable for the barrel 172 to have an opening (port) 170 through the wall of the tubular member 108 adjacent, at or toward its proximal end. When the surgical device 100 is manufactured, it is assembled and/or packaged at a certain atmospheric pressure depending upon the geographic location of the manufacturing and/or packaging facility. The atmospheric pressure of the surgical site where the surgical device 100 is used, however, may be different than that at the manufacturing and/or packaging facility. Including the opening 170 through the wall of the barrel 172 allows the pressure within barrel to equalize with the pressure of the surgical site prior to use. It may also be preferable to ship the surgical device 100 in a configuration such that the plunger 164 is in a partially or fully retracted position such, thereby allowing the opening 170 to be located distally of the distal end 168 of the plunger 164. Shipping the surgical device in this configuration may enhance the time for the pressure within the chamber of the barrel to equalize with the atmospheric pressure at the surgical site more quickly.

During use of the surgical device 100, clinicians may also repeatedly depress and retract the plunger 164. Such repeated action has the potential to overinflate the expandable member 116. Inclusion of the opening 170 through the wall of the barrel 172 allows the pressure within barrel's chamber 174 to equalize with the atmospheric pressure upon retraction of the plunger 164, thereby reducing the likelihood of overinflating the expandable member 116. That is, upon depression of the plunger 164, the pressure within the chamber 174, as well as the pressure within the expandable member 116, increases above atmospheric pressure at the surgical site. Upon each retraction of the plunger 164, the pressure within the chamber 174, as well as the pressure within the expandable member 116, decreases back to atmospheric pressure prior to another depression of the plunger 164 because the fluid within the chamber 174 is vented to the atmosphere via the opening 170.

Venting the fluid within the chamber 174 also allows the expandable member 116 to deflate (or further deflate) upon application of pressure to the exterior of the expandable member 116. For example, upon retraction of the plunger 164, the pressure within the expandable member 116 may not immediately cause the expandable member 116 to completely deflate. That is, the expandable member 116 may retain a certain amount of fluid after retraction of the plunger, thereby allowing the expandable member 116 to remain partially inflated. Accordingly, when the surgical device 100, including the expandable member 116, is initially removed from the patient's nasal cavity, the expandable member 116 may be partially inflated. Inclusion of opening 170 within chamber 174 allows the expandable member 116 to further deflate upon removal of the surgical device 100, including the expandable member 116, from the patient's nasal cavity. Allowing the expandable member 116 to further deflate upon removal of the surgical device 100 assists in reducing the likelihood of the expandable member 116 causing discomfort to the patient.

Continuing to refer to FIG. 4D, a pressure relief valve 188 is disposed between the syringe 112 and the expandable member 116. Inclusion of the pressure relief valve 188 into the inflation circuit reduces the possibility of over pressurizing and over expanding the expandable member 116, particularly during a clinician's repeated depression and retraction of the plunger 164. The pressure relief valve 188 is a valve used to control or limit the pressure in a circuit, such as the inflation circuit. The pressure is relieved by allowing the pressurized fluid (e.g., air) to flow to an auxiliary passage, preferably in the valve, out of the circuit. The pressure relief valve is designed or set to open at a predetermined set pressure to protect the expandable member 116 from being subjected to pressures that exceed the desired clinical limits. When the set pressure is exceeded, the pressure relief valve is forced open and a portion of the fluid is diverted through the auxiliary route vented to the atmosphere. As the fluid is diverted, the pressure inside the circuit decreases. Once the pressure within the pressure relief valve reduces back to or below the predetermined set pressure, the valve will close. For example, the predetermined set pressure may be set between about 5 psi (0.345 bars) to 15 psi (1.034 bars) or possibly between about 8 psi (0.552 bars) to 12 psi (0.827 bars) or nominally about 10 psi (0.690 bars).

The pressure relief valve 188, particularly the proximal end of the pressure relief valve 188, is coupled to the distal tip 176 of the syringe 112. The distal end of the pressure relief valve 188 is, in turn, coupled to the tube 192 that is coupled to the inflation lumen 148 in the elongated flexible tubular member 108. Alternatively, the tube 192 may be omitted by directly coupling the distal end of the pressure relief valve 188 to the inflation lumen 148 in the elongated flexible tubular member 108.

Also disclosed herein is an alternative embodiment included within the surgical device 100 to accommodate for the change in atmospheric conditions that may exist between the manufacturing and/or packaging facility and the surgical site, while also reducing the likelihood of overinflating the expandable member 116. The embodiment of the syringe 1312 depicted in FIGS. 13-15 may negate the need for the inclusion of the pressure relief valve 18 discussed herein above. Referring to FIGS. 13 and 13A, as well as FIGS. 16, 16A, 16B and 16C, there is depicted an alternative embodiment of the syringe 1312 of the present disclosure. The syringe 1312 comprises a barrel 1372, and a plunger 1364 at least partially inserted within the barrel 1372. The plunger 1364 has a shaft portion 1366 and a proximal end 1362 and distal end 1368 at the respective ends of the shaft portion 1366. The barrel 1372 includes a distal tip 1376 having an opening at the distal end of the barrel 1372. The proximal end 1362 and a distal end 1368 of the plunger 1364 may be coupled to the shaft portion 1366 or be integrally formed thereto. The proximal portion 1362 may also have a handgrip or finger grip, such as a ring 1358, for a clinician to ergonomically and comfortably depress and retract the barrel 1372. When the plunger 1364 is depressed, the expandable member 116 is inflated, and when the plunger 1364 is retracted, the expandable member 116 is deflated due to the supply and removal of fluid through the inflation lumen 148.

Continuing to refer to FIGS. 13 and 13A, as well as FIGS. 16, 16A, 16B and 16C, the proximal end of the barrel 1372 may include a flange 1374 that is disposed within a flange recess 1388 of a housing 1384, which is coupled to the handle 104. Alternatively, the handle 104 may include an integral flange recess 1388 in which the flange 1374 may be disposed, thereby negating the need for a separate housing 1384. Regardless of whether the flange 1374 of the barrel 1372 is coupled to the handle 104 either indirectly by being disposed within the flange recess 1388 of the housing 1384, which is coupled to the handle 104, or directly to the handle 104, the barrel 1372 remains positionally fixed with respect to the handle 104 during shipment and use.

As discussed above with respect to FIGS. 5A & 5B, it may also be preferable for barrel 1372 of the syringe 1312 in FIGS. 13 and 13A to have an opening (port) 1370 through the wall of the barrel 1372 adjacent, at or toward its proximal end. Including an unobstructed opening 1370 within the proximal end, for example, of the barrel 1372 allows the pressure within the chamber of the barrel 1372 to equalize with the pressure of its current geographical location, such as the surgical site prior to use. It may also be preferable to ship the surgical device 100 in a configuration such that the plunger 1364 is in fully retracted position, thereby allowing the opening 1370 to be located distally of the distal end 1368 of the plunger 1364 and, therefore, unobstructed. Shipping the surgical device in this configuration allows the opening 1370 to be unobstructed by the plunger, thereby potentially decreasing the time for the pressure within the chamber of the barrel to equalize with the atmospheric pressure at the surgical site more quickly.

Continuing to refer to FIGS. 13 and 13A, there may be a need to insure that the distal end 1368, particularly the seal, of the plunger 1364 remains proximate the opening 1370 during shipment of the surgical device 100, thereby allowing the atmospheric pressure to enter into the chamber of the barrel 1372. It may be preferable, therefore, for the syringe 1312 to include means for preventing the distal end 1368, particularly the seal, of the plunger 1364 from moving distally of the opening 1370 in the barrel 1372 during shipment. One such means may include one or more locking arms 1380 coupled to the plunger 1364, wherein the locking arms 1380 have an unconstrained radially biased position that is greater than the orifice of the housing 1384. Referring to FIGS. 16, 16A, 16B and 16C, there is depicted four locking arms 1380 attached radially symmetrically around the shaft 1366 of the plunger 1364. Although four locking arms 1380 are illustrated in these figures, less than four (i.e., 1, 2 or 3) locking arms or greater than four (e.g., 5, 6, etc.) locking arms may be used. Each of the locking arms 1380 have a proximal end, which are coupled to the proximal end 1362 of plunger 1364, and a distal end 1392 extending therefrom. The locking arms 1380 are spring biased in a radially outward direction such that they flare radially outwards at their distal ends 1392 in comparison to their proximal ends.

It may also be preferable for the distal ends 1392 of the locking arms 1380 to include a male tapered portion which mates with a female tapered portion 1400 of the housing 1384. During shipment and prior to usage of the surgical device 100, the male tapered portion of the distal ends 1392 of the locking arms 1380 remains proximate the female tapered portion 1400 of the housing 1384. This is accomplished by the radially outward spring bias of the locking arms 1380 which causes the distal ends 1392, and particularly the male tapered portion, of the locking arms 1380 to have a configuration outside the chamber of the barrel 1372 such that the distal ends 1392 and/or the male tapered portion is biased outwardly to a diameter that is greater in diameter than the orifice of the housing, thereby causing the distal end 1392 and/or male tapered portion of the plunger 1364 to abut and contact the female tapered portion 1400 of the housing 1384. When the male tapered portion of the distal end 1392 of the plunger 1364 abuts and contacts the female tapered portion 1400 of the housing 1384, the seal 1368 is proximal of the opening 1370 within the barrel 1372. That is, the plunger 1364, particularly the shaft portion 1366 of the plunger 1364, has a predetermined length between the distal ends 1392 and/or the male tapered portions of the distal end 1392 of the locking arms 1380 and the seal 1368 such that when the surgical device is in its fully retracted position during shipment and prior to use, the seal 1368 has a length that is proximal of the opening 170, thereby allowing the chamber within the barrel 1372 to have the same pressure as the atmosphere for the geographic location of the surgical device. As will be discussed herein below, only upon a clinician manually forcing the plunger 1364 distally will the male tapered portion of the distal ends 1392 of the locking arms 1380 engage the female tapered portion 1400 of the housing 1384, thereby allowing the female tapered portion 1400 and the engagement with the male tapered portion of the distal ends 1392 of the locking arms 1380 to cause the distal ends 1392 of the locking arms 1380 to move radially inward and distally axial into orifice of the housing 1384 and the proximal end of the lumen within the barrel 1372.

Referring to FIG. 13A, it may also be preferable for the plunger, 1364 to include one or more cross sectional members 1404 having a circumference greater than a portion of lumen within the barrel. Such portion may have a reduced diameter at a ledge or ramp 1408 within the interior of the barrel's chamber. Such cross sectional members 1404 and ramp 1408 reduce the likelihood of the plunger 1364 from moving proximally out of the barrel 1372 during shipment.

Referring to FIGS. 14 and 14A, upon opening the package in which the surgical device 100 is shipped, the plunger 1364 is in its fully retracted position (or un-activated position). That is, during shipment and prior to use of the surgical device 100, the plunger 1364 is in its fully retracted position (or un-activated position). In order to prepare the surgical device 100 for use, the clinician may manually force the plunger 1364 axially in a distal direction such that the male tapered portion of the distal ends 1392 of the locking arms 1380 move radially inward upon contacting the female tapered portion 1400 of the housing 1384 and into the orifice of the housing 1384. After the male tapered portions of the distal ends 1392 of the locking arms 1380 move past the orifice of the housing 1384 and into the lumen of the barrel 1372, the resiliency of the locking arms 1380 forces the distal end 1392 of the locking arms 1380 to move radially outward. And because the lumen or chamber at the proximal end of the barrel 1372 is larger than the orifice of the housing 1384, the distal ends 1392 of the locking arms 1380 are allowed to move radially outward after moving axially past the orifice of the housing 1384 and into the chamber of the barrel 1372. The distal ends 1392 of the locking arms 1380 are flanged in comparison to at least a portion of the locking arms 1380 proximal thereto, thereby allowing the flanged portions of the distal ends 1392 of the locking arms 1380 to be adjacent and/or abut the interior of the ridge 1396 at the orifice of the housing 1384. Once the flanged portions of the distal ends 1392 and/or the of the locking arms 1380 move axially past the orifice of the housing 1384 and into the chamber of the barrel 1372, the plunger cannot be removed from the barrel, and the surgical device is in its initial partially retracted position (or activated position) and ready for use. When the surgical device is in its initial partially retracted position (or activated position) atmospheric pressure is prevented from entering into the chamber of the barrel 1372.

The length of the plunger 1364 is also designed such that, upon the distal end 1392 (including the flanged portion and male tapered portions) of the locking arms 1380 springing radially outward upon introduction into the lumen of the barrel 1372, the seal at the distal end 1368 of the plunger 1364 is disposed at or distally of the opening 170 in the barrel 1372. That is, the plunger 1364, particularly the shaft portion 1366 of the plunger 1364, has a predetermined length between the distal ends 1392 of the locking arms 1380 and the seal 1368 such that once the surgical device is in its initial partially retracted position and ready for use, the seal 1368 aligns with or is distal of the opening 170, thereby sealing the barrel's chamber. Sealing the opening 170 ensures that no additional fluid will enter the chamber and the initial pressure within the lumen of the barrel 1372 will be equal to that of the atmospheric pressure for the geographic location of the surgical device immediately after sealing.

Referring to FIG. 15, after the flanged portion of the distal end 1392 of the locking arms 1380 enters the housing 1384 and/or the barrel 1372, the clinician can push the plunger 1364 towards the distal end 1376 of the barrel 1372. When the plunger 1364 moves towards the distal end 1376 of the barrel 1372, the seal 1368 moves distally of the opening 1370, thereby increasing the fluid pressure within the barrel's chamber, inflation lumen, and expandable member 116, which is then inflated. That is, the plunger 1364, particularly the shaft portion 1366 of the plunger 1364, has a predetermined length between the distal ends 1392 of the locking arms and the seal 1368 such that once the surgical device moves in a axially distal direction from its partially retracted position, the seal 1368 is distal of the opening 170 within the barrel 1372, thereby continuing to seal the barrel's chamber. After the clinician pushes and extends the plunger distally, the clinician can then pull or retract the plunger 1364 such that it moves proximally. Due to the locking arms 1380 being in their sprung radially outward position, the clinician can only pull the plunger proximally to a position wherein the locking arms 1380 abut and/or are adjacent the interior of the ridge 1396 at the distal end of the orifice of the housing 1384, as illustrated in FIGS. 14 and 14A. Accordingly, the locking arms 1380 not only serve as a for preventing the distal end 1368, particularly the seal, of the plunger 1364 from moving distally of the opening 1370 in the barrel 1372 during shipment, but the locking arms 1380 also serve as a means for maintaining a sealed chamber during use of the surgical device.

During use of the surgical device 100, clinicians may repeatedly depress and retract the plunger 1364. Inclusion of the opening 1370 through the wall of the barrel 1372 allows the pressure within barrel's chamber 1374 reduces the likelihood of overinflating the expandable member 116 because prior to its use, the chamber 1374 is at atmospheric pressure for the geographical position at which the surgical device will be used. That is, upon depression of the plunger 1364, the pressure within the chamber 1374, as well as the pressure within the expandable member 116, increases above atmospheric pressure at the surgical site. Upon each retraction of the plunger 1364, the pressure within the chamber 1374, as well as the pressure within the expandable member 116, decreases back to atmospheric pressure prior to another depression of the plunger 1364 because no additional the fluid will enter the chamber 174 upon retraction.

When the plunger 1364 is in a position within the barrel 1372 such that the male tapered portions of the distal ends 1392 of the locking arms 1380 are proximal and/or abuts the female tapered portion 1400 of the housing 1384, as illustrated in FIGS. 13 and 13A, the plunger 1364 is in its initial fully retracted position, which may be the desirable position for shipment and prior to use. When the plunger 1364 is in its initial fully retracted position, the locking arms 1380, particularly the distal ends 1392 of the locking arms 1380, are in a fully radially outward extended position relative to the shaft 1366 portion of the plunger, such that the distal ends 1392 do not contact the shaft 1366, as depicted in FIG. 16A. In this initial fully retracted position, the radial exterior of the distal ends 1392 of the locking arms 1380 are situated outward relative to the exterior of the shaft portion 1366. As the distal ends of the locking arms 1380 move into and through the orifice of the housing 1384, the exterior of the distal ends 1392 of the locking arms 1380 and the exterior of the shaft portion 1366 have the same radial position relative to one another. However, it may be preferable for the exterior of the shaft 1366 to be situated radially outward in comparison to the distal ends 1392 of the locking arms 1380, as depicted in FIG. 16B, as the locking arms 1380 pass through the orifice of the housing 1384 in order to maintain the rotational position of the plunger 1364 with respect to the housing 1384 and/or the barrel 1372. FIG. 16B illustrates the distal ends 1392 of the locking arms 1380 contacting the shaft 1366.

When the plunger 1364 is in a position within the barrel 1372 such that the flanged portions and/or the male tapered portions of the locking arms 1380 are distal the female tapered portion 1400 of the housing 1384 and into the housing 1364 such as the flange of the distal end 1392 of the locking arms 1380 abuts and/or is adjacent the interior of the ridge at the orifice of the housing 1384, as illustrated in FIGS. 14 and 14A, or distal thereto, the plunger 1364 is in its partially retracted position and ready for use. When the plunger 1364 is in a position within the barrel 1372 such that the flanged portions and/or male tapered portions of the locking arms 1380 are distal the female tapered portion 1400 of the housing 1384 and into the housing 1364 such that the flange of the distal end 1392 of the locking arms 1380 is distal the interior of the ridge 1396 at the orifice of the housing 1384, as illustrated in FIG. 15, the plunger 1364 is in an extended position. Also, when the plunger 1364 is in a partially retracted position (as depicted in FIGS. 14 and 14A) and/or in an extended position (as depicted in FIG. 15), the locking arms 1380, particularly the distal ends 1392 of the locking arms 1380, are in a radially outward extended position relative to the shaft portion 1366 of the plunger 1364, as depicted in FIG. 16C. FIG. 16C illustrates the distal ends 1392 of the locking arms 1380 being spaced apart from and not contacting the shaft 1366 but having less space between the distal ends 1392 and the shaft 1366 in comparison to FIG. 16A.

Referring again to FIG. 4D, this figure also illustrates a female luer adaptor 132 attached to the surgical device 100. The female luer adaptor 132 allows a clinician to connect an auxiliary syringe (not shown) having a male luer the mates with the female luer adaptor 132. The auxiliary syringe will include the medication that is introduced through the surgical device 100 proximal of the expandable member to the mucosa overlaying the SPG. Upon actuation (e.g., depression) of the auxiliary syringe, the medication travels from the auxiliary syringe to the female luer adaptor 132 through a tube 184 to the medication lumen 200 and eventually to opening 160. Alternatively, the tube 184 may be omitted by directly coupling the female luer adaptor 132 to the medication lumen 200. An additional alternative to the present disclosure includes using a separate tube for delivering the medication in lieu of the medication lumen 200 within the elongated flexible tubular member 108. The separate tube could be attached or unattached to the elongated flexible tubular member 108. The separate tube would have a proximal end, which could be coupled to the auxiliary syringe, and a distal end that includes an opening for delivering the medication.

Regardless of whether a tube 184 is included, the medication is preferably introduced through the surgical device 100 after the expandable member 116 is expanded because expanding the expandable member 116 reduces the likelihood of the medication from flowing down the patient's throat. As discussed above, after the medication is introduced into the nasal cavity through opening 160, the medication collects within the nasal cavity above the expandable member, when the expandable member 116 is expanded adjacent the choana. It may be preferable for the medication to collect within the nasal cavity and form a pool of medication such that the level of medication rises to sphenopalatine fossa and/or the mucosa overlaying the SPG. Once the desired medication level is attained, it may be desirable for the medication to remain in the patient's nasal cavity for a period of time to maximize the medication's exposure to the mucosa overlaying the SPG and the SPG itself. For example, it may be desirable for the medication to remain in the patient's nasal cavity at a level to overlay the mucosa of the SPG, for a period of time from about 5 minutes to 35 minutes, including any time interval (e.g., 1 minute, 2 minutes, 3 minutes, 4 minutes, 5 minutes, etc.) there between. It may be more desirable for such time period to be about 10 minutes to 30 minutes, and even more desirable for such time period to be about 15 minutes to 25 minutes, and even further desirable for such time period to be about 20 minutes.

To assist in maintaining the preferable level of medication for the desired time period, the auxiliary syringe may remain connected to the female luer adaptor 132 during such time period. After the medication has contacted the mucosa and the SPG for a sufficient period, the clinician may retract the auxiliary syringe, thereby removing some or all of the medication from the patient's nasal cavity through the same opening 160 used to introduce the medication. That is, by retracting the syringe, a negative pressure or suction force is created in the medication circuit, thereby pulling the medication located within the patient's nasal cavity through the opening 160 and back into the same or different auxiliary syringe. After the medication is withdrawn from the patient's nasal cavity, the expandable member 116 is collapsed, and the surgical device 100 may be removed. As discussed in more detail below, the benefit of including the expandable member 116 with the surgical device 100 allows the clinician to create a blockage within the patient's throat and fill a portion of the nasal cavity such that medication directly contacts the mucosa overlaying the SPG for a sustained period while preventing the medication from flowing down the patient's throat.

Figure 6A:
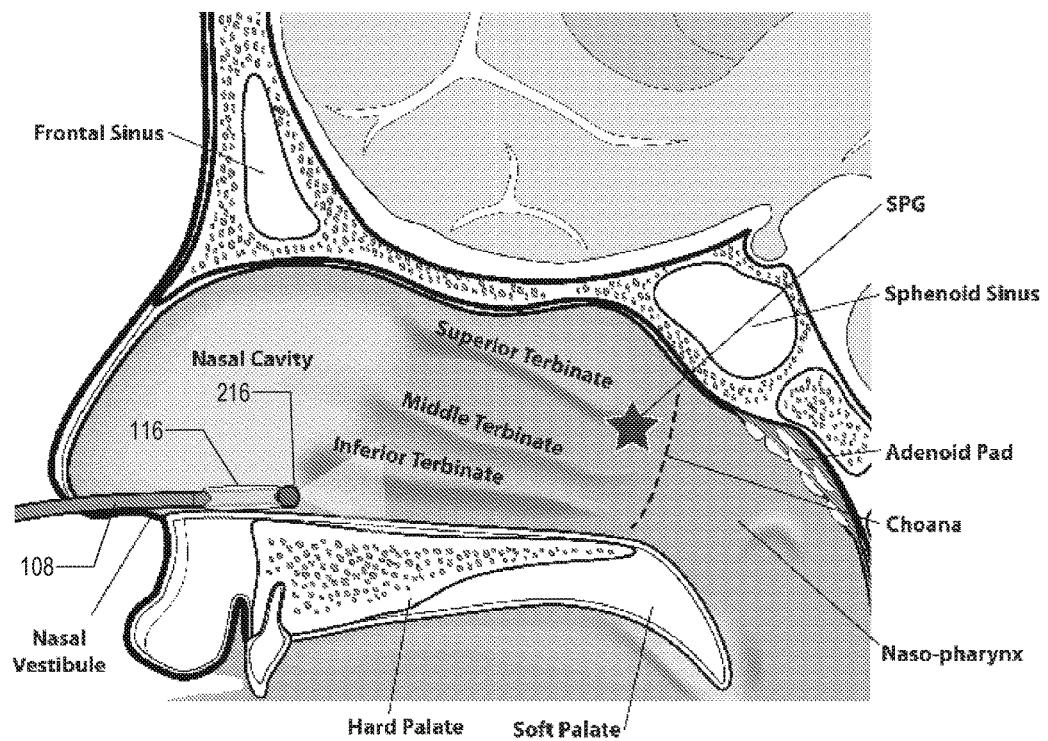
FIG. 6A is a cross-sectional view of a patient's head with an embodiment of a surgical device of the present disclosure, with the expandable member in a deflated state, entering the patient's nasal cavity.
Figure 6B:
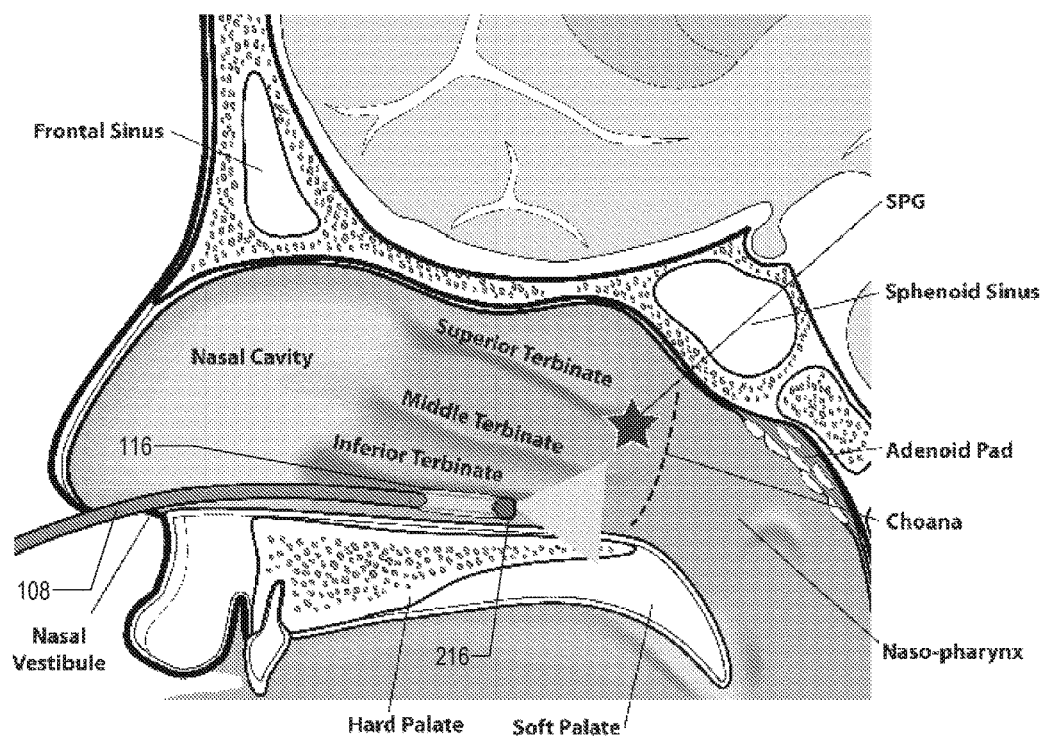
FIG. 6B is a cross-sectional view of a patient's head with an embodiment of a surgical device of the present disclosure, with the expandable member in a deflated state, located in the patient's nasal cavity.
Figure 6C:
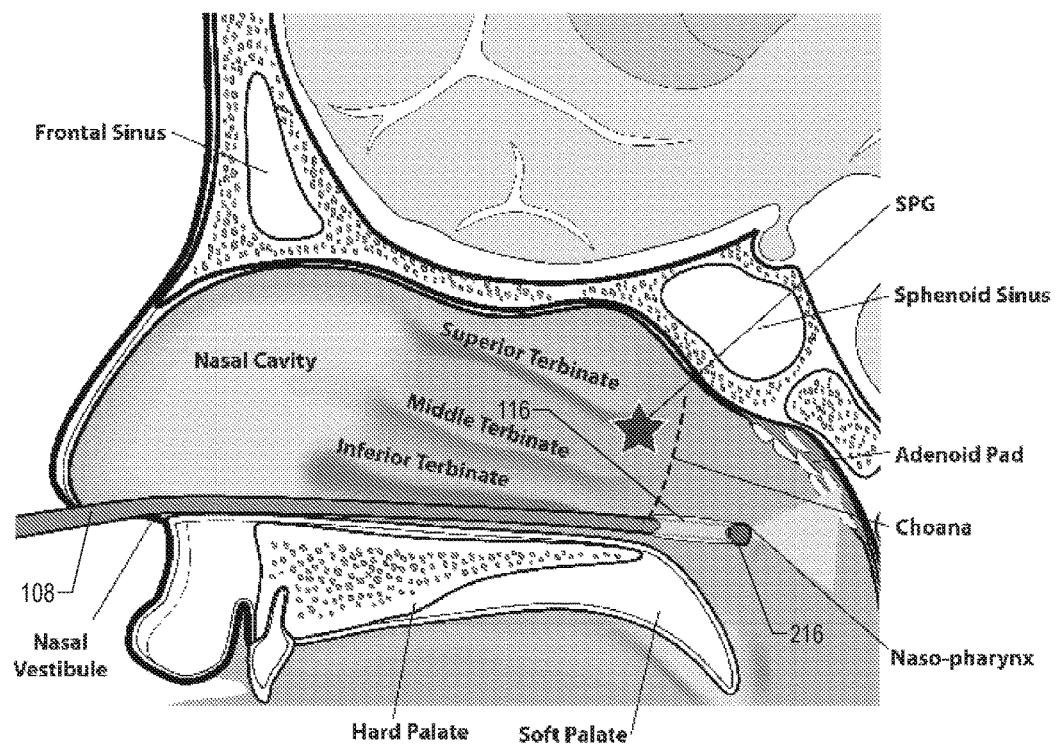
FIG. 6C is a cross-sectional view of a patient's head with an embodiment of a surgical device of the present disclosure, with the expandable member in a deflated state, located in the patient's nasal cavity with the expandable member disposed adjacent the choana.
Figure 6D:
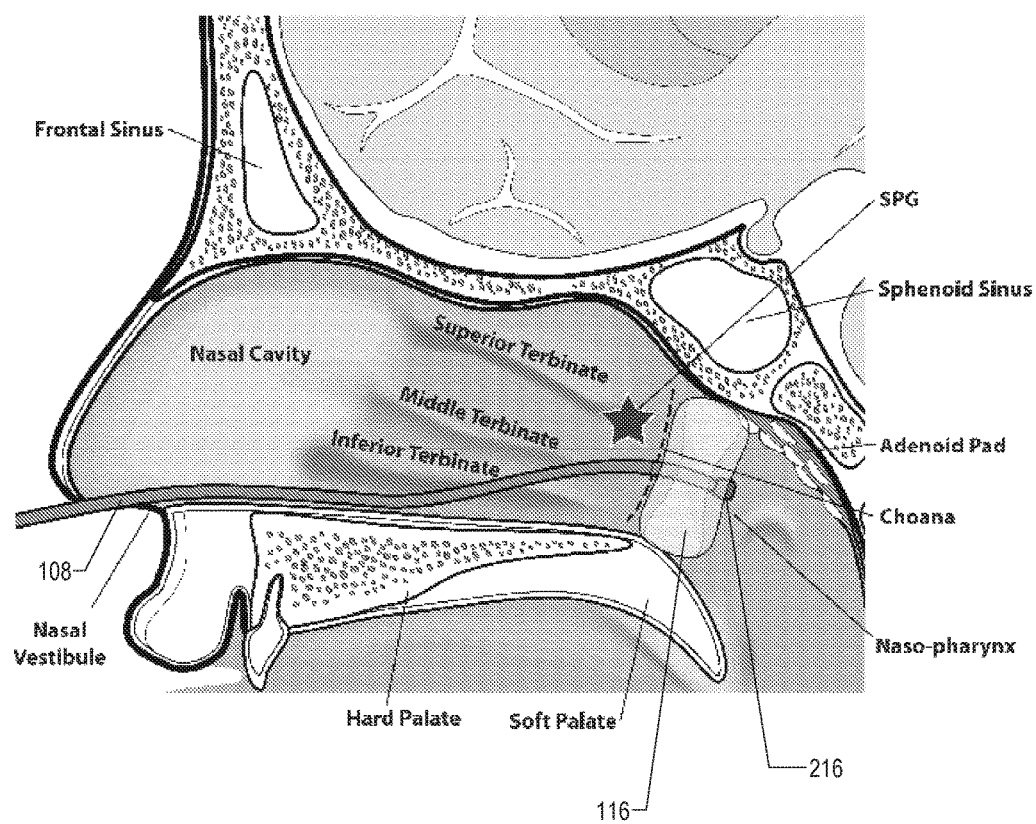
FIG. 6D is a cross-sectional view of a patient's head with an embodiment of a surgical device of the present disclosure, with the expandable member in an inflated state, located in the patient's nasal cavity with the expandable member disposed adjacent the choana.
Figure 6E:
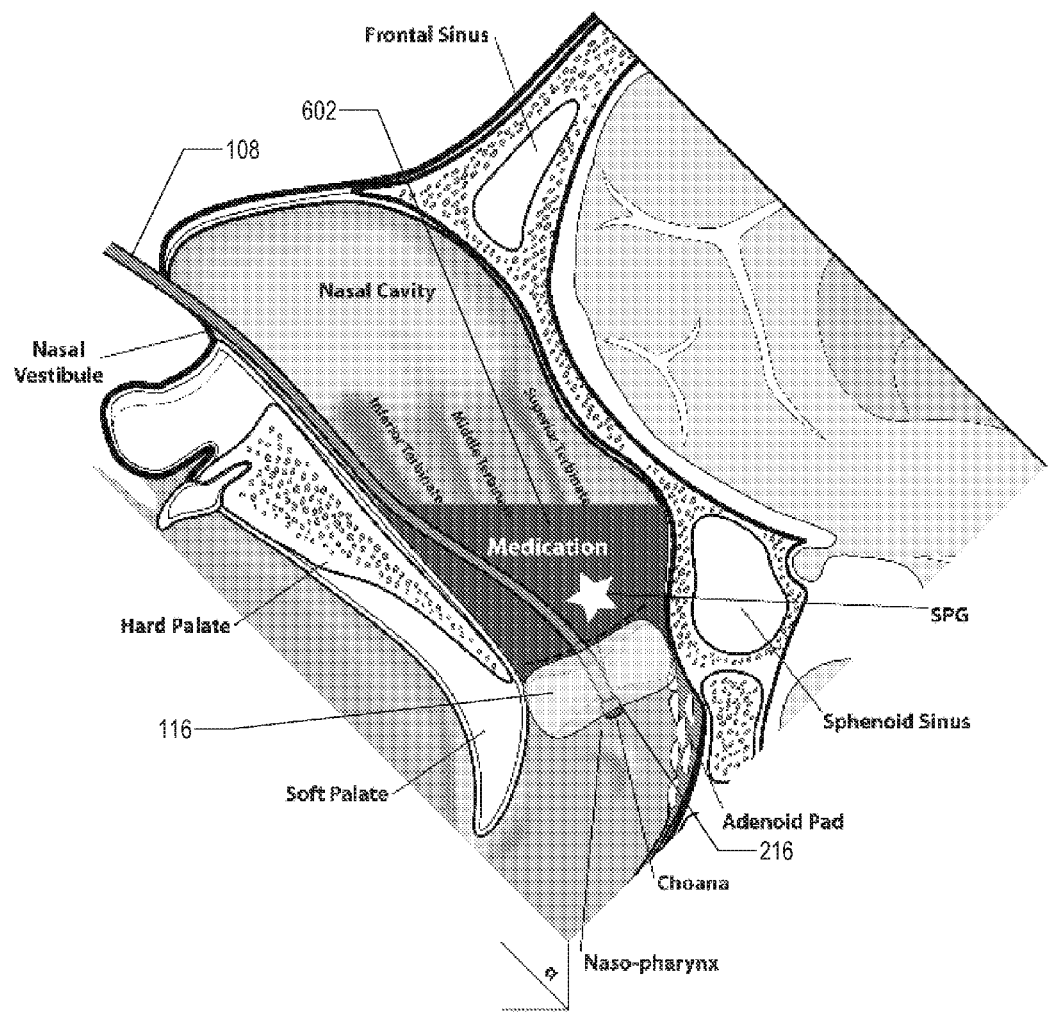
FIG. 6E is a cross-sectional view of a patient's head with an embodiment of a surgical device of the present disclosure, with the expandable member in an inflated state, located in the patient's nasal cavity with the expandable member disposed adjacent the choana and medication accumulated in the patient's nasal cavity adjacent the SPG.
Figure 7:
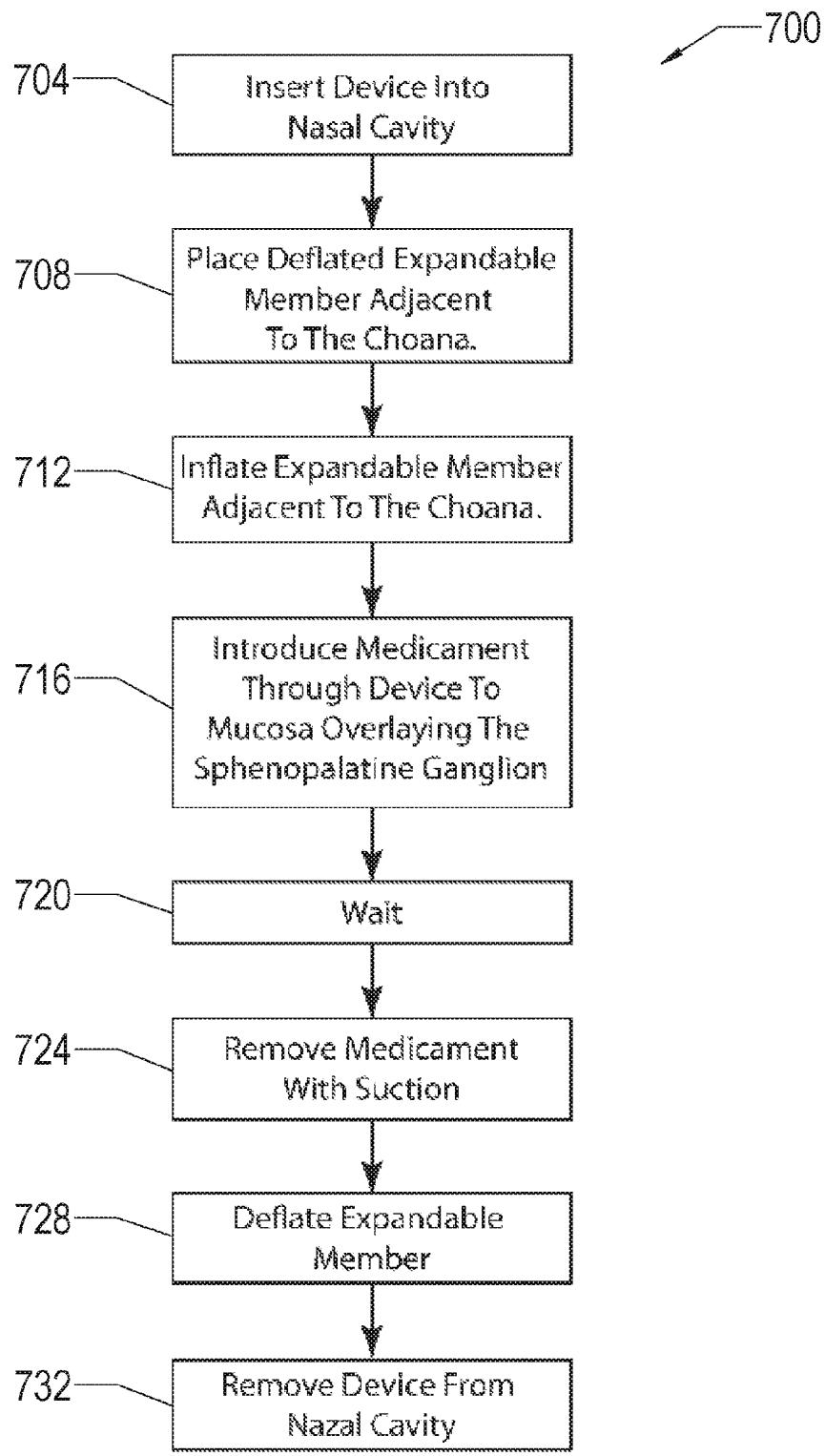
FIG. 7 is flow chart depicting a method of performing a surgical technique using a surgical device of the present disclosure.

Referring to FIG. 7, there is depicted a flow chart 700 representing at least some of the steps for performing a sphenopalatine ganglion block procedure utilizing the surgical device 100 of the present disclosure. Some of the steps of the flow chart 700 are illustrated in FIGS. 6A-6E. Step 704, which is illustrated in FIG. 6A, includes inserting the surgical device 100 into the patient's nasal cavity through one of the patient's nostrils (i.e., left nostril or right nostril). Specifically, the distal portion of the distal end 124 of the elongated flexible tubular member 108 is preferably inserted into the patient's nostril, while the expandable member 116 is entirely or partially deflated, and directed into the channel below the inferior turbinate and above the hard palate. It may also be preferable at the time of insertion of the surgical device 100 or shortly thereafter, that the illumination device 216 be activated. Upon activating the illumination device 216, light will transmit through the patient's hard palate. For example, when the distal end 124 of the elongated flexible tubular member 108 (and the illumination device 216) is located within the patient's nasal cavity as depicted in FIG. 6A, the illumination device 216 will be located at or below the posterior inferior turbinate and above the hard palate and be visible to a clinician viewing the interior of the oral cavity (patient's mouth), particularly the bottom of the palate (roof of the patient's mouth), and the light will appear to be transilluminating therefrom within the patient's head and visible to clinician from the oral cavity.

Referring to FIG. 6B, while continuing to activate the illumination device 216 and while the expandable member 116 is entirely or partially deflated, the distal portion of the distal end 124 of the elongated flexible tubular member 108 is inserted further into the patient's nasal cavity. When the distal end 124 of the elongated flexible tubular member 108 (and the illumination device 216) is located within the patient's nasal cavity as depicted in FIG. 6B, the illumination device 216 will continue to be located below the anterior of the inferior turbinate above the anterior of the hard palate further towards the soft palate in comparison location depicted in FIG. 6A.

Referring to FIG. 6C, while continuing to activate the illumination device 216 and while the expandable member 116 is entirely or partially deflated, the distal portion of the distal end 124 of the elongated flexible tubular member 108 is even inserted further into the patient's nasal cavity. When the distal end 124 of the elongated flexible tubular member 108 is located within the patient's nasal cavity as depicted in FIG. 6C, the illumination device 216 will be located above the soft palate, namely the nasopharynx, and the light will appear to be transilluminating therefrom and visible to clinician from the oral cavity. At this point, step 704 of FIG. 7 has been completed because the expandable member 116 is located at the desired position, namely in the nasopharynx adjacent the choana.

It may also be preferable to include depth markers printed on the elongated flexible tubular member 108, wherein the depth markers indicate to the clinician the distance from the expandable member 116 to the corresponding depth marker. For example, it may be preferable for the elongated flexible tubular member 108 to include depth markers every 1 centimeter, every 5 centimeters, every 10 centimeters from the proximal, mid- or distal portion of the balloon (or from the distal end of the flexible tubular member 108) to the corresponding depth marker. Adding such depth markers may provide the clinician with an additional or alternative means of determining whether the expandable member 116 and/or the distal end of the flexible tubular member 108 is located at the desired position, namely in the nasopharynx adjacent the choana.

Referring to FIG. 6D, when the illumination device 216 and the expandable member 116 are located in the nasopharynx adjacent the choana, the expandable member 116 is expanded by depressing plunger 164 of the syringe 112, as depicted in step 712 of FIG. 7, thereby blocking the choana. Once the choana is blocked, medication is introduced to the nasal cavity through the opening 160 of the flexible tubular member 108. As the medication is introduced, the expanded expandable member 116 prevents the flow of medication down the patient's throat. And because the patient's head it typically tilted backwards during this procedure, the medication collects proximally above the expandable member 116. Accordingly, the medication begins to accumulate within the nasal cavity. Upon a certain volume, such as 5 milliliters to 10 milliliters of medication being introduced to the nasal cavity through the opening 160, the level of medication rises within the nasal cavity, namely the sphenopalatine fossa, such that the medication contacts the mucosa overlaying the SPG. Introducing the medication in this fashion and maintaining the desired level of medication provides for direct and sustained contact with the mucosa overlaying the SPG. The medication is absorbed by the permeable mucosa overlaying the SPG. In comparison to spraying the mucosa with the medication, the device(s) and method(s) of the present disclosure provide direct and sustained contact with the mucosa and SPG, which is a more effective treatment. Also, varying the medication and contact times may further increase the effectiveness of the treatment. Varying the medication and contact times also provide the clinician the flexibility to personalize the patient's treatment. Another example of the way in which the clinician may utilize the device(s) and method(s) of the present disclosure to personalize the patient's treatment includes inflating the inflatable member to a certain pressure.

As mentioned above, it may be preferable for the patient's head to be tilted backwards during the procedure. Referring to FIG. 6E, it may be preferable for the patient's head to be tilted at an angle ($\alpha$) between 0 degrees and 90 degrees, and more preferable for the patient's head to be tilted at an angle ($\alpha$) between 15 degrees and 75 degrees, and further preferable for the patient's head to be tilted at an angle ($\alpha$) between 30 degrees and 60 degrees, and even further preferable for the patient's head to be tilted at an angle ($\alpha$) of about 45 degrees. Tilting the patient's head during the procedure allows the medication 602 to collect above the inflatable member 116 and contact the mucosa overlaying the SPG.

It may also be desirable to prevent the medication from being introduced or sprayed into the nasal cavity in an unknown direction. That is, it may be desirable to control the introduction of the medication into the nasal cavity such that the medication collects within the nasal cavity above the expandable member, forms a pool of medication 602, and the level of medication raises to sphenopalatine fossa and/or the mucosa overlaying the SPG without randomly spraying the medication into the nasal cavity. Controlling the introduction of the medication in this manner increases the likelihood that that medication reaches the mucosa overlaying the SPG and the SPG itself. That is, upon exiting the flexible tubular member, the medication initially contacts the expandable member and forms a pool thereof prior to contacting any tissue within the nasal cavity.

Referring to FIG. 9A and FIG. 9B, there are depicted means for controlling the direction from which the medication exits the flexible tubular member 108' and is introduced to the nasal cavity. Referring specifically to FIG. 9A, such means may include a deflector 902 that directs the flow of medication exiting the flexible tubular member 108' toward the expandable member 116. Directing the flow of medication toward the expandable member 116 reduces the likelihood that the medication will be distributed, via spraying, in an unknown direction. As illustrated in FIG. 9A, the deflector 902 is coupled to the flexible tubular member 108. The deflector 902 can be located exteriorly of the flexible tubular member 108, such as in the form of a sleeve that surrounds the opening 160, thereby forcing the outflow of medication towards the inflatable member 116. The deflector 902 can also be integral with the flexible tubular member 108', such that the portion of the flexible tubular member 108' adjacent the opening 160 directs the outflow of medication towards the inflatable member 116. The deflector 902 may also be a separate component that is inserted at least partially within the flexible tubular member 108' and directs the outflow of medication towards the inflatable member 116. Alternatively, in lieu of a deflector 902, the means for controlling the direction from which the medication exits the flexible tubular member 108' and is introduced to the nasal cavity may include the opening 160 having a particular directional shape such that the shape of the opening 160 directs the outflow of medication in a direction towards the inflatable member 116. Referring specifically to FIG. 9B, a further alternative means for controlling the direction from which the medication exits the flexible tubular member 108' and is introduced to the nasal cavity includes the opening 160 adjacent the expandable member 116, wherein a deflector is omitted. The expandable member 116 may optionally have an inflated configuration such that its shape includes a narrower width (or cross sectional profile) proximal the flexible tubular member 108' and a wider width (or cross sectional profile) distal the flexible tubular member 108'. This may allow the opening 160, which is adjacent the narrower width portion of the flexible tubular member 108' to have a perpendicular orientation within and the flexible tubular member 108' such that upon medication exiting the opening 160, the medication contacts the wider width portion of the flexible tubular member 108'. And after the level of the pool of medication rises above the opening 160 distal the expandable member 116, the additional medication exiting the opening enters directing in the pool.

Referring to step 720 of FIG. 7, it may be preferable for the medication to remain within the nasal cavity and contact the mucosa overlaying the SPG, as well as the SPG, for a predetermined period of time (e.g., about 20 minutes), as discussed above. Referring to step 730, upon the SPG being directly exposed to the medication for the desired period, the medication is removed from the nasal cavity by suctioning the medication through the opening 160 with an auxiliary syringe. Once the medication is removed, the expandable member 116 may be collapsed by retracting the plunger 164 of the syringe 112, as depicted in step 728 of FIG. 7. As set forth in step 732, after the medication is removed and the expandable member 116 is collapsed, the surgical device 100 may be removed from the nasal cavity.

The procedure discussed above with respect to FIG. 7 performs a sphenopalatine ganglion block for one SPG located on one (i.e., left or right) side of the patient's head. Upon completing the sphenopalatine ganglion block for one side of the head, the same procedure can be repeated by inserting the distal end of the elongated flexible tubular member 108 into the patient's other nostril and applying the medication to the other SPG.

Figure 11A:
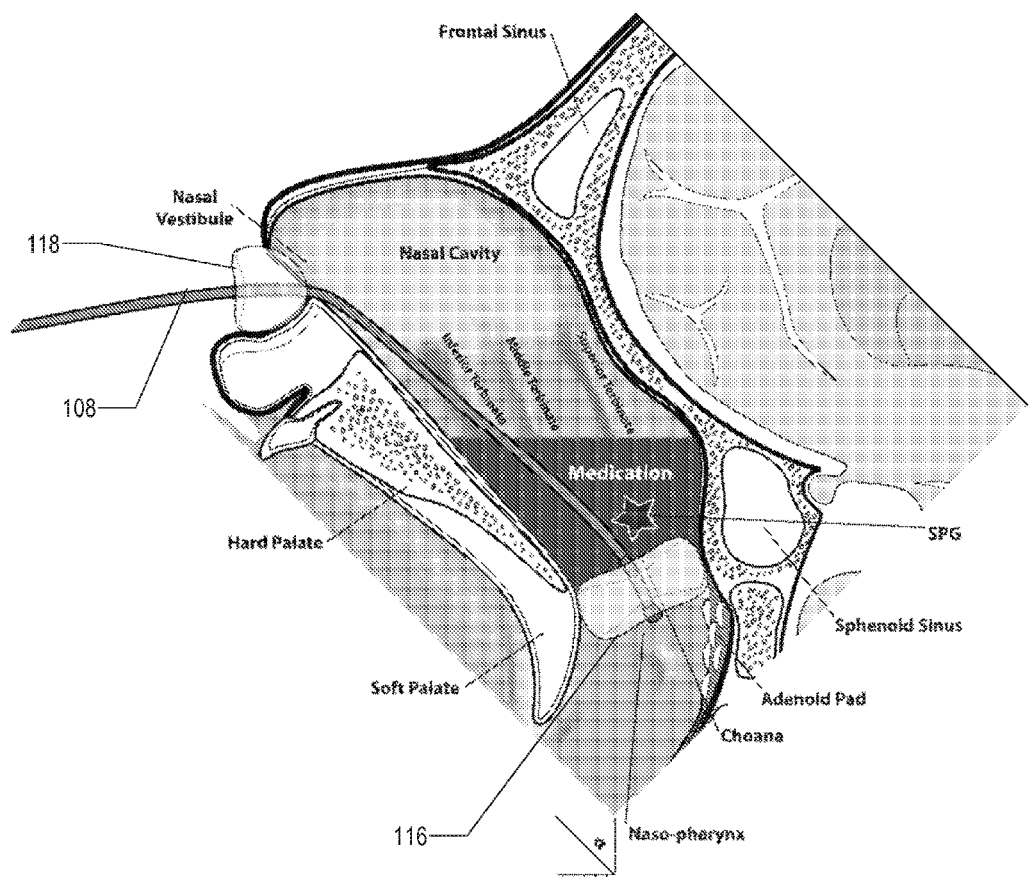
FIG. 11A is a cross-sectional view of a patient's head with an embodiment of a surgical device of FIG. 10A located in the patient's nasal cavity with the expandable member disposed adjacent the choana and medication accumulated in the patient's nasal cavity adjacent the SPG and a second expandable member disposed adjacent and exterior of the patient's nostril.
Figure 12:
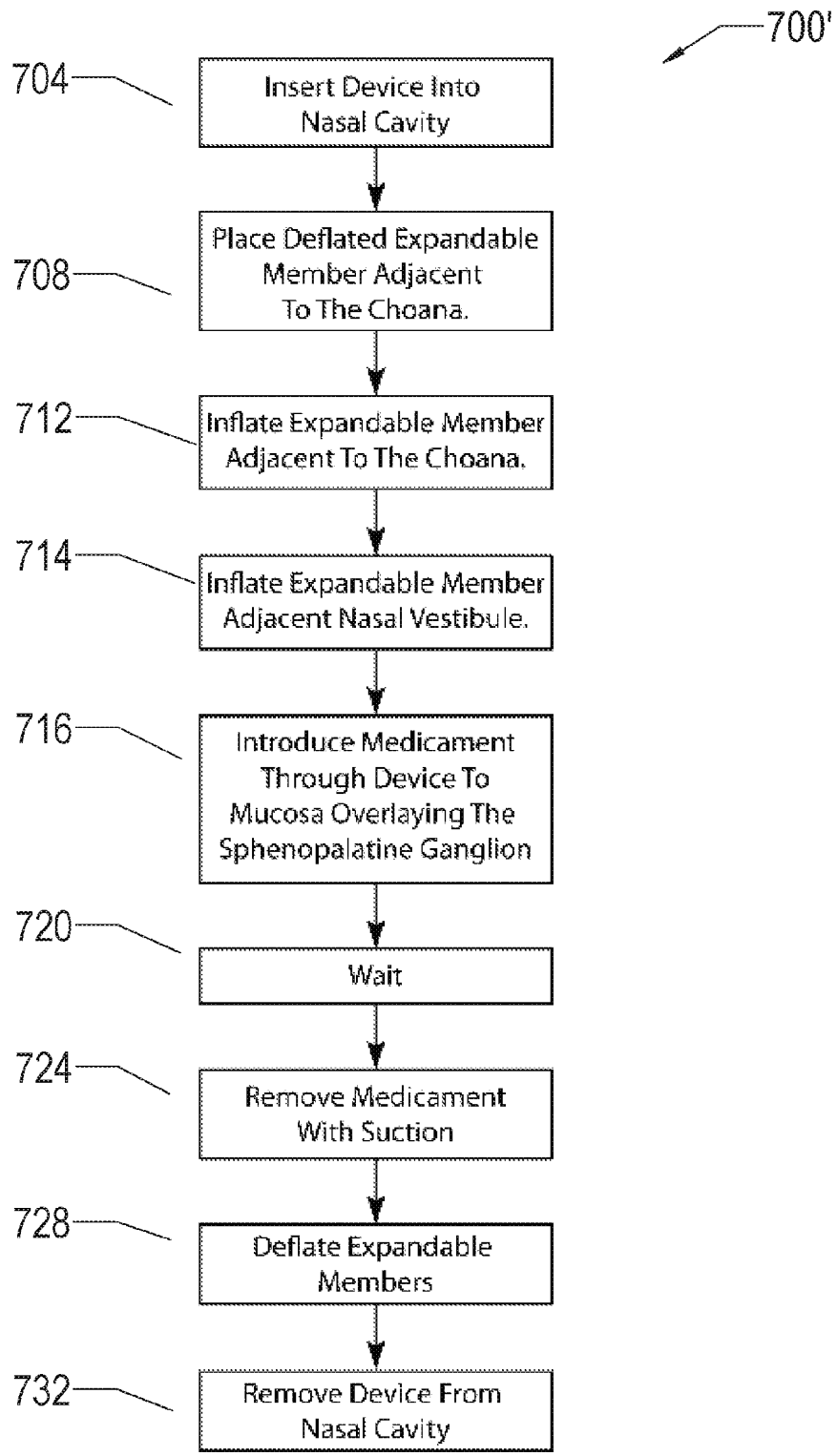
FIG. 12 is flow chart depicting an alternative method of performing a surgical technique using an alternative embodiment of the surgical device of the present disclosure.

Referring to FIG. 10A, there is depicted an alternative embodiment of the surgical device 100 depicted in FIGS. 1-4. As discussed above the surgical device 100 depicted in FIGS. 1-4 includes expandable member 116 located at, adjacent to or toward the distal end 124 of the flexible tubular member 108. As depicted in FIG. 10A, the surgical device 100' may include a second expandable member 118 disposed proximally of expandable member 116 and the opening 160. Again, the expandable member 116 of the surgical device 100 allows the clinician to create a blockage within the patient's throat and fill a portion of the nasal cavity such that medication directly contacts the mucosa overlaying the SPG for a sustained period while preventing the medication from flowing down the patient's throat. The second expandable member 118 may be used to prevent the medication from exiting the patient's nostril. As depicted in FIG. 11A and FIG. 12, after introducing the surgical device 100' through the patient's nostril, the expandable member 116 is disposed adjacent the choana, the expandable member 116 is inflated, and medication is introduced to patient's nasal cavity through the opening 160, and the medication collects above the expandable member 116 and adjacent the SPG. After or in conjunction with introducing the surgical device 100' through the patient's nostril and/or locating the expandable member 116 the choana, the second expandable member 118 is disposed adjacent the exterior of the patient's nostril or in the patient's nostril, and the second expandable member 118 is inflated. Inflating the expandable member 116 adjacent the choana and the second expandable member 118 adjacent patient's nostril allows the medication to collect between the two expandable members 116, 118 while preventing the medication from flowing down the patient's throat and escaping through the patient's nostril, particularly if the patient moves his/her head and/or when the patient's head is not in the most desirable orientation.

The second expandable member 118 may be coupled to the same inflation lumen and inflation port used to inflate expandable member 116 so that the two expandable members 116, 118 are inflated simultaneously. Or the surgical device 100' may include a second inflation lumen (not shown) and/or a second inflation port (not shown) to inflate the second expandable member 118 separately from expandable member 116. The distance from the entry of a patient's nostril to a patient's choana may vary among patients. Accordingly, it may be desirable to have a means for adjusting the distance between the two expandable members 116, 118. For example, it may be desirable to have a means for sliding the second expandable member 118 over the elongated flexible tubular member 108. Sliding the second expandable member 118 over the elongated flexible tubular member 108 relative to expandable member 116, which may be fixed or slidable, allows a clinician to initially locate the expandable member 116 adjacent the patient's choana, then insert or place the second expandable member 118 adjacent the patient's nostril. Once the expandable members 116, 118 are located in the desired locations, the expandable members 116, 118 are inflated, thereby forming a snug fit in the patient's nostril and preventing medication from flowing down the patient's throat and escaping through the patient's nostril.

Figure 11B:
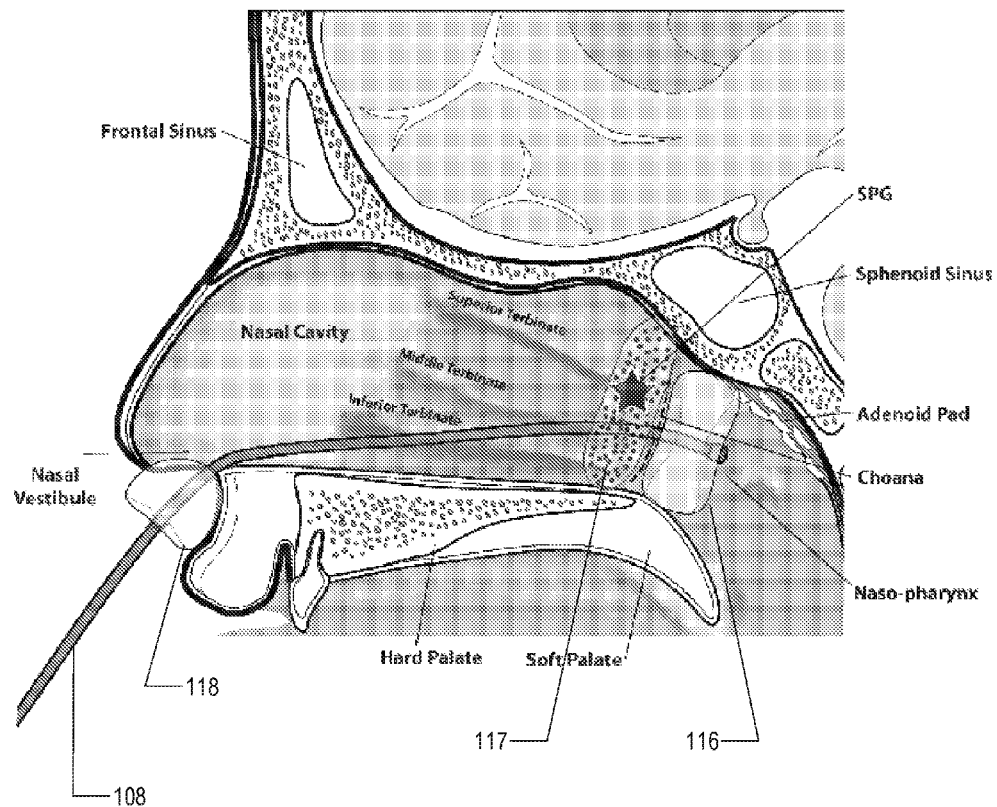
FIG. 11B is a cross-sectional view of a patient's head with an embodiment of a surgical device of FIG. 10B located in the patient's nasal cavity with the expandable member disposed adjacent the choana and the delivery device in the patient's nasal cavity adjacent the SPG, and a second expandable member disposed adjacent and exterior of the patient's nostril.

Referring to FIG. 10B, there is depicted another alternative embodiment of the surgical device 100 depicted in FIGS. 1-4. In comparison to the embodiment of the surgical device 100' illustrated in FIG. 10A, the surgical device 100" illustrated in FIG. 10B, further includes a delivery device 117 between the expandable members 116, 118 for delivering the medication. The delivery device 117 may include an expandable member having a permeable membrane or semi-permeable membrane disposed over the opening 160 such that upon expansion, pores within the permeable membrane or semi-permeable membrane increase in size and allow the medication to exit there through. Additionally, the delivery device 117 may alternatively include a sponge disposed over opening 160. As depicted in FIG. 11B, it may be preferable to locate the surgical device of FIG. 10B in the patient's nasal cavity with the expandable member 116 disposed adjacent the choana, the delivery device 117 in the patient's nasal cavity adjacent the SPG, and the second expandable member 118 disposed adjacent and exterior of the patient's nostril. Once the delivery device 117 is located adjacent the SPG, the medication is delivered through the delivery device 117.

For various medical and health-related purposes, there is also a potential need to insure that the surgical device is used only for treating a single patient and not used for treating multiple patients. Typically, the surgical device may be used on both sides of the patient's nasal cavity by inserting the surgical device into both nostrils of the patient, wherein the treatment of each side of the nasal cavity for the same patient may be considered a separate procedure. As discussed above, the LED is battery powered. One method of insuring that the surgical device is only used on a single patient is to preclude the use of the LED, and therefore, prevent the surgical device's ability to transilluminate through tissue after a predetermined time. Precluding the use of the LED may be assured by depleting the batteries power supply. As discussed above, a typical sphenopalatine ganglion block procedure may take between 5 minutes and 35 minutes for one side of the nasal cavity. That is, it may take between 10 minutes and 70 minutes for a clinician to complete a sphenopalatine ganglion block procedure for both sides of the patient's nasal cavity. Accordingly, if the battery power is depleted after such predetermined time, then the LED will be inoperable.

Figure 17:
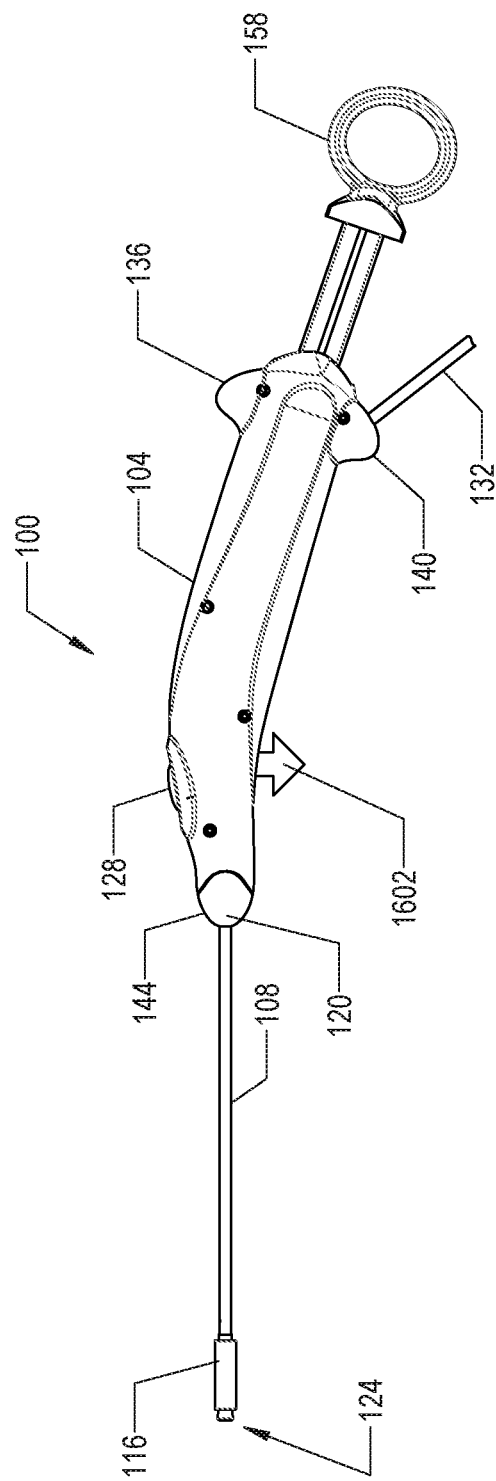
FIG. 17 is a side view of an alternative embodiment of the surgical device depicted in FIG. 4.

In addition to insuring that the battery power is depleted after such predetermined time, it may also be desirable to prevent the LED from consuming any battery power during shipment, which would prematurely consume the limited availability of the battery's power. A potential solution for solving these two concerns is the inclusion of a pull-tab and parallel circuits within the surgical device. Referring to FIG. 17, there is depicted the proximal end of a pull tab 1602 inserted into the handle 1602 of the surgical device in an un-pulled position. Referring to FIG. 18, the distal end of the pull tab 1602 is disposed adjacent the battery terminal or between the battery terminals to interrupt and maintain an open circuit as schematically depicted in FIG. 19A.

Referring to FIGS. 19A, 19B, and 19C, there is shown a schematic diagram of a circuit 1900 in three different phases. The circuit 1900 has two potential circuit paths: one potential circuit path includes delivering power from the battery 1904 to the resister 1908; and the other potential circuit path includes delivering power from the battery 1904 to the resister LED, which is indicated as item 216 in these figures. During shipment of the surgical device 100, it is desirable that both circuit paths remain open. Referring to FIG. 19A, inclusion of the pull tab 1602 in an un-pulled position insures that both circuit paths will be remain open, thereby preventing the resistor 1908 and the LED 216 from drawing power from the battery. Also depicted within the circuit of FIG. 19A, the switch 128 is in an open position because it is not depressed. Referring to FIG. 19B, the switch 128 is still in an open position. The circuit path to the LED 216 is, therefore, open in both FIGS. 19A and 19B. The circuit path to the resistor 1908 is open in FIG. 19A, but the circuit path to the resistor 1908 is closed in FIG. 19B because the pull tab 1602 has been removed and illustrated in a pulled-position. Once the pull tab 1602 is removed and/or in a pulled position, the resistor 1908 begins drawing power from the battery 1904. The power capacity of the battery 1904 and/or the size of the resistor 1908 are designed or configured to utilize all of the battery's power capacity within a predetermined time, thereby preventing a clinician from performing more than one sphenopalatine ganglion block procedure on a single patient. For example, referring to FIG. 19C, once the switch 128 is in a closed position, the circuit path to the LED 1816 is also closed. Accordingly, this figure illustrates both circuit paths in closed positions—the battery 1904 is delivering power to the resister 1808 and to the LED 1816.

An alternative means of depleting the battery power in a predetermined time includes a one way switch for the LED such that LED always remains on, thereby continuously draining batter power. If this means is used, the power supply and/or resistance of the LED would be designed to deplete the battery power within a predetermined time.

Figure 20A:
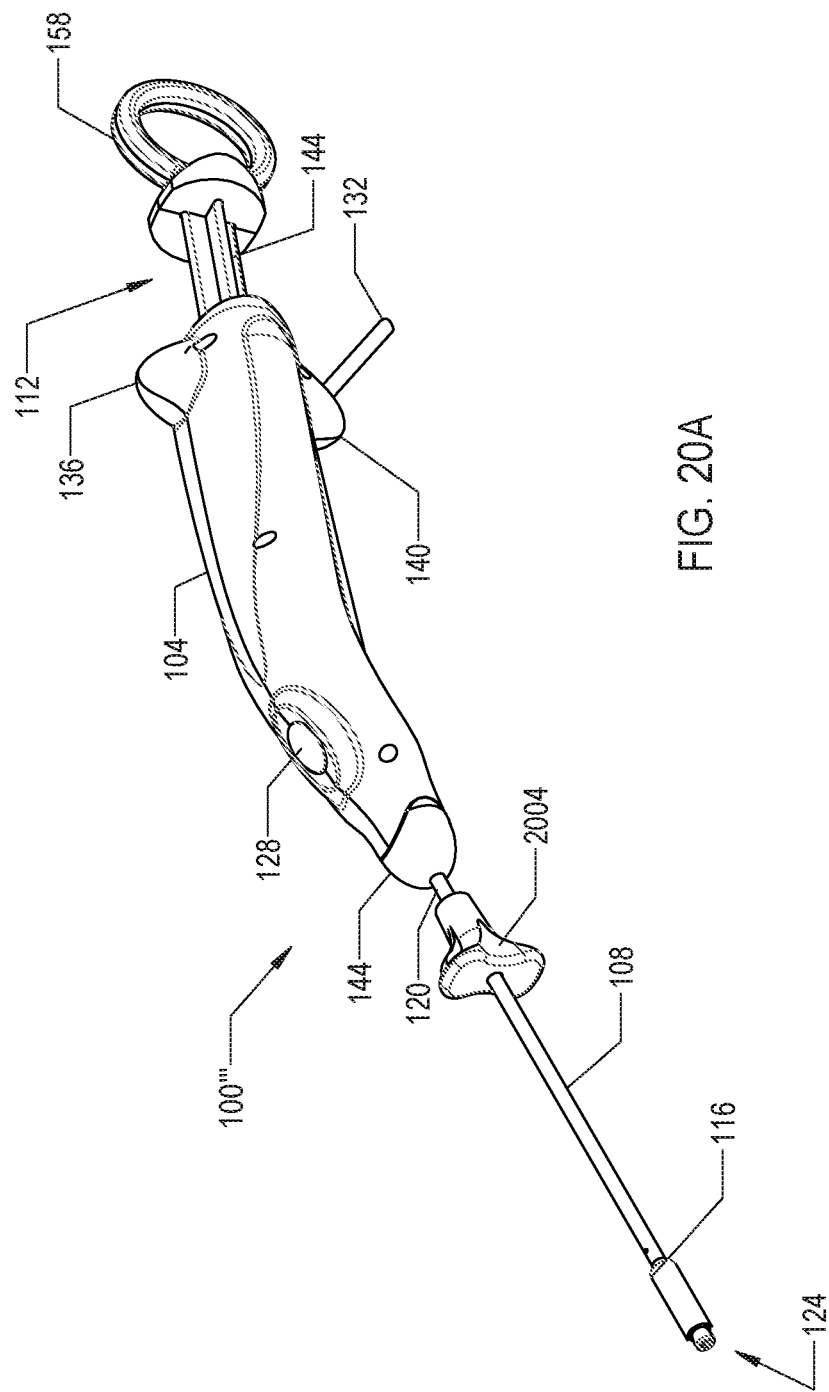
FIG. 20A is a perspective view of an alternative embodiment of a surgical device of the present disclosure, wherein the stabilizer is disposed proximate the handle of the surgical device.
Figure 20B:
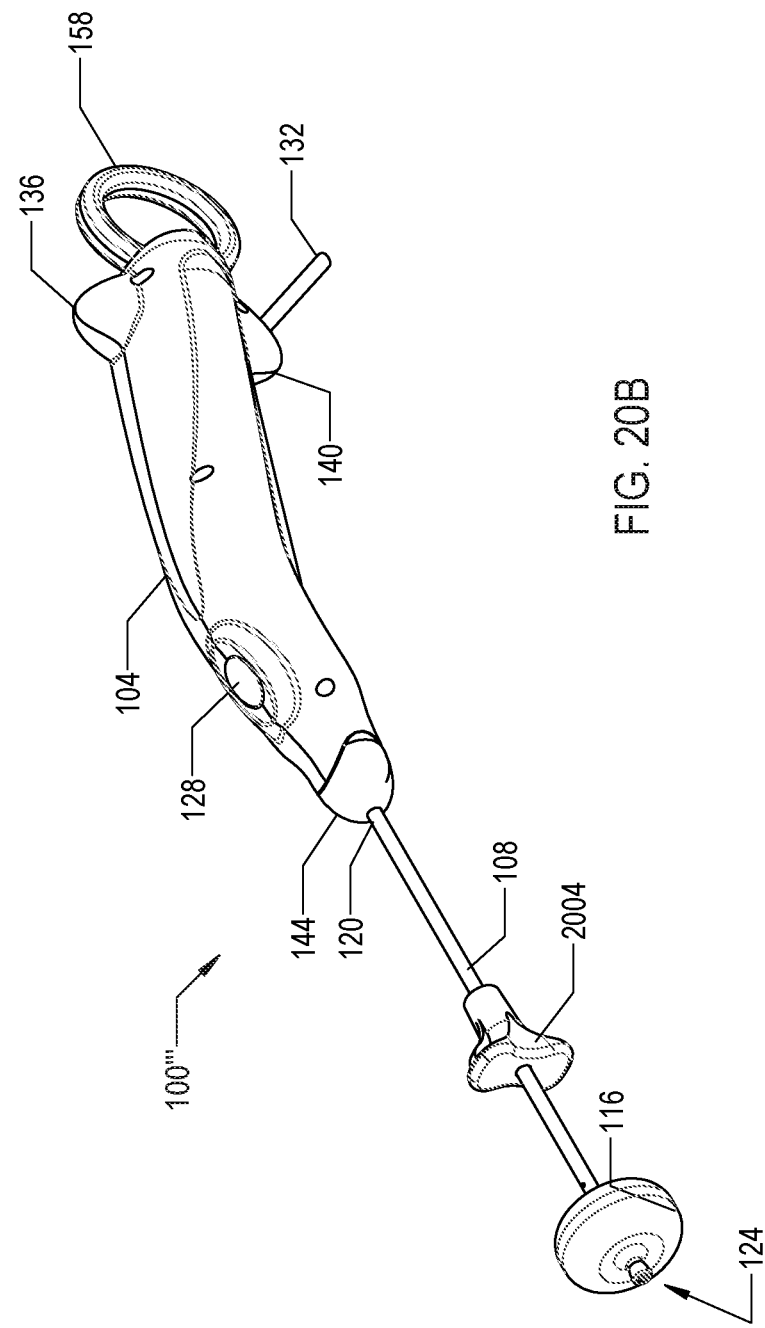
FIG. 20B is a perspective view of the alternative embodiment of the surgical device illustrated in FIG. 20A, wherein the stabilizer is disposed distally of the handle of the surgical device.

Referring to FIGS. 20A and 20B, there is depicted a further alternative embodiment of the surgical device 100''' depicted in FIGS. 1-4. In comparison to the embodiment of the surgical device 100 illustrated in in FIGS. 1-4, the surgical device 100''' illustrated in FIGS. 20A and 20B also includes a stabilizer 2004 slidably disposed over the flexible tubular member 108 between the distal end 144 of the handle 104 and the expandable member 116. As will be discussed in more detail below, the stabilizer 2004 is able to slide over and relative to the flexible tubular member 108. For instance, FIG. 20A illustrates the stabilizer 2004 adjacent to and/or distal the distal end 144 of the handle 104 (or at and/or adjacent the proximal end of the flexible tubular member 108) and proximal the expandable member 116 (or proximal the distal end of the flexible tubular member 108). FIG. 20B, however, illustrates the stabilizer 2004 distally of the distal end 144 of the handle 104 (or distally of the proximal end of the flexible tubular member 108) and more proximal the expandable member 116 (or more proximal the distal end of the flexible tubular member 108), in comparison the position of the stabilizer 2004 depicted in FIG. 20A.

Figure 21A:
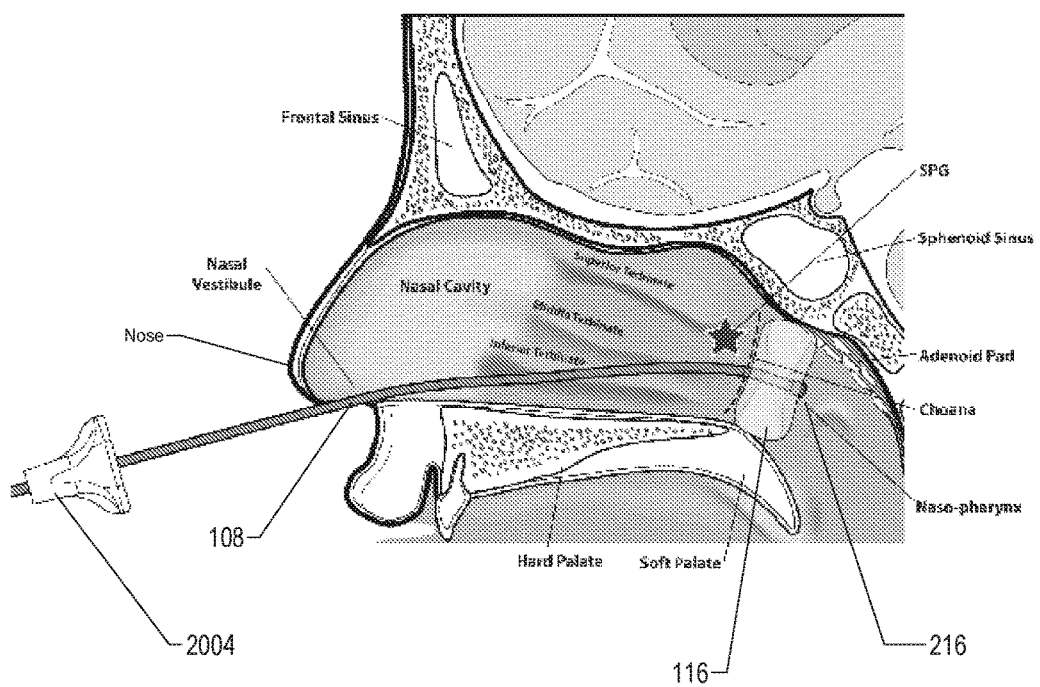
FIG. 21A is a cross-sectional view of a patient's head and the embodiment of the surgical device illustrated in FIG. 20A, wherein the expandable member is in an inflated state and located in the patient's nasal cavity and disposed adjacent the choana, wherein the stabilizer is disposed distally of the patient's nose.
Figure 21B:
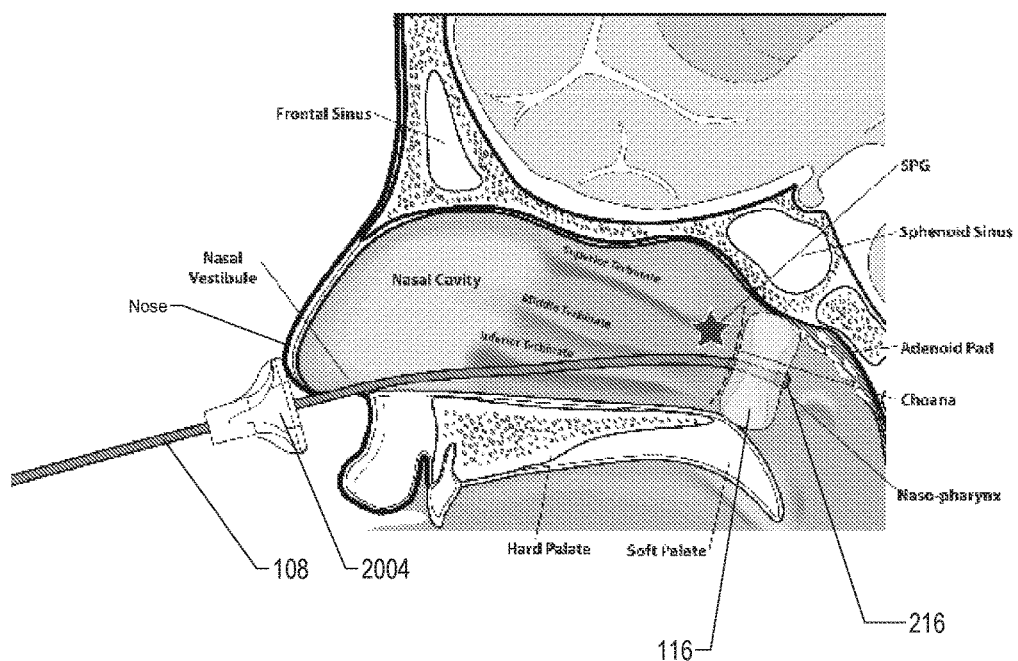
FIG. 21B is a cross-sectional view of a patient's head and the embodiment of the surgical device illustrated in FIG. 20A, wherein the expandable member is in an inflated state and located in the patient's nasal cavity and disposed adjacent the choana, wherein the stabilizer is disposed adjacent and/or contacts the patient's nose.

For example, referring to FIG. 21A, upon placing the surgical device 100''' in the nasal cavity such that the expandable member 116 is located at the desired position, namely in the nasopharynx adjacent the choana, and the expandable member 116 is expanded adjacent the choana, the location of the stabilizer 2004 is initially distal the patient's nose. Referring to FIG. 21B, after placing the surgical device 100''' in the nasal cavity and expanding the expandable member 116 adjacent the choana, the clinician may slide the stabilizer 2004 along the elongated flexible tubular member 108 such that the stabilizer 2004 contacts the patient's nose or anterior naris or is located adjacent to either the patient's nose or anterior naris. Placing the stabilizer 2004 against or adjacent the patient's nose or anterior naris assists in securing the expandable member 116 in its desired location, namely adjacent the choana in its inflated state. For example, when the expandable member 116 is disposed adjacent the choana in its inflated state, the stabilizer 2004 provides anterior traction on the seated expandable member 116 from exterior the patient's nasal cavity, nose and/or anterior naris. That is, the stabilizer 2004 aids in retaining the expandable member 116 (and/or the expandable member 118) in position while the clinician is performing the sphenopalatine ganglion block procedure. Specifically, the stabilizer 2004 may prevent the surgical device 100''' or a portion thereof, namely the flexible tubular member 108 (or a portion thereof) and/or the expandable member 116 from moving and/or becoming unseated during inflation in the event the patient moves. For example, rapid or quick movement of the patient's head, such as movement resulting from a cough or a sneeze, may cause the expandable member 116 to also move. In the event of such movement, the seal formed by the expandable member 116 against the choana may become unseated or unstable, thereby allowing the fluid (e.g., medication) located above the expandable member 116 to leak past the expandable member 116 and into the patient's throat.

Continuing to refer to FIG. 21B, the configuration of the stabilizer 2004 depicted in this figure is such that it remains completely outside the patient's nose and does not enter the patient's nostril or nasal vestibule. However, the configuration of the stabilizer could be designed to be placed partially or completely inside the patient's nostril. For example, the stabilizer could be designed such that one portion of the stabilizer is inside the patient's nostril and another portion of the stabilizer is outside the patient's nose.

Referring to FIGS. 22A-22D, the stabilizer 2004 depicted in these figures is configured to remain completely outside the patient's nose without any portion thereof entering the patient's nostril or nasal vestibule. Stabilizer 2004 has a proximal portion 2012, a distal portion 2008 and a lumen 2016 extending along the longitudinal axis of the stabilizer 2004 and through both the proximal portion 2012 and the distal portion 2008. That is, the lumen 2016 extends from the proximal end of the proximal portion 2012 to the distal end of the distal portion 2008 of the stabilizer 2004.

Figure 22B:
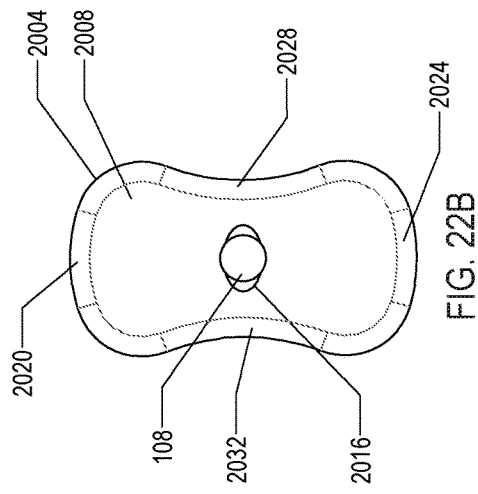
FIG. 22B is a cross-sectional end view of the stabilizer and elongated flexible tubular member depicted in FIG. 22A taken along line A-A, wherein the stabilizer is in an uncompressed state.
Figure 22D:
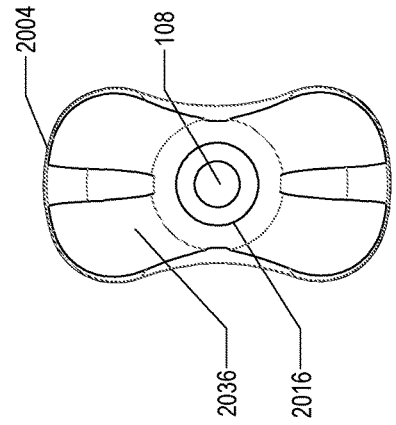
FIG. 22D is a cross-sectional end view of the stabilizer and elongated flexible tubular member depicted in FIG. 22A taken along line B-B.
Figure 22A:
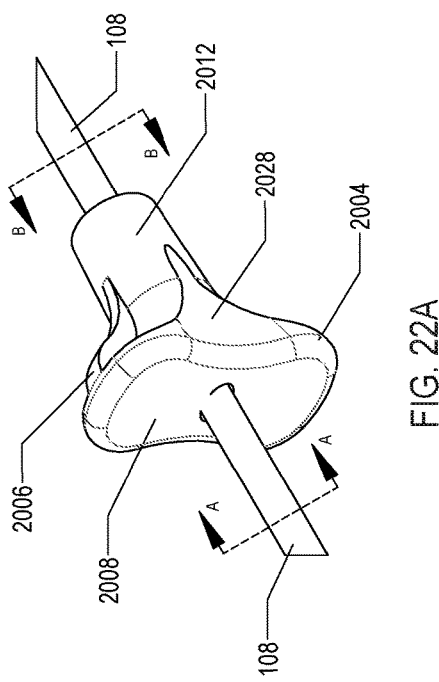
FIG. 22A is an enlarged perspective view of the stabilizer and elongated flexible tubular member illustrated in FIGS. 20A and 20B.
Figure 22C:
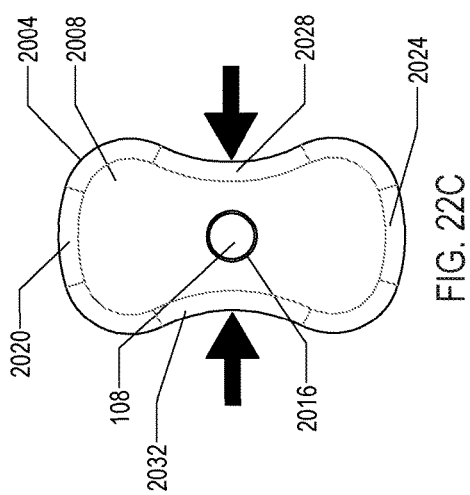
FIG. 22C is an alternative embodiment of the cross-sectional end view of the stabilizer and elongated flexible tubular member depicted in FIG. 22A taken along line A-A, wherein the stabilizer is in a compressed state.

The proximal portion 2012 of the stabilizer 2004 has a smaller cross-sectional profile in comparison to the distal portion 2008, although the relative sizes of such cross-sectional profiles may be reversed or the same. Referring to FIGS. 22B & 22C, the cross-sectional profile of the distal portion 2008 may have a generally saddle shape. For example, the distal portion 2008 may have a top portion 2020, a bottom portion 2024, and two side portions 2028, 2032. And the length between the top portion 2020 and bottom portion 2024 may be less than the length between the two side portions 2028, 2032. Also, the top portion 2020 and bottom portion 2024 may each have a convex shape, and the two side portions 2028, 2032 may each have concave shapes, thereby creating a saddle-shaped cross sectional profile for the distal portion 2008 of the stabilizer 2004.

The concave shaped side portions 2028, 2032 also create indentations that allow the clinician to easily grasp the stabilizer 2004 with his/her finger(s) and/or thumb. The stabilizer 2004 may be constructed of a flexible and/or polymeric material, such as silicone. Upon a clinician grasping the flexible stabilizer 2004 and squeezing it on the side portions 2028, 2032, as illustrated by the arrows depicted in FIG. 22C, the stabilizer 2004 is forced into and enters a compressed state. And when the clinician releases the stabilizer 2004, it returns to an uncompressed state, as depicted in FIG. 22B.

As mentioned above, the stabilizer 2004 comprises a lumen 2016 extending along the longitudinal axis of the stabilizer 2004 and through both the proximal portion 2012 and the distal portion 2008 such that the lumen 2016 extends from the proximal end of the proximal portion 2012 to the distal end of the distal portion 2008 of the stabilizer 2004. The cross-sectional profile of the lumen 2016 may vary or remain constant from its proximal end to its distal end. For example, the shape of the lumen at and/or towards its proximal end may be circular, while the shape of the lumen at and/or towards its distal end may be oval or vice versa. For example, FIG. 22B depicts the cross-sectional shape of the lumen 2016 as oval at the distal portion 2008 of the stabilizer 2004, and FIG. 22C depicts the cross-sectional shape of the lumen 2016 as circular at the distal portion 2008. Similarly, FIG. 22D depicts the cross-sectional shape of the lumen 2016 as circular at the proximal portion 2012.

Regardless of whether the cross-sectional shape of the lumen 2016 is circular or oval, the circumference of such circle or oval is greater than the circumference of the flexible tubular member 108 extending through the lumen 2016. The size of the circumference of the lumen 2016 being greater than the size of the circumference of the flexible tubular member 108 insures that the stabilizer 2004 can slide relative to the flexible tubular member 108. Even though the circumference of the lumen 2016 is greater that of the flexible tubular member 108, the lumen 2016 contacts the flexible tubular member 108 in either its compressed state or its uncompressed state. For example, assuming that the cross-sectional shape of the lumen 2016 is oval at its distal end and transitions to a circular shape at its proximal end, as illustrated in FIGS. 22B and 22D, one or more portions of the lumen 2016 contacts one or more portions the flexible tubular member 108, when the stabilizer 2004 is in an uncompressed state. And upon a clinician grasping the flexible stabilizer 2004 and squeezing it on the side portions 2028, 2032, the stabilizer 2004 is forced into and enters an compressed state, as illustrated in an FIG. 22C, such that no portion of the lumen 2016 contacts any portion the flexible tubular member 108 when the stabilizer 2004 is in a compressed state. When the stabilizer 2004 is in a compressed state, the stabilizer is able to slide over the flexible tubular member 108, and when the stabilizer 2004 is in an uncompressed state, the stabilizer 2004 is unable to slide over the flexible tubular member 108 due to the frictionally contact between the stabilizer 2004 and the flexible tubular member 108. Upon release of the stabilizer 2004 by the clinician, the stabilizer 2004 returns to an uncompressed state, and the shape of the lumen 2016 returns to that of the oval depicted in FIG. 22B, thereby creating contact between the stabilizer 2004 and the flexible tubular member 108 and preventing sliding of the stabilizer 2004 over the flexible tubular member 108 due to the friction between the two components.

The surface of the distal end of the distal portion 2008 of the stabilizer 2004 is flat or relatively flat. The flat shape of the distal end of the distal portion 2008 insures that the stabilizer 2004 remains completely outside the patient's nose upon sliding it adjacent thereto. Also, the stabilizer 2004 may comprise a gusset 2006 that buttresses the distal portion 2008 of the stabilizer 2004, particularly the proximal face 2036 of the distal portion 2008

Figure 23:
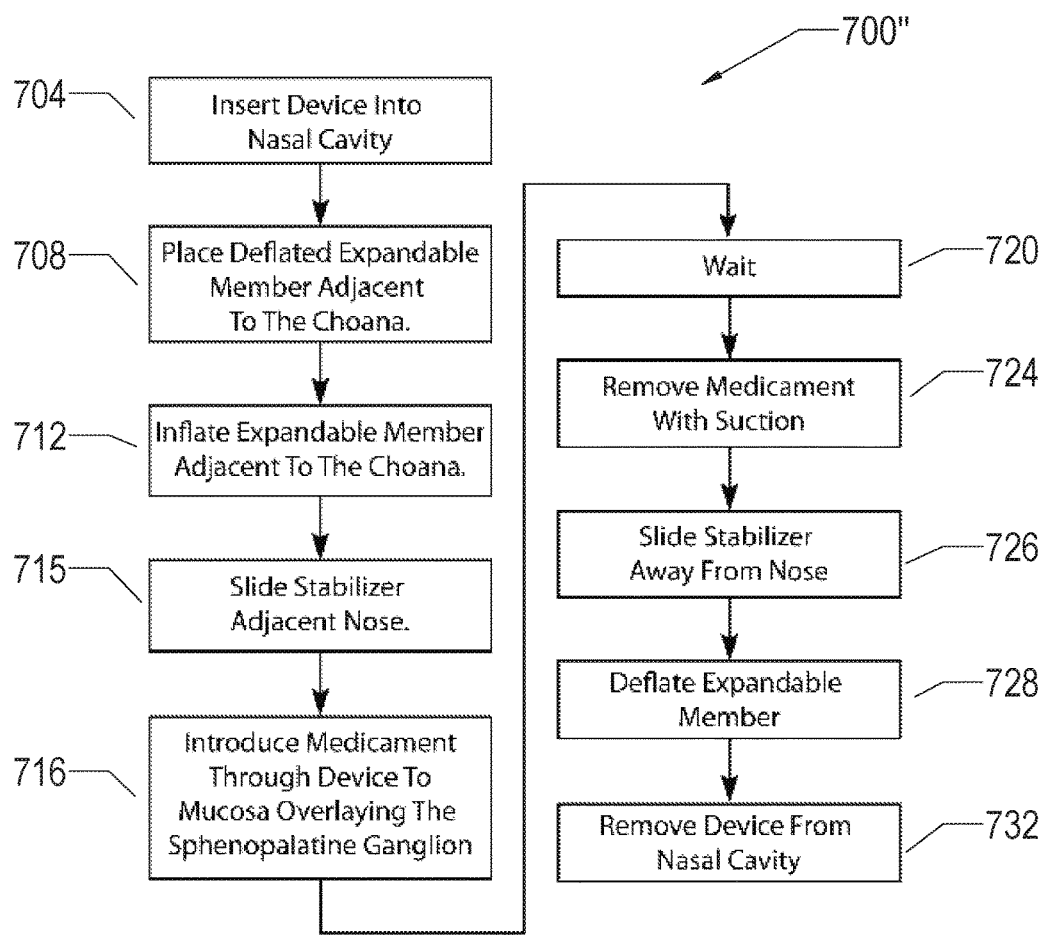
FIG. 23 is flow chart depicting an alternative method of performing a surgical technique using an alternative embodiment of the surgical device of the present disclosure, particularly the alternative embodiment of the surgical device depicted in FIGS. 20A and 20B.

Referring to FIG. 23, there is depicted a flow chart 700" representing at least some of the steps of an alternative method of performing the surgical technique of performing using the alternative embodiment of the surgical device 100''' of the present disclosure. The flow chart 700" depicted in FIG. 23 is similar to the flow chart depicted in FIG. 7, with the exception that the flow chart 700" depicted in FIG. 23 also includes one or both of the following steps: step 715, which includes sliding the stabilizer 2004 adjacent and/or against the patient's nose (after step 712 and prior to step 716); and step 726, which includes sliding the stabilizer 2004 away from the nose (after step 724 and prior to step 728). Although steps 715 and 726, as well as the other steps, are depicted in certain locations within the flowchart, these steps do not necessarily need to be performed in this particular order during the surgical procedure. For example, steps 715 and 726 may be performed prior and/or after other steps depicted within the process. Regardless of where steps 715 and 726 are performed during the sphenopalatine ganglion block procedure, utilizing the stabilizer 2004 aids in holding the expandable member 116 (and/or the expandable member 118) in position while the clinician is performing this surgical procedure.

Figure 24:
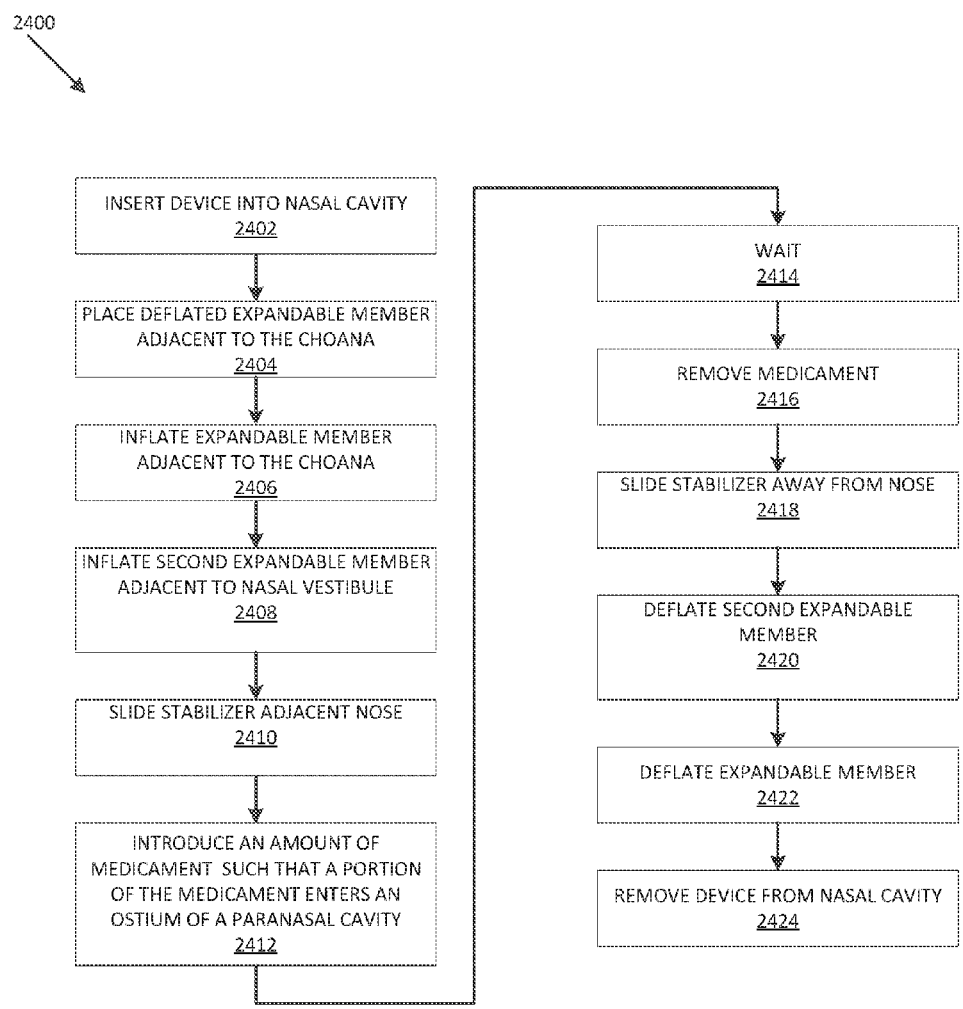
FIG. 24 is a flow chart depicting an exemplary method for treating sinus diseases.

Referring to FIG. 24, a flow chart of an exemplary method 2400 that includes at least some of the steps for treating sinus diseases utilizing one of the surgical devices 100, 100', 100", 100''' is depicted. In some embodiments, method 800 can be performed concurrently with a balloon sinus ostia dilation procedure. In some embodiments, method 800 can be performed after a balloon sinus ostia dilation procedure. In some embodiments, method 800 can be performed after a procedure that removes tissue from an ostia of a paranasal sinus. In even other embodiments, method 800 is not performed concurrent with (or after) a balloon sinus ostia dilation procedure and is not performed after a procedure that removes tissue from an ostia of a paranasal sinus.

Some of the steps of method 2400 are illustrated in FIGS. 6A-6E. Step 2402, which is illustrated in FIG. 6A, includes inserting one of the surgical devices 100, 100', 100", 100''' into the patient's nasal cavity through one of the patients nostrils (i.e., left nostril or right nostril). Specifically, the distal portion of the distal end 124 of the elongated flexible tubular member 108 is preferably inserted into the patient's nostril, while the expandable member 116 is entirely or partially deflated, and directed into the channel below the inferior turbinate and above the hard palate. It may also be preferable at the time of insertion of one of the surgical devices 100, 100', 100", 100''' or shortly thereafter, that the illumination device 216 be activated. Upon activating the illumination device 216, light will transmit through the patient's hard palate. For example, when the distal end 124 of the elongated flexible tubular member 108 (and the illumination device 216) is located within the patient's nasal cavity as depicted in FIG. 6A, the illumination device 216 will be located at or below the posterior inferior turbinate and above the hard palate and be visible to a clinician viewing the interior of the oral cavity (patient's mouth), particularly the bottom of the palate (roof of the patient's mouth), and the light will appear to be transilluminating therefrom within the patient's head and visible to clinician from the oral cavity.

Referring to FIG. 6B, while continuing to activate the illumination device 216 and while the expandable member 116 is entirely or partially deflated, the distal portion of the distal end 124 of the elongated flexible tubular member 108 is inserted further into the patient's nasal cavity. When the distal end 124 of the elongated flexible tubular member 108 (and the illumination device 216) is located within the patient's nasal cavity as depicted in FIG. 6B, the illumination device 216 will continue to be located below the anterior of the inferior turbinate above the anterior of the hard palate further towards the soft palate in comparison location depicted in FIG. 6A.

Referring to FIG. 6C, while continuing to activate the illumination device 216 and while the expandable member 116 is entirely or partially deflated, the distal portion of the distal end 124 of the elongated flexible tubular member 108 is even inserted further into the patient's nasal cavity. When the distal end 124 of the elongated flexible tubular member 108 is located within the patient's nasal cavity as depicted in FIG. 6C, the illumination device 216 will be located above the soft palate, namely the nasopharynx, and the light will appear to be transilluminating therefrom and visible to clinician from the oral cavity. At this point, step 2404 of FIG. 24 has been completed because the expandable member 116 is located at the desired position, namely in the nasopharynx adjacent the choana.

It may also be preferable to include depth markers printed on the elongated flexible tubular member 108, wherein the depth markers indicate to the clinician the distance from the expandable member 116 to the corresponding depth marker. For example, it may be preferable for the elongated flexible tubular member 108 to include depth markers every 1 centimeter, every 5 centimeters, every 10 centimeters from the proximal, mid- or distal portion of the balloon (or from the distal end of the flexible tubular member 108) to the corresponding depth marker. Adding such depth markers may provide the clinician with an additional or alternative means of determining whether the expandable member 116 and/or the distal end of the flexible tubular member 108 is located at the desired position, namely in the nasopharynx adjacent the choana.

Referring to FIG. 6D, when the illumination device 216 and the expandable member 116 are located in the nasopharynx adjacent the choana, the expandable member 116 is expanded by depressing plunger 164 of the syringe 112, as depicted in step 2406 of FIG. 24, thereby blocking the choana.

In some embodiments, if the surgical device 100' is being used, the second expandable member 118 may be used to prevent the medication from exiting the patient's nostril. That is, as depicted in FIG. 11A, after or in conjunction with introducing the surgical device 100' through the patient's nostril and/or locating the expandable member 116 the choana, the second expandable member 118 is disposed adjacent the exterior of the patient's nostril or in the patient's nostril, and the second expandable member 118 is inflated (step 2408). Inflating the expandable member 116 adjacent the choana and the second expandable member 118 adjacent patient's nostril allows the medication to collect between the two expandable members 116, 118 while preventing the medication from flowing down the patient's throat and escaping through the patient's nostril, particularly if the patient moves his/her head and/or when the patient's head is not in the most desirable orientation. Although step 2408 is depicted in a certain location within method 2400, step 2408 does not necessarily need to be performed in this particular order of method 2400. For example, step 2408 may be performed prior and/or after other steps depicted within method 2400.

In some embodiments, if the surgical device 100''' is being used, a stabilizer 2004 may be used to hold the expandable member 116 (and/or the expandable member 118) in position while the clinician is performing this surgical procedure for treating sinus diseases. That is, as depicted in FIG. 21B, method 2400 can include sliding the stabilizer 2004 adjacent and/or against the patient's nose (step 2410). Although step 2410 is depicted in a certain location within method 2400, step 2410 does not necessarily need to be performed in this particular order of method 2400. For example, step 2410 may be performed prior and/or after other steps depicted within method 2400.

Once the choana is blocked, a medicament is introduced to the nasal cavity (step 2412). In some embodiments, a medicament can be introduced to the nasal cavity through the opening 160 of the flexible tubular member 108. In other embodiments, a medicament can be introduced to the nasal cavity through the nasal vestibule. As the medicament is introduced, the expanded expandable member 116 prevents the flow of medication down the patient's throat.

Figure 25A:
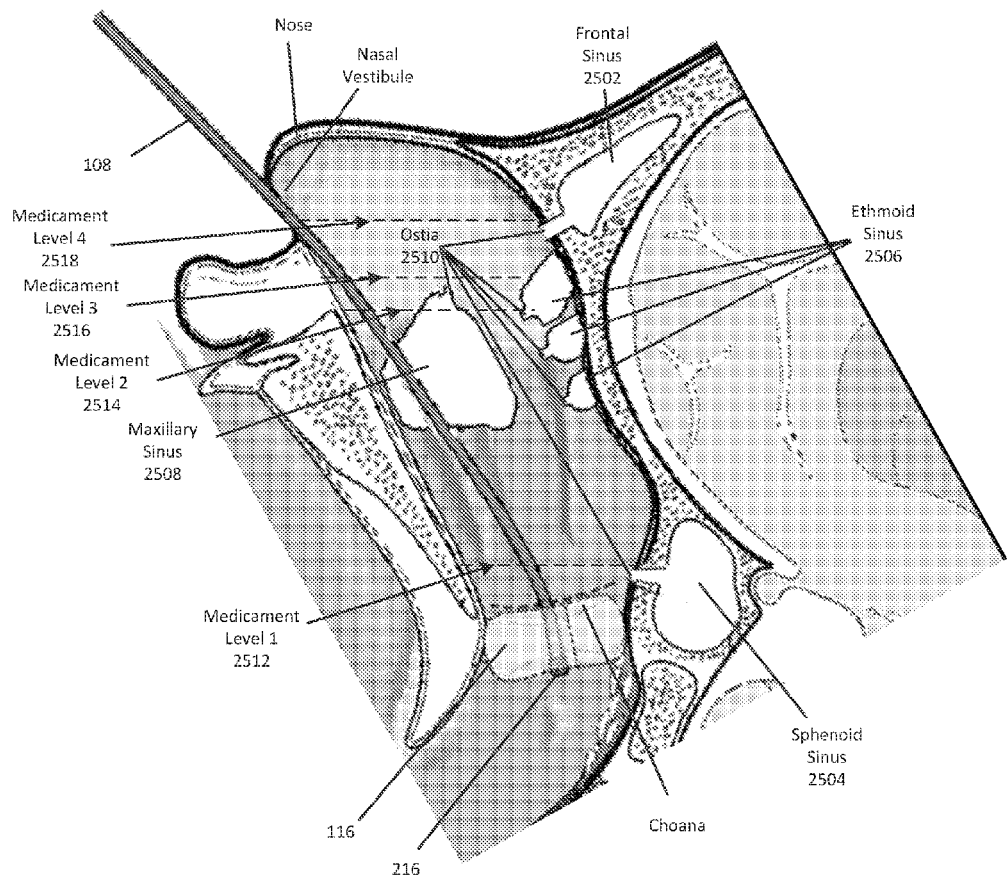
FIG. 25A is a cross-sectional view of a patient's head with an embodiment of a surgical device of the present disclosure, with the expandable member in an inflated state, located in the patient's nasal cavity with the expandable member disposed adjacent the choana, and medication accumulated in the patient's nasal cavity such that at least some of the medication can enter an ostium of at least one paranasal sinus.

Referring to FIG. 25A, and as discussed above, paranasal sinuses 2502, 2504, 2506, 2508 include the frontal sinuses 2502, the sphenoid sinuses 2504, the ethmoid sinuses 2506, and the maxillary sinuses 2508. Each paranasal sinus 2502, 2504, 2506, 2508 has a respective ostium 2510 that allows mucous produced in the paranasal sinus 2502, 2504, 2506, 2508 to drain. In some embodiments, the patient's head can be tilted backwards during method 2400, as shown in FIG. 25A. In these embodiments, because the patient's head is tilted backwards, the medication collects proximally above the expandable member 116. Accordingly, the medication begins to accumulate within the nasal cavity. Upon a certain volume of medication being introduced to the nasal cavity, medication will accumulate in the nasal cavity such that the medication rises to a level and enters an ostium 2510 of at least one paranasal sinus 2502, 2504, 2506, 2508 and accumulates in the corresponding paranasal sinus 2502, 2504, 2506, 2508 (step 2412). Depending upon the size of the patient's nasal cavity and paranasal sinuses the volume of medication introduced to the nasal cavity and used to create such a pool may be between 2 milliliters to 250 milliliters and potentially preferable between 50 milliliters to 200 milliliters and potentially further preferable between 100 milliliters to 150 milliliters. As discussed below, different medication levels can be obtained, depending on the orientation of the patient's head and the volume of medication introduced to the patient's nasal cavity.

For example, in some embodiments, a first volume of medication can be introduced to the nasal cavity such that the medication rises to a medicament level 1 2512. In this embodiment, with the head tilted back as shown in FIG. 25A, the medication can enter an ostium 2510 of the sphenoid sinus 2504. Moreover, in this embodiment, the sphenoid sinus 2504 will partially fill with the medicament. In other embodiments, a volume of medication can be introduced to the nasal cavity such that the sphenoid sinus 2504 completely fills with the medication.

As another example, in some embodiments, a second volume of medication can be introduced to the nasal cavity such that the medication rises to a medicament level 2 2514. In this embodiment, with the head tilted back as shown in FIG. 25A, the medication can enter an ostium 2510 of the ethmoid sinus 2506. Moreover, in this embodiment, the ethmoid sinus 2506 will partially fill with the medicament. In other embodiments, a volume of medication can be introduced to the nasal cavity such that the ethmoid sinus 2506 completely fills with the medication.

As another example, in some embodiments, a third volume of medication can be introduced to the nasal cavity such that the medication rises to a medicament level 3 2516. In this embodiment, with the head tilted back as shown in FIG. 25A, the medication can enter an ostium 2510 of the maxillary sinus 2508. Moreover, in this embodiment, the maxillary sinus 2508 will completely fill with the medicament, due to the orientation of the patient's head.

As another example, in some embodiments, a fourth volume of medication can be introduced to the nasal cavity such that the medication rises to a medicament level 4 2518. In this embodiment, with the head tilted back as shown in FIG. 25A, the medication can enter an ostium 2510 of the frontal sinus 2502. Moreover, in this embodiment, the frontal sinus 2502 will partially fill with the medicament. In other embodiments, a volume of medication can be introduced to the nasal cavity such that the frontal sinus 2502 completely fills with the medication.

Figure 25B:
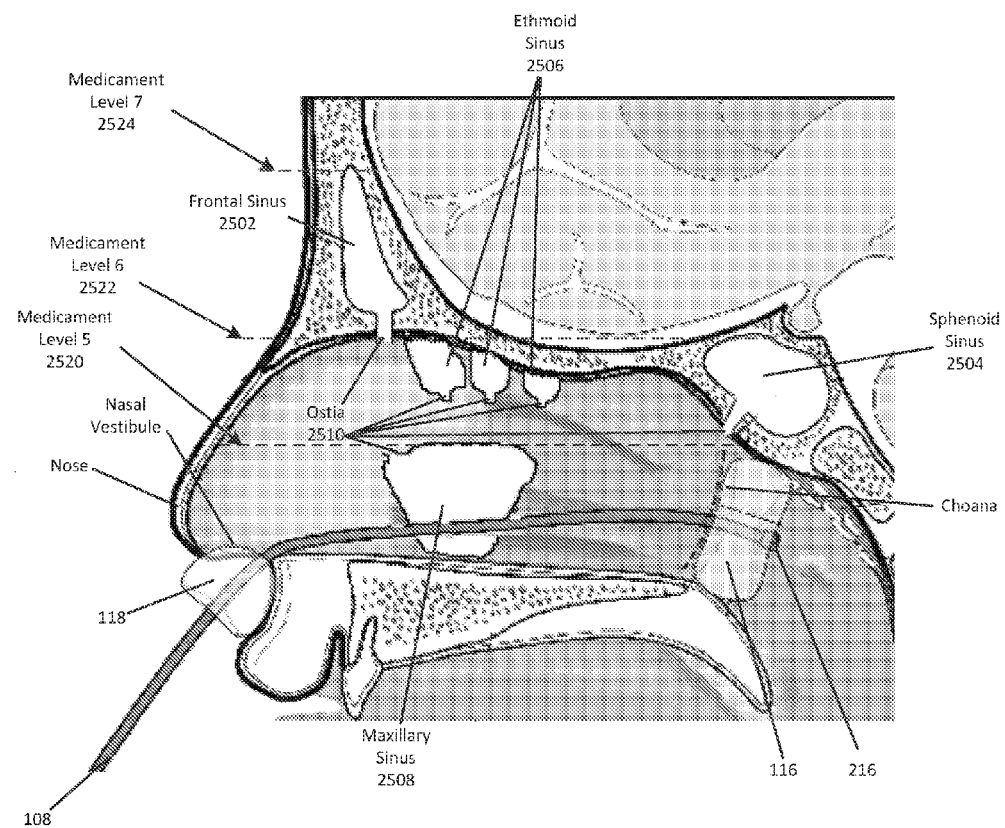
FIG. 25B is a cross-sectional view of a patient's head with an embodiment of a surgical device of the present disclosure, with the expandable member in an inflated state, located in the patient's nasal cavity with the expandable member disposed adjacent the choana, a second expandable member disposed adjacent and exterior to the patient's nostril, and medication accumulated in the patient's nasal cavity such that at least some of the medication can enter an ostium of at least one paranasal sinus.

Referring to FIG. 25B, in some embodiments, if the surgical device 100' is being used, the second expandable member 118 may be used to prevent the medication from exiting the patient's nostril, as explained above, regardless of the orientation (tilting) of the patients head. In these embodiments, since the patient's head is not tilted back, different volumes of medicament can be introduced to the nasal cavity so that at least a portion of the medication can enter an ostium 2510 of at least one paranasal sinus 2502, 2504, 2506, 2508 (step 2412).

For example, in some embodiments, a fifth volume of medication can be introduced to the nasal cavity such that the medication rises to a medicament level 5 2520. In this embodiment, with the patient's head oriented as shown in FIG. 25B, the medication can enter an ostium 2510 of the maxillary sinus 2508. Moreover, in this embodiment, the maxillary sinus 2508 will completely fill with the medicament.

As another example, in some embodiments, a sixth volume of medication can be introduced to the nasal cavity such that the medication rises to a medicament level 6 2522. In this embodiment, with the patient's head oriented as shown in FIG. 25B, the medication can enter an ostium 2510 of the ethmoid sinus 2506, the frontal sinus 2502 and the sphenoid sinus 2504. Moreover, in this embodiment, the ethmoid sinus 2506 and the sphenoid sinus 2504 will completely fill with the medicament.

As another example, in some embodiments, a seventh volume of medication can be introduced to the nasal cavity such that the medication rises to a medicament level 7 2524. In this embodiment, with the patient's head oriented as shown in FIG. 25B, the medication can enter an ostium 2510 of the frontal sinus 2508 and completely fill the frontal sinus 2502 with the medicament.

Introducing the medication according to the examples described above and maintaining the desired level of medication provides for direct and sustained contact with an ostium 2510 and/or at least a portion of a paranasal sinus 2502, 2504, 2506, 2508. The medication can then be absorbed by the ostium 2510 and/or at least a portion of the paranasal sinus 2502, 2504, 2506, 2508. In comparison to spraying an ostium 2510 or of a paranasal sinus 2502, 2504, 2506, 2508, the device(s) and method(s) of the present disclosure provide direct and sustained contact with the ostium 2510 and/or at least a portion of the paranasal sinus 2502, 2504, 2506, 2508, which is a more effective treatment. Also, varying the medication and contact times may further increase the effectiveness of the treatment. Varying the medication and contact times also provide the clinician the flexibility to personalize the patient's treatment. Another example of the way in which the clinician may utilize the device(s) and method(s) of the present disclosure to personalize the patient's treatment includes inflating the inflatable member to a certain pressure.

Referring to step 2414 of FIG. 24, it may be preferable for the medication to remain within the nasal cavity and contact a portion of a paranasal sinus 2502, 2504, 2506, 2508 for a predetermined period of time. For example, it may be desirable for the medication to remain in the patient's nasal cavity contact a portion of a paranasal sinus 2502, 2504, 2506, 2508 for a period of time from about 5 minutes to 40 minutes, including any time interval (e.g., 1 minute, 2 minutes, 3 minutes, 4 minutes, 5 minutes, etc.) there between. It may be more desirable for such time period to be about 10 minutes to 30 minutes, and even more desirable for such time period to be about 15 minutes to 25 minutes, and even further desirable for such time period to be about 20 minutes.

Referring to step 2416, upon a portion of a paranasal sinus 2502, 2504, 2506, 2508 being directly exposed to the medication for the desired period, the medication is removed from the nasal cavity. In some embodiments, the medication can be removed from the nasal cavity by suctioning the medication through the opening 160 with an auxiliary syringe. In other embodiments, the medication can be removed from the nasal cavity by draining the medication out of the nasal vestibule. In embodiments where the surgical device 100''' is being used, once the medication is removed, the stabilizer 2004 may be slide away from the patient's nose (step 2418). In embodiments where the surgical device 100' is being used, once the medication is removed, the second expandable member 118 may be deflated (step 2420). After which, the expandable member 116 may be collapsed by retracting the plunger 164 of the syringe 112, as depicted in step 2422 of FIG. 24. As set forth in step 2424, after the medication is removed and the expandable member 116 is collapsed, the surgical device 100 may be removed from the nasal cavity.

The method discussed above with respect to FIG. 24 discloses treating a sinus diseases utilizing one of the surgical devices 100, 100', 100'', 100''' located on one (i.e., left or right) side of the patient's head. Upon completing the method for one side of the head, the same procedure can be repeated as outlined in FIG. 24, by inserting the distal end of the elongated flexible tubular member 108 of the surgical devices 100, 100', 100'', 100''' into the patient's other nostril and applying the medication to the paranasal sinus other side of the head, among the other steps.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. For example, the device(s) described in the present disclosure may be used in conjunction with other medical devices. Specifically, prior to inserting the device(s), which are described in the present disclosure into the patient's nasal cavity, the clinician may first use an endoscope or other medical device to perform a nasal examination and inspect the patient's nasal cavity and insure that nasal mucosa is intact and there are not any obvious internal anatomic obstruction within the patient's nasal cavity that would prevent the passage of the device described herein, which may have a diameter of about 4 mm. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treating a sinus disease, the method comprising the steps of:
   (a) inserting a portion of a device into a nasal cavity of a patient through a nostril, the device comprising:
      a handle comprising a proximal end and a distal end;
      an inflation device at least partially disposed within the handle;
      a flexible tubular member extending from the distal end of the handle, the flexible tubular member comprising a proximal end, a distal end, an inflation lumen coupled to the inflation device and extending from the proximal end of the flexible tubular member, and a second lumen extending from the proximal end of the flexible tubular member to a medication port; and
      an expandable member attached to the flexible tubular member, the expandable member comprising a proximal end and a distal end, wherein the inflation lumen opens, via an inflation port, into the expandable member, wherein the medication port is disposed proximally of the proximal end of the expandable member;
   (b) expanding, using the inflation lumen, the expandable member adjacent to the patient's choana;
   (c) introducing an amount of medication into the nasal cavity, such that at least a portion of the medication enters an ostium of a paranasal sinus of the patient and enters the paranasal sinus and at least a portion of the medication remains in the paranasal sinus for a period of 5 minutes to 40 minutes;
   (d) collapsing the expandable member; and
   (e) removing the device from the nasal cavity.

2. The method of claim 1, wherein the device further comprises an illumination device disposed adjacent the distal end of the flexible tubular member and distally of the expandable member.

3. The method of claim 2, further comprising the step of activating the illumination device.

4. The method of claim 3, further comprising the step of viewing light emitted from the illumination device through a portion of the patient's soft palate.

5. The method of claim 1, wherein the device further comprises a stabilizer slidably coupled to the flexible tubular member, and wherein the stabilizer is capable of sliding along the flexible tubular member between the handle and the expandable member.

6. The method of claim 5, further comprising the step of sliding the stabilizer toward and/or away from the patient's nose when the portion of the device is inserted in the nasal cavity.

7. The method of claim 1, further comprising the step of removing at least a portion of the medication through the medication port in the flexible tubular member.

8. The method of claim 1, further comprising the step of inserting the device into a second portion of the nasal cavity of the patient through a second nostril and performing steps (b) through (e).

9. The method of claim 1, wherein the level of medication is maintained for 10 minutes to 30 minutes.

10. The method of claim 9, wherein the level of medication is maintained for 15 minutes to 25 minutes.

11. The method of claim 10, wherein the level of medication is maintained for at least 20 minutes.

12. The method of claim 1, wherein the amount of the medication introduced to the nasal cavity is between 2 milliliters to 250 milliliters.

13. The method of claim 12, wherein the amount of the medication introduced to the nasal cavity is between 50 milliliters to 200 milliliters.

14. The method of claim 13, wherein the amount of the medication introduced to the nasal cavity is between 100 milliliters to 150 milliliters.

15. The method of claim 1, wherein the step of expanding the expandable member adjacent to the patient's choana comprises placing the expandable member in the patient's nasopharynx.

\* \* \* \* \*